| United States Patent [19] | [11] Patent Number: 5,019,153 |
| Lee et al. | [45] Date of Patent: May 28, 1991 |

[54] SUBSTITUTED PYRIDINE HERBICIDES

[75] Inventors: Len F. Lee, St. Charles, Mo.; Mark G. Dolson, San Pablo, Calif.

[73] Assignee: Monsanto Company, St. Louis, Mo.

[21] Appl. No.: 444,587

[22] Filed: Dec. 1, 1989

Related U.S. Application Data

[62] Division of Ser. No. 861,954, May 12, 1986, Pat. No. 4,885,026.

[51] Int. Cl.$^5$ .................... C07D 213/80; A01N 43/40
[52] U.S. Cl. .......................................... 71/94; 546/298; 546/315; 546/318
[58] Field of Search ...................... 546/298, 315, 318; 71/94

[56] References Cited

U.S. PATENT DOCUMENTS

| 3,637,716 | 1/1972 | Bimber et al. | 546/287 |
| 3,705,170 | 12/1972 | Torba | 546/295 |
| 3,748,334 | 7/1973 | Riglerink et al. | 546/303 |
| 4,789,395 | 12/1988 | Lee et al. | 546/292 |
| 4,835,279 | 5/1989 | Lee et al. | 546/318 |

OTHER PUBLICATIONS

CA:105:190960y, Lee et al., 2,6–Substituted Pyridine Compounds, 11/6/84.
CA:105:133760f, Lee et al., 2,6–Substituted Pyridine Compounds, 11/6/84.

Primary Examiner—Frederick E. Waddell
Assistant Examiner—Catherine S. Kilby Scalzo
Attorney, Agent, or Firm—Stanley M. Tarter; James C. Bolding

[57] ABSTRACT

Disclosed are pyridine herbicides characterized by substitution with a fluorine-containing methyl group at the 2- or 6-position, a carboxylic acid-derived group at the 3-position, and a halogen or a substituted nitrogen-containing group at the 5-position.

18 Claims, No Drawings

SUBSTITUTED PYRIDINE HERBICIDES

This is a DIVISION of application Ser. No. 06/861,954, filed May 12, 1986 (now U.S. Pat. No. 4,855,026).

This invention relates to a new class of 2,6-substituted pyridinecarboxylic acid derivatives having a wide range of activity as herbicides.

Pyridine derivatives have, for many years, been investigated for use in the biological sciences. For example, 2,6-bis-(trifluoromethyl)-4-pyridinols have been found useful as herbicides and fungicides as disclosed in U.S. Pat. No. 3,748,334. Such compounds are characterized by substitution in the 4-position by a hydroxyl radical. In addition to the hydroxyl radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO patent 44,262 there are disclosed 2,6-dialkyl-3-phenylcarbamyl-5-pyridinecarboxylates and -5-cyano-compounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intraveneous injection of such compounds.

Pyridine dicarboxylate compounds useful as herbicides are described in European Patent publication 133,612 which corresponds to U.S. Pat. No. 4,592,184. These compounds have fluorinated methyl groups at the 2- and 6-positions and carboxylic acid derivative at the 3- and 5-positions.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

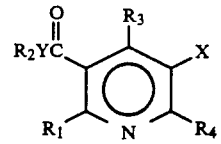

wherein:

Y is selected from O and S;

$R_1$ and $R_4$ are independently selected from fluorinated methyl, chlorofluorinated methyl, and $C_1$-$C_4$ alkyl, provided that not both $R_1$ and $R_4$ may be $C_1$-$C_4$ alkyl;

$R_2$ is selected from hydrogen, lower alkyl, haloalkyl, alkenyl, alkynyl, haloalkenyl, aryl, benzyl, and a cation;

$R_3$ is selected from $C_1$-$C_5$ alkyl, cycloalkyl, cycloalkylalkyl, hydroxy, alkoxy, alkylthio, dialkylamino, alkylamino, cycloalkylamino, cycloalkoxy, and cycloalkylthio; and X is selected from a) a halogen;

b)

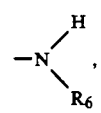

where $R_6$ is selected from H,

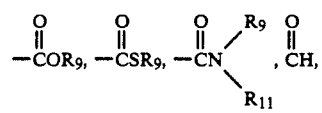

which $R_9$ is $C_1$-$C_4$ alkyl, $R_{11}$ is selected from H and $C_1$-$C_4$ alkyl, $R_{12}$ is selected from $R^1$ and lower haloalkyl, where $R^1$ is $C_1$-$C_4$ alkyl, $R_{13}$ is hydrogen, alkyl, or haloalkyl;

c) —$N_3$;

d)

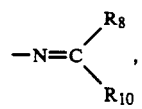

in which $R_8$ is selected from H, alkyl and $CF_3$ and $R_{10}$ is selected from F, Cl, —$OR^1$, —$SR^1$, —$NHR^1$, —$N(R^1)_2$, phenyl, substituted phenyl, and —$P(OR^1)_2$; where $R^1$ is as defined above;

e) —N=S=O;

f) —$NO_2$;

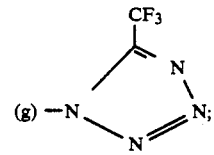

-continued

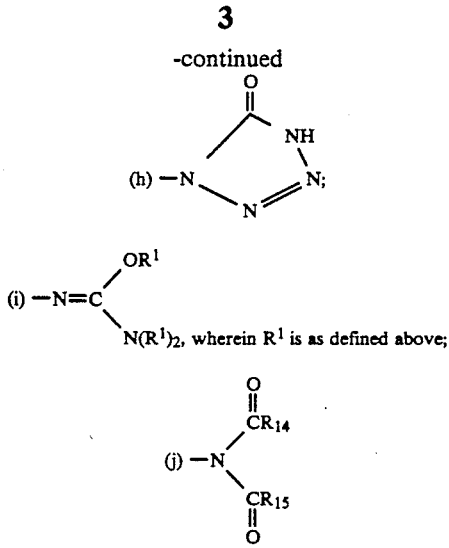

wherein $R_{14}$ and $R_{15}$ are independently selected from hydrogen and alkyl; and k) —N=C=O The term ʃalkyl" means herein both straight and branched chain radicals which include, but are not limited to, ethyl, methyl, n-propyl, 1-ethylpropyl, 1-methylpropyl, n-butyl, 2,2-dimethylpropyl, pentyl, isobutyl, isopropyl. The term "cycloalkyl" is intended to mean saturated cyclic radicals such as cyclopropyl, cyclobutyl, cyclopentyl, cyclohexyl, and cycloheptyl, as well as substituted cycloalkyl radicals.

The term "lower alkyl" herein means an alkyl radical having 1 to 7 carbon atoms.

The term "cycloalkylalkyl" is intended to mean alkyl radicals substituted with a $C_{3-6}$ cycloalkyl radical. The term "haloalkyl" is intended to mean alkyl radicals substituted with one or more halogen atoms. The terms "lower alkenyl" and "lower alkynyl" herein mean alkenyl and alkynyl groups having 3 to 7 carbon atoms.

Examples of such alkenyl groups include 2-propenyl, 2-butenyl, 3-butenyl, 2-methyl-2-propenyl, and the like. Examples of such lower alkynyl groups include 2-propenyl, and so forth.

The term "cation" means any cation derived from a base providing a salt. Typical cations include, but are not limited to, alkali metals such as sodium, potassium, and lithium, alkaline earth metals such as calcium, organic amines, and ammonium salts, sulfonium salts, phosphonium salts, and other salt complexes.

The term "fluorinated methyl" means herein methyl radicals having one or more fluorine atoms attached thereto including radicals wherein all hydrogen atoms replaced by fluorine.

The term "chlorofluorinated methyl" means herein a methyl radical having at least one hydrogen replaced by fluorine and at least one other hydrogen replaced by chlorine.

DETAILED DESCRIPTION OF THE INVENTION

The schemes shown below schematically depict a method whereby the pyridine monocarboxylate compounds of this invention may be prepared from compounds which are known in the art. Starting with a pyridinedicarboxylate compound such as those described in European Patent Publication No. 133,612, the dicarboxylic acid chloride is prepared by treating with a chlorinating agent such as $PCl_5$ or $SOCl_2$. The or 5-amino-monocarboxylate is then prepared from the 3- or 5-chlorocarbonyl compound by treatment with NaNa followed by a Curtis rearrangement. The 3- or 5-amino compound so produced is then transformed into a 3- or 5-halogen substituted pyridinemonocarboxylate or a compound in which the atom linked to the pyridine ring at the 3- or 5-position is a nitrogen atom as shown in Schemes 2, 3 and 4. Reference to the Examples will provide greater detail about the steps shown in Schemes 1–4.

SCHEME 1

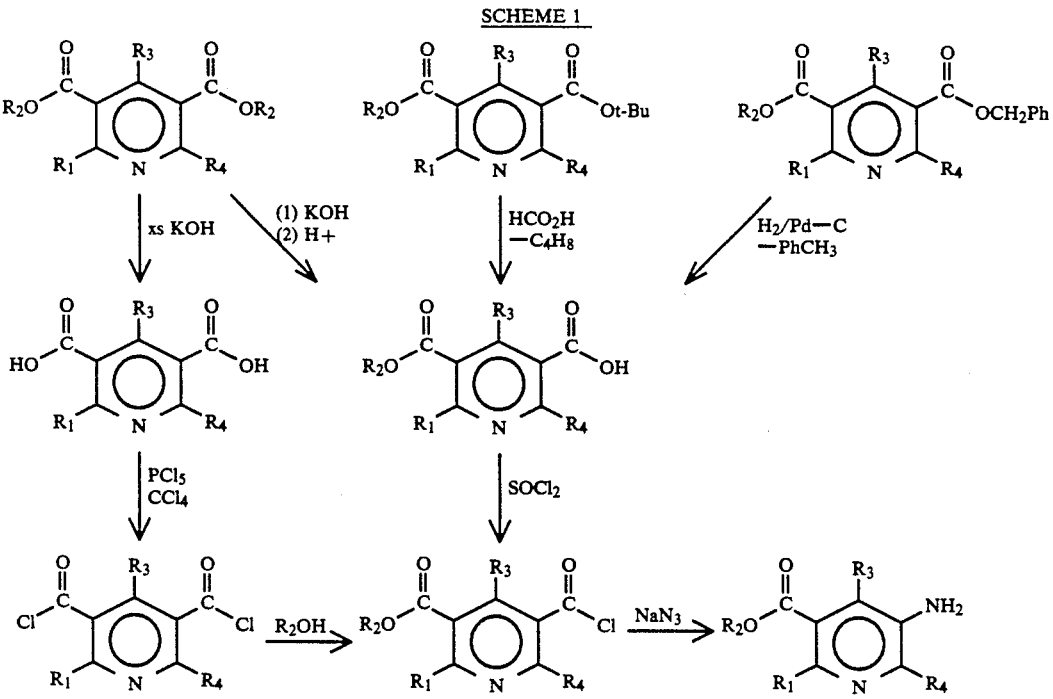

SCHEME 2
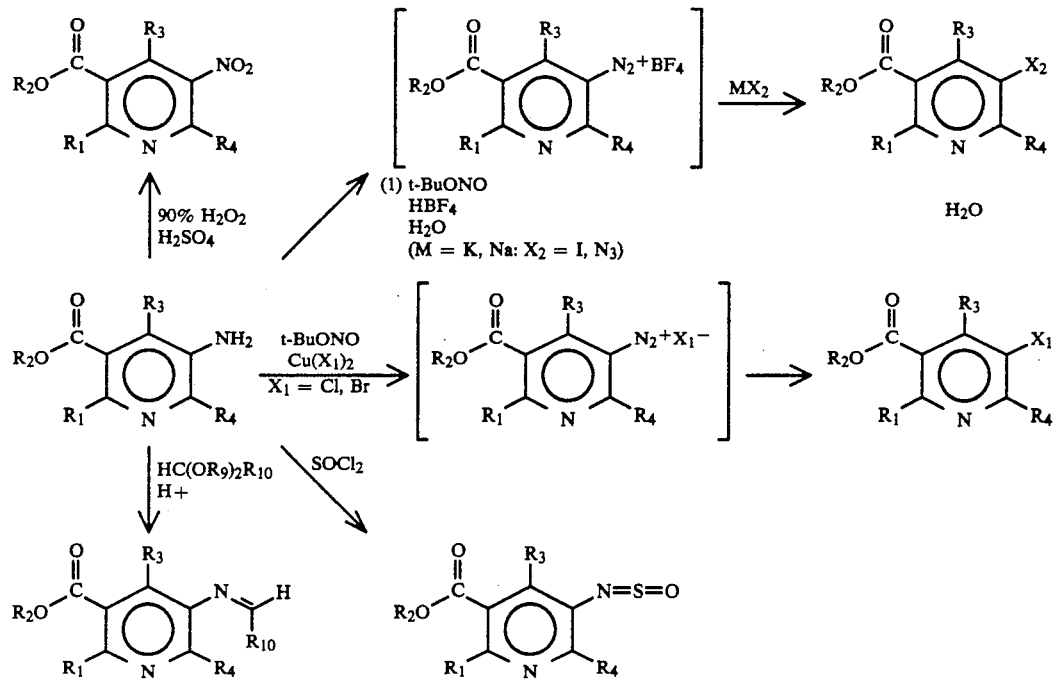
SCHEME 3
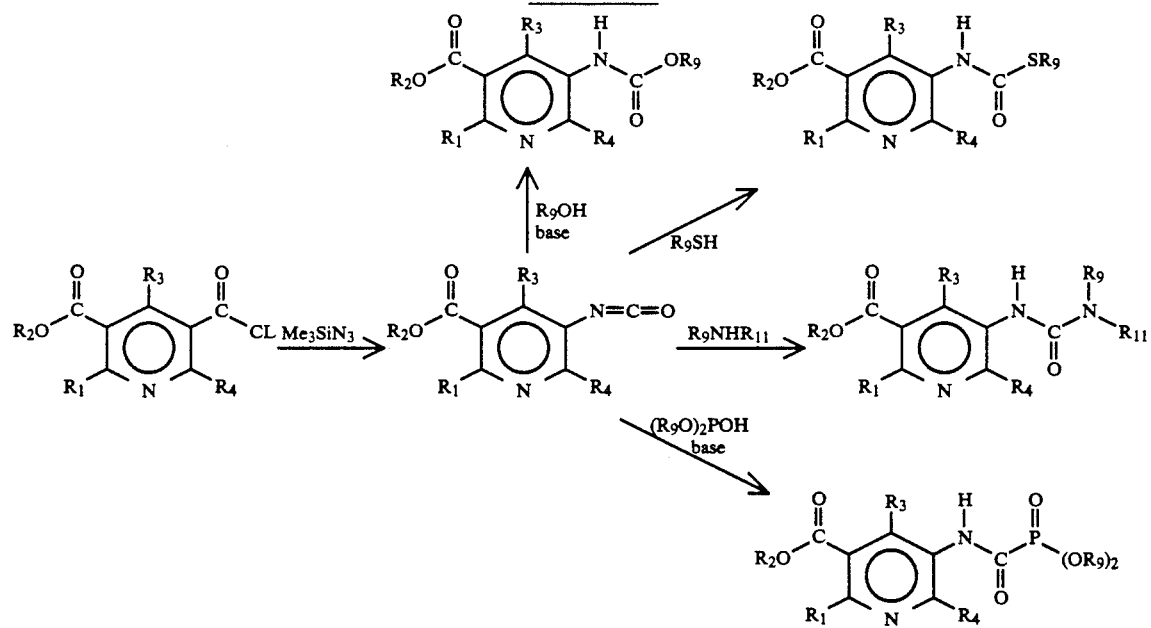
SCHEME 4
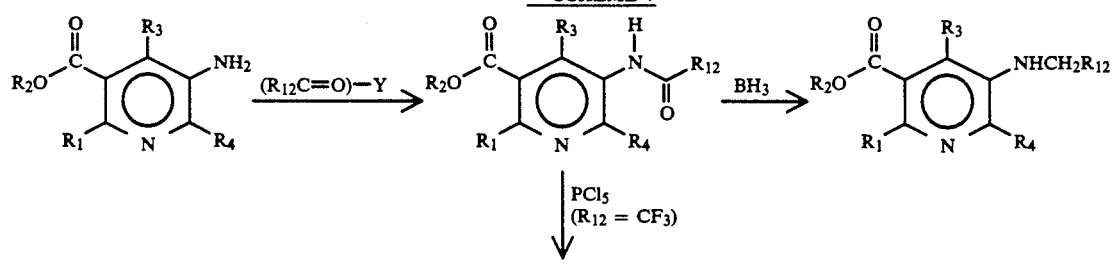

-continued
SCHEME 4

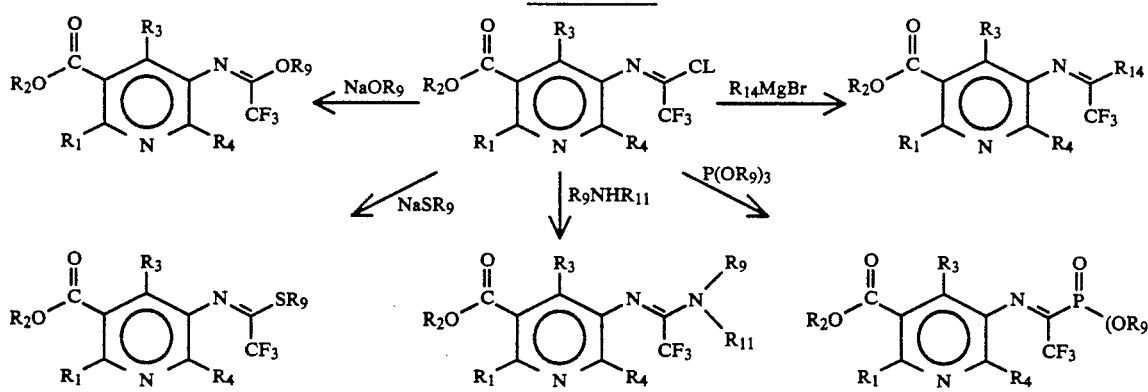

Preparation of further compounds of this invention will become clear by reference to the scheme in conjunction with the following examples.

As used throughout the specification, including the Examples, the following abbreviations have the following meanings:
- LDA—lithium diisopropylamide
- THF—tetrahydrofuran
- DME—dimethyl ether
- DBU—1,8 diazobicyclo-[5.4.0]-undec-5-ene
- DMF—N,N-dimethylformamide
- ETFAA—ethyl trifluoroacetoacetate
- MCPBA—m-chloroperbenzoic acid
- HPLC—high pressure liquid chromatography
- TLC—thin layer chromatography
- n-BuLi—n-Butyl lithium
- DMSO—dimethyl sulfoxide
- Pd/C—hydrogenation catalyst which is palladium deposited on finely-divided carbon
- TsCl—tosyl chloride.

As used in the following Examples, the terms "workup as usual", or "normal workup", or equivalent language refer to the process of washing the organic extract with brine, drying by pouring through a cone of anhydrous sodium sulfate, and concentrating in vacuo.

EXAMPLE 1

3-Pyridinecarboxylic acid, 5-amino-6-(difluoromethyl)-4-isobutyl-2-(trifluoromethyl)-,ethyl ester. Six grams (15.1 mmol) of product of Example 32 of European Patent Application No. 133,612 published Feb. 27, 1985, was added to 0.95 g of 89% potassium hydroxide (15.1 mmol) and 35 mL of ethanol and was stirred at room temperature for 1 day. The reaction mixture was poured into 135 mL of water, washed with ether ($2 \times 20$ mL) and acidified with concentrated hydrochloric acid. The product was extracted into ether ($2 \times 50$ mL), which was worked up as usual to afford 4.91 g (88%) of the desired mono-acid as an off-white solid suitable for further transformation. This was refluxed overnight with thionyl chloride (25 mL). The excess thionyl chloride was removed in vacuo and the resulting acid chloride was added dropwise to a rapidly-stirred slurry of 1.8 g of sodium azide in 15 mL of 4:1 acetone:water. This was stirred at room temperature for the weekend, then diluted with 75 mL of water and extracted with ether (3X20 mL). Workup as usual afforded 4.66 g (91% overall yield) of product as a tan solid. Recrystallization from cyclohexane gave analytically pure material, mp 68°-70° C.

| Elemental Analysis: | C | H | N |
|---|---|---|---|
| Calculated | 49.41 | 5.04 | 8.23 |
| Found | 49.23 | 4.97 | 8.26 |

EXAMPLE 2

3-Pyridinecarboxylic acid, 5-amino-6-(difluoromethyl)-4-ethyl-2-(trifluoromethyl)-,ethyl ester. A mixture of 35.0 g (0.103 mol) of product of Example 55 of European Patent Application No. 133,612 published Feb. 27, 1985, and 60 mL of thionyl chloride was refluxed overnight. The excess thionyl chloride was removed in vacuo, and the acid chloride was diluted with 10 mL of acetone and added to a slurry of 14.3 g of NaN$_3$, 25 ml of H$_2$O, and 90 ml of acetone. An exothermic reaction occurred with vigorous gas evolution. After the reaction mixture cooled to room temperature, 300 mL of water was added and the product was extracted into chloroform. Normal workup gave 30.9 g (96%) of product as a tan solid. Recrystallization from ethyl acetate/cyclohexane afforded analytically pure material, mp 92°-94° C.

| Elemental Analysis: | C | H | N |
|---|---|---|---|
| Calculated | 46.16 | 4.20 | 8.97 |
| Found | 46.08 | 4.23 | 8.94 |

EXAMPLE 3

3-Pyridinecarboxylic acid, 6-(difluoromethyl)-5-[(methoxycarbonyl)amino]-4-(2-methylpropyl) -2-(trifluoromethyl)-, ethyl ester. A mixture of 13.7 g (0.037 mol) of ethyl 6-(difluoromethyl)-5-(chlorocarbonyl)-4-(2-methylpropyl)-2-(trifluoromethyl)-3-pyridinecarboxylate prepared by methods shown in European Patent Application No. 133,612 published Feb. 27, 1985, and 40 ml of thionyl chloride was stirred at reflux for 7 hours, then was concentrated in vacuo. The residue was kugelrohr distilled (130° C. at 1 torr) to give 13.4 g (93%) of the corresponding acid chloride as a yellow oil. To a 0° C. solution of 5.0 g (0.013 mol) of this acid chloride in 50 mL of chloroform was added dropwise a solution of 1.03 g (0.013 mol) of pyridine and 14.5 mL (0.0149 mol) of 1.025 M hydrazoic acid in chloroform. After the addition was complete, the reaction mixture was stirred 30 min at room temperature, diluted with 20 mL of methanol and heated on a hot plate until gas evolution ceased. This was then poured into 100 mL of water and extracted with chloroform (3×40 mL). Normal workup afforded 5.03 g (97%) of product as a tan solid. Recrystallization from ethyl acetate/cyclohexane afforded analytically pure material, mp 109°–110° C.

| Elemental Analysis: | C | H | N |
|---|---|---|---|
| Calculated | 48.25 | 4.81 | 7.03 |
| Found | 48.03 | 4.76 | 7.21 |

EXAMPLE 4

3-Pyridinecarboxylic acid, 5-({[Bis (1-methylethyl)amino]carbonyl}amino)-6-(difluoromethyl)-4-(2-methylpropyl)-2-(trifluoromethyl)-, ethyl ester. A mixture of 13.7 g (0.037 mol) of ethyl 6-(difluoromethyl)-5-(chlorocarbonyl)-4-(2-methylpropyl)-2-(trifluoromethyl)-3-pyridinecarboxylate prepared by methods shown in European Patent Application No. 133,612 published Feb. 27, 1985, and 40 ml of thionyl chloride was stirred at reflux for 7 hours, then was concentrated in vacuo. The residue was kugelrohr distilled (130° C. at 1 torr) to give 13.4 g (93%) of the corresponding acid chloride as a yellow oil. A 0° C. solution of 5.0 g (0.013 mmol) of this acid chloride in 50 mL of chloroform was added dropwise to a solution of 1.03 g (0.013 mol) of pyridine and 14.5 mL (0.015 mol) of 1.025 M hydrazoic acid in chloroform. After the addition was complete, it was stirred at room temperature for 30 min. Then 20 mL of diisopropylamine was added causing an exothermic reaction to occur. The reaction was allowed to cool to room temperature and diluted with 100 mL of water. The product was extracted into chloroform (3×40 mL). Normal workup afforded 5.54 g (91%) of product as a tan solid. Recrystallization from ethyl acetate/cyclohexane afforded analytically pure material, mp 137°–139° C.

| Elemental Analysis: | C | H | N |
|---|---|---|---|
| Calculated | 53.96 | 6.47 | 8.99 |
| Found | 53.91 | 6.46 | 8.95 |

EXAMPLE 5

3-Pyridinecarboxylic acid, 5-amino-6-(diflurome thyl)-4-ethyl-2-(trifluoromethyl)-,methyl ester. A mixture of 45.0 g (0.132 mol) of methyl 5-carboxy-6-(difluoromethyl)-4-ethyl-2-(trifluoromethyl)-3-pyridinecarboxylate prepared by methods shown in European Patent Application No. 133,612 published Feb. 27, 1985, 8.91 g (0.135 mol) of 85% potassium hydroxide, 125 ml of methanol and 15 ml of water was stirred at room temperature for 24 hours. The reaction mixture was poured into water (500 ml), washed with chloroform (2×200 ml), and then was acidified with concentrated hydrochloric acid. Extraction with ethyl acetate (3×150 ml) followed by workup as usual afforded 38.2 g (88%) of the corresponding carboxylic acid as a white solid. A solution of 38.2 g (0.117 mol) of this acid and 50 mL of thionyl chloride was refluxed for 3 h. The excess thionyl chloride was removed in vacuo and the remaining acid chloride was dissolved in acetone (15 mL). This was added to a rapidly stirred slurry of 17.8 g (0.27 mol) of sodium azide, 30 mL of water and 100 mL of acetone, resulting in an exothermic reaction with vigorous gas evolution. After 2 h, the reaction mixture was diluted with 200 mL of water and extracted with chloroform (3×70 mL). Normal workup afforded 33.0 g (86%) of product as a tan solid. Recrystallization from ethyl acetate/cyclohexane afforded analytically pure material, mp 92°–93° C.

| Elemental Analysis: | C | H | N |
|---|---|---|---|
| Calculated | 44.30 | 3.72 | 9.39 |
| Found | 44.59 | 3.83 | 9.16 |

EXAMPLE 6

3-Pyridinecarboxylic acid, 6-(difluoromethyl)-4-ethyl-5-[(methoxycarbonyl)amino]-2-(trifluoromethyl)-,ethyl ester. A solution of 5.0 g (0.015 mol) of product of Example 28 of European Patent Application No. 133,612 published Feb. 27, 1985, and 15 mL of thionyl chloride was refluxed overnight. The excess thionyl chloride was then removed in vacuo and the resulting acid chloride was diluted with 25 mL of methylene chloride and cooled to 0° C. To this stirred solution was added dropwise a mixture of 1.16 g of pyridine and 16 mL of 1.0 M hydrazoic acid in chloroform. After the addition was complete, the reaction mixture was warmed to room temperature for 10 min. Then, 35 mL of methanol was added and the reaction mixture was warmed on a hot plate until gas evolution ceased. This was then diluted with 100 mL of water and extracted with chloroform (3×40 mL). Normal workup afforded 5.6 g (quantitative) of product as an off-white solid. Recrystallization from ethyl acetate/cyclohexane afforded analytically pure material, mp 84°–86° C.

| Elemental Analysis: | C | H | N |
|---|---|---|---|
| Calculated | 45.41 | 4.08 | 7.51 |
| Found | 45.17 | 4.08 | 8.14 |

EXAMPLE 7

3-Pyridinecarboxylic acid, 6-(difluoromethyl)-4-(2-methylpropyl)-5-[(trifluoroacetyl) amino]-2-(trifluoromethyl)-, ethyl ester. To a slurry of 1.08 g (0.027 mol) of 60% sodium hydride and 10 mL of anhydrous tetrahydrofuran was added a solution of 8.0 g (0.023 mol) of product of Example 1 in 10 mL of tetrahydrofuran. This was refluxed for 2 h, then stirred overnight at room temperature. To this was added 5.5 g (0.026 mol) of trifluoroacetic anhydride dropwise. This was stirred for 1 h then poured into 100 mL of 5% hydrochloric acid and extracted with chloroform (3×50 mL). Normal workup afforded 11.0 g of brown solid. Recrystallization from ethyl acetate/cyclohexane afforded 9.53 g (90%) of product as a white solid, mp 102°–104° C.

| Elemental Analysis: | C | H | N |
|---|---|---|---|
| Calculated | 44.05 | 3.70 | 6.42 |
| Found | 44.45 | 3.76 | 6.44 |

EXAMPLE 8

3-Pyridinecarboxylic acid, 5-chloro-6-(difluoromethyl)-4-isobutyl-6-(trifluoromethyl)-,ethyl ester. To a mixture of 2.96 g (0.022 mol) of cupric chloride, 2.26 g (0.018 mol) of t-butyl nitrite and 40 mL of acetonitrile is added dropwise to a solution of 5.0 g (0.015 mol) of product of Example 1 in 10 mL of acetonitrile. This was stirred overnight at room temperature, then poured into 100 mL of 2.5 M hydrochloric acid. The product was extracted into 3×50 mL of ether. Workup as usual afforded 5.26 g of dark brown oil. This was chromatographed on the Prep-500 using 2% ethyl acetate/cyclohexane as elution solvent. Fraction 1 afforded 2.14 g (41%) of product as a colorless oil material; $n_D^{25}$ 1.456

| Elemental Analysis: | C | H | N | Cl |
|---|---|---|---|---|
| Calculated | 6.75 | 4.20 | 3.89 | 9.86 |
| Found | 46.82 | 4.24 | 3.86 | 9.90 |

EXAMPLE 9

3-Pyridinecarboxylic acid, 6-(difluoromethyl)-5-iodo-4-isobutyl-2-(trifluoromethyl)-, ethyl ester. To a 0° C. solution of 4.0 g (0.012 mol) of product of Example 1, 2.16 g (0.012 mol) of 48% fluoroboric acid and 30 mL of acetonitrile was added 1.34 g (0.013 mol) of t-butyl nitrite. This was allowed to stir at 0° C. for 30 min, then it was added to a solution of 30 g potassium iodide in 150 mL of water. After stirring for 30 min, the reaction mixture was extracted with chloroform (4×40 mL). The chloroform extract was washed with 10% sodium thiosulfate (2×50 mL), brine (50 mL) and dried through a cone of sodium sulfate. Concentration in vacuo afforded 4.82 g of orange oil which was chromatographed on silica gel using 2% ethyl acetate/cyclohexane. The first fraction contained 1.98 g (37%) of product as a colorless oil; $n_D^{25}$ 1.493

| Elemental Analysis: | C | H | N |
|---|---|---|---|
| Calculated | 37.27 | 3.35 | 3.10 |
| Found | 37.55 | 3.42 | 3.13 |

The second fraction contained 1.65 g (31%) of product as a light yellow oil; $n_D^{25}$ 1.488.

| Elemental Analysis: | C | H | N |
|---|---|---|---|
| Calculated | 37.27 | 3.35 | 3.10 |
| Found | 37.57 | 3.40 | 3.09 |

EXAMPLE 10

3-Pyridinecarboxylic acid, 5-chloro-6-(difluoromethyl)-4-ethyl-6-(trifluoromethyl)-,ethyl ester. To a slurry of 2.55 g (0.019 mol) of cupric chloride, 2.48 g (0.024 mol) of t-butyl nitrite and 70 mL of anhydrous acetonitrile was added a solution of 5.0 g (0.016 mol) of product of Example 2 in 5 mL acetonitrile. This was stirred at room temperature for 2 h, diluted with 200 mL of 10% hydrochloric acid and extracted into chloroform (3×40 mL). Normal workup afforded an orange oil which was Kugelrohr distilled (120° C. @1.0 torr) to give 4.57 g (86%) of product as a colorless liquid.

| Elemental Analysis: | C | H | N | Cl |
|---|---|---|---|---|
| Calculated | 43.46 | 3.34 | 4.22 | 10.69 |
| Found | 43.44 | 3.41 | 4.30 | 10.81 |

EXAMPLE 11

3-Pyridinecarboxylic acid, 5-chloro-6-(difluoromethyl)-4-ethyl-2-(trifluoromethyl)-,methyl ester. To a solution of 3.23 g (0.024 mol) of cupric chloride, 3.09 g (0.030 mol) of t-butyl nitrite and 65 mL of acetonitrile was added to a solution of 6.0 g of product of Example 5 in 10 mL of acetonitrile. After stirring at room temperature for 3 h, the reaction mixture was poured into 200 mL of 10% hydrochloric acid and extracted with chloroform (3×70 mL). Normal workup afforded 6.32 g of an orange oil which was chromatographed on the Prep-500 using 2% ethyl acetate/cyclohexane. Workup of the first fraction afforded 4.12 g (66%) of product as a white solid. Recrystallization from cyclohexane afforded analytically pure material, mp 62°-62° C.

| Elemental Analysis: | C | H | N | |
|---|---|---|---|---|
| Calculated | 41.59 | 2.86 | 4.41 | 11.16 |
| Found | 41.57 | 2.79 | 4.34 | 11.18 |

Example 12

3-Pyridinecarboxylic acid, 5-bromo-6-(difluoromethyl)-4-ethyl-2-(trifluoromethyl)-,ethyl ester. To a solution of 5.09 g (0.023 mol) of cupric bromide, 2.94 g (0.029 mol) of t-butyl nitrite and 70 mL of anhydrous acetonitrile was added a solution of 6.0 g (0.019 mol) of product of Example 2 in 5 ml acetonitrile. This was stirred at room temperature for 2 h, then poured into 10% hydrochloric acid (200 mL) and extracted with chloroform (3×40 mL). Normal workup afforded 6.95 g of a light yellow oil. Kugelrohr distillation (125° C. @1.0 torr) gave 6.35 g (89%) of product as a white solid. Recrystallization from cyclohexane gave analytically pure material, mp 39°-41° C.

| Elemental Analysis: | C | H | N | Br |
|---|---|---|---|---|
| Calculated | 38.32 | 2.95 | 3.72 | 21.25 |
| Found | 38.47 | 2.99 | 3.77 | 21.40 |

EXAMPLE 13

3-Pyridinecarboxylic acid,5-bromo-6-(difluoromethyl)-4-ethyl-2-(trifluoromethyl)-,methyl ester. To a solution of 5.36 g (0.024 mol) of cupric bromide, 3.09 g (0.030 mol) of t-butyl nitrite and 6.5 mL of acetonitrile was added a solution of 6.0 g (0.020 mol) of product of Example 5 in 10 mL of acetonitrile. After stirring for 3 h at room temperature, the reaction mixture was added to 200 mL of 10% hydrochloric acid and extracted with chloroform. Normal workup afforded 7.05 g of brown oil which was chromatographed on silica gel using 2% ethyl acetate/cyclohexane. Workup of the first fraction afforded 4.83 g (68%) of product as a white solid. Recrystallization from cyclohexane afforded analytically pure material, mp 61°-62° C.

| Elemental Analysis: | C | H | N | Br |
|---|---|---|---|---|
| Calculated | 36.49 | 2.51 | 3.87 | 22.07 |
| Found | 36.56 | 2.55 | 3.86 | 22.16 |

EXAMPLE 14

3-Pyridinecarboxylic acid, 6-(difluoromethyl)-4-ethyl-5-iodo-2-(trifluoromethyl)-,ethyl ester. To a 0° C. solution of 2.0 g (6.40 mmol) of product of Example 2, 1.18 g (6.40 mmol) of 48% fluoroboric acid and 10 mL of acetonitrile was added to 0.72 g of t-butyl nitrite. This solution was stirred at 0° C. for 15 min then was added to a rapidly stirred solution of 12 g of potassium iodide in 100 mL of water. This was stirred for 30 min, then was extracted with chloroform (3×40 mL). The combined chloroform extract was washed with 10% sodium thiosulfate (2×100 mL), brine (50 mL), and dried through a cone of sodium sulfate. Concentration in vacuo afforded an orange oil which was filtered through a short plug of silica gel (5% ethyl acetate/cyclohexane as eluant) to afford 2.10 g (78%) of product as a white solid. Recrystallization from cyclohexane afforded analytically pure material, mp 63°–65° C.

| Elemental Analysis: | C | H | N |
| --- | --- | --- | --- |
| Calculated | 34.06 | 2.62 | 3.31 |
| Found | 34.32 | 2.68 | 3.30 |

EXAMPLE 15

3-Pyridinecarboxylic acid, 6-(difluoromethyl)-4-ethyl-5-iodo-2-(trifluoromethyl)-,methyl ester. To a 0° C. solution of 6.25 g (0.021 mol) of product of Example 5, 3.84 g (0.021 mol) of 48% fluoroboric acid and 55 mL of acetonitrile was slowly added 2.38 g (0.023 mol) of t-butyl nitrite. This was stirred at 0° C. for 30 min, then added to a rapidly stirred solution of 55 g of potassium iodide in 200 mL of water. After 20 min, this was diluted with water (200 mL) and extracted with chloroform (3×50 mL). This was washed with 10% sodium thiosulfate (2×50 mL), brine (100 mL) and dried through sodium sulfate. Concentration in vacuo afforded 7.80 g of brown oil, which was chromatographed on silica gel using 2% ethyl acetate/cyclohexane. Workup of the first fraction afforded 4.58 g (56%) of product as a white solid. Recrystallization from cyclohexane afforded analytically pure material, mp 62°–63° C.

| Elemental Analysis: | C | H | N |
| --- | --- | --- | --- |
| Calculated | 32.30 | 2.22 | 3.42 |
| Found | 32.37 | 2.26 | 3.38 |

EXAMPLE 16

3-Pyridinecarboxylic acid,5-amino-6-(difluoromethyl)-4-propyl-2-(trifluoromethyl)-,ethyl ester. To a stirred slurry of 41.3 g of sodium azide, 75 mL of water and 260 mL of acetone was slowly added a solution of 109 g (0.292 mol) of product of Example 47 of European Patent Application No. 133,612 published Feb. 27, 1985, in 30 mL of acetone. An exothermic reaction took place with vigorous gas evolution. After the reaction mixture cooled to room temperature, it was diluted with water (500 mL) and extracted into CHCls (3×150mL). Normal workup afforded 94.8 g (quantitative) of product as an offwhite solid. Recrystallization from ethyl acetate/cyclohexane gave analytically pure material, mp 73°–75° C.

| Elemental Analysis: | C | H | N |
| --- | --- | --- | --- |
| Calculated | 47.86 | 4.63 | 8.59 |
| Found | 47.79 | 4.66 | 8.59 |

EXAMPLE 17

3-Pyridinecarboxylic acid, 6-(difluoromethyl)-5-[(ethoxymethylene)amino]-4-propyl-2-(trifluoromethyl)-,ethyl ester. A solution of 20.0 g (0.061 mol) of product of Example 16, 22.7 g (0.153 mol) of triethyl orthoformate and 300 mg of p-toluenesulfonic acid was heated at 110° C. with removal of ethanol by distillation. After 4 h, the excess orthoformate was removed in vacuo and the residue was Kugelrohr distilled (140° C. @1 torr) to afford 23.3 g (quantitative) of product as a colorless liquid; $n_D^{25}$ 1 462.

| Elemental Analysis: | C | H | N |
| --- | --- | --- | --- |
| Calculated | 50.26 | 5.01 | 7.33 |
| Found | 50.18 | 5.01 | 7.29 |

EXAMPLE 18

3-Pyridinecarboxylic acid, 5-amino-4-ethyl -6-methyl-2-(trifluoromethyl)-,ethyl ester. A solution of 19.2 g (0.054 mol) of 3-t-butyl 5-ethyl 4-ethyl-2-methyl-6-(trifluoromethyl)-3,5-pyridinedicarboxylate prepared by methods shown in European Patent Application No. 133,612, and 40 mL of 97% formic acid was stirred overnight at 85° C. The reaction mixture was then concentrated in vacuo to give an orange oil which was diluted with 50 mL of thionyl chloride and refluxed for 3 h. The excess thionyl chloride was removed in vacuo and the residue was Kugelrohr distilled to give 13.4 g (78%) of the acid chloride. This was taken up in 5 mL of acetone and added to a stirred slurry of 7.5 g of sodium azide, 13 mL of water and 50 mL of acetone. An exothermic reaction occurred with vigorous gas evolution. After the reaction mixture cooled to room temperature, it was diluted with 200 mL of water and extracted with chloroform (3×75 mL). Normal workup afforded an oily solid which was chromatographed on silica gel using 20% ethyl acetate/cyclohexane to give 6.35 (55%) of product as a white solid. Recrystallization from ethyl acetate/cyclohexane gave analytically pure material, mp 107°–109° C.

| Elemental Analysis: | C | H | N |
| --- | --- | --- | --- |
| Calculated | 52.17 | 5.47 | 10.14 |
| Found | 52.26 | 5.54 | 10.11 |

EXAMPLE 19

3-Pyridinecarboxylic acid, 4-ethyl-6-methyl -5-nitro-2-(trifluoromethyl)-,ethyl ester. To a 55° C. slurry of 7.82 g of sodium perborate (0.051 mol) and 40 mL of glacial acetic acid was added a solution of 3.5 g (0.013 mol) of product of Example 18 in 15 mL of glacial acetic acid. The reaction mixture was maintained at 55° C. for 2 h, then was poured into 150 mL of water and extracted with chloroform (3×40 mL). Workup as usual afforded a dark oil which was Kugelrohr distilled (130° C. @1 torr) to give 1.57 g of product as a light yellow oil. The residue which did not distill was chromatographed on silica gel (1% EtOAc/cyclohexane) to afford an additional 1.00 g of product to give a total of 2.57 g (66%); $n_D^{25}$ 1.465.

| Elemental Analysis: | C | H | N |
|---|---|---|---|
| Calculated | 47.07 | 4.28 | 9.15 |
| Found | 47.01 | 4.29 | 9.23 |

EXAMPLE 20

3-Pyridinecarboxylic acid, 6-(difluoromethyl)-4-ethyl-5-nitro-2-(trifluoromethyl),ethyl ester. To a solution of 4.0 g (0.013 mol) of product of Example 2 in 100 mL of concentrated sulfuric acid at 0° C. was carefully added 10 mL of 90% hydrogen peroxide. This was slowly warmed to room temperature over a 3-hour period and then stirred there overnight. The reaction mixture was diluted with ice (300 g) and extracted with chloroform. Normal workup gave a white solid which was chromatographed on silica gel using 1% ethyl acetate/cyclohexane. Workup of the first fraction gave 2.02 g (46%) of product as a white solid, mp 44°–46° C.

| Elemental Analysis: | C | H | N |
|---|---|---|---|
| Calculated | 42.12 | 3.24 | 8.19 |
| Found | 42.28 | 3.25 | 8.15 |

EXAMPLE 21

3-Pyridinecarboxylic acid, 6-(difluoromethyl)-5-nitro-4-propyl-2-(trifluoromethyl)-,ethyl ester To a 0° C. solution of 15.0 g (0.046 mol) of product of Example 16 and 360 mL of concentrated sulfuric acid was carefully added 36 mL of 90% hydrogen peroxide. This was slowly warmed to room temperature over a 3-hour period and stirred there overnight. The reaction mixture was quenched with ice (300 g) and extracted into chloroform (3×100 mL). Workup as usual gave a white solid which was chromatographed on silica gel using 1% ethyl acetate/cyclohexane. Workup of the first fraction gave 9.35 g (57%) of product as a white solid, mp 63°–65° C.

| Elemental Analysis: | C | H | N |
|---|---|---|---|
| Calculated | 43.83 | 3.68 | 7.86 |
| Found | 43.83 | 3.69 | 7.86 |

EXAMPLE 22

3-Pyridinecarboxylic acid,2-(trifluoromethyl)-4-(2-methylpropyl)-5-nitro-6-(difluoromethyl)-,ethyl ester. To a 0° C. solution 6.0 g (0.018 mol) of product of Example 1 and 135 mL of concentrated sulfuric acid was carefully added 13.5 mL of 90% hydrogen peroxide, dropwise. This was slowly warmed to room temperature over a period of 3 h, then was stirred overnight. To this was added 200 g of ice chips and the resulting aqueous solution was extracted with chloroform (3×75 mL). Workup as usual gave a brown oil which was chromatographed on silica gel (1% ethyl acetate/cyclohexane). Workup gave 3.53 g (54%) of product as a white solid, mp 44°–46° C.

| Elemental Analysis: | C | H | N |
|---|---|---|---|
| Calculated | 45.41 | 4.08 | 7.57 |
| Found | 45.47 | 4.03 | 7.75 |

EXAMPLE 23

3-Pyridinecarboxylic acid, 6-(difluoromethyl)-4-methyl-5-nitro-2-(trifluoromethyl)-,ethyl ester. To a 0° C. solution of 15.0 g (0.050 mol) of product of Example 71 and 360 mL of concentrated sulfuric acid was carefully added 36 mL of 90% hydrogen peroxide dropwise. This was slowly warmed to room temperature over a 3-hour period and allowed to stir there overnight. Then, 300 g of ice chips were added and the product was extracted into chloroform (3×75 mL). Workup as usual afforded an off-white solid which was Kugelrohr distilled (140° C. @1 torr) to give 11.8 g (72%) of product as a white solid, mp 93°–95° C.

| Elemental Analysis: | C | H | N |
|---|---|---|---|
| Calculated | 40.26 | 2.76 | 8.54 |
| Found | 40.43 | 2.75 | 8.33 |

EXAMPLE 24

3-Pyridinecarboxylic acid, 6-(difluoromethyl)-4-ethyl-5-nitro-2-(trifluoromethyl)-,methyl ester. To a 0° C. solution of 5.0 g (0.017 mol) of product of Example 5 and 120 mL of concentrated sulfuric acid was carefully added 12 mL of 90% hydrogen peroxide dropwise. This was stirred at 0° C. for 3 h, then slowly warmed to room temperature and stirred overnight. The reaction mixture was then diluted with 200 g of ice and extracted with chloroform. Workup as usual gave a white solid which was chromatographed on silica gel (1% ethyl acetate/cyclohexane). Workup of the first fraction afforded 25 2.73 g (50%) of product as a white solid, mp 65°–67° C.

| Elemental Analysis: | C | H | N |
|---|---|---|---|
| Calculated | 40.26 | 2.76 | 8.54 |
| Found | 40.30 | 2.76 | 8.54 |

EXAMPLE 25

3-Pyridinecarboxylic acid, 6-(difluoromethyl)-4-ethyl-5-[(trifluoroacetyl)amino]-2-(trifluoromethyl)-,ethyl ester. A solution a 4.0 g (0.16 mol) of product of Example 2, 35 mL of trifluoroacetic anhydride and 20 mL of methylene chloride was stirred at room temperature for 3 h. The reaction mixture was then concentrated in vacuo (50° C. @20 torr) affording 6.19 g (95%) of product as a white solid. Recrystallization from ethyl acetate/cyclohexane gave analytically pure material, mp 98°–100° C.

| Elemental Analysis: | C | H | N |
|---|---|---|---|
| Calculated | 41.19 | 2.96 | 6.86 |
| Found | 41.49 | 3.09 | 6.95 |

EXAMPLE 26

3-Pyridinecarboxylic acid, 6-(difluoromethyl)-4-methyl-5-[(trifluoroacetyl)amino]-2-(trifluoromethyl)-,ethyl ester. A solution of 7.44 g (0.025 mol) of product of Example 71, 20 g of trifluoroacetic anhydride and 20 mL of chloroform was stirred at room temperature for 2 h. The reaction mixture was concentrated in vacuo to afford a white solid which was recrystallized from ethyl acetate/cyclohexane to give 8.5 g (90%) of product, mp 112°–114° C.

| Elemental Analysis: | C | H | N |
|---|---|---|---|
| Calculated | 39.61 | 2.56 | 7.14 |
| Found | 39.55 | 2.58 | 7.11 |

EXAMPLE 27

3-Pyridinecarboxylic acid, 6-(difluoromethyl)-4-ethyl-5-[(pentafluoropropionyl)amino]-2-(trifluoromethyl)-,ethyl ester. A solution of 4.0 g (0.0128 mol) of product of Example 71, 15 mL of dichloromethane and 5.0 g (0.16 mol) of pentafluoropropionic anhydride was stirred at room temperature for 1 day. The reaction mixture was then concentrated in vacuo and Kugelrohr distilled (150° C. @0.5 torr) to give 4.8 g (82%) of product as a white solid, mp 113°–115° C.

| Elemental Analysis: | C | H | N |
|---|---|---|---|
| Calculated | 39.32 | 2.64 | 6.11 |
| Found | 39.72 | 2.68 | 6.17 |

EXAMPLE 28

3-Pyridinecarboxylic acid, 6-(difluoromethyl)-4-ethyl-5-[(pentafluoropropionyl)amino]-2-(trifluoromethyl)-,ethyl ester. A solution of 3.0 g (0.010 mol) of product of Example 5, 9 mL of pentafluoropropionic anhydride and 14 mL of chloroform was stirred at room temperature for 3 h. The reaction mixture was concentrated in vacuo affording a white solid. Recrystallization from ethyl acetate/cyclohexane gave 4.07 g (92%) of product as a white solid, mp 96°–98° C.

| Elemental Analysis: | C | H | N |
|---|---|---|---|
| Calculated | 37.85 | 2.27 | 6.31 |
| Found | 38.10 | 2.41 | 6.50 |

EXAMPLE 29

3-Pyridinecarboxylic acid, 6-(difluoromethyl)-5-(formylamino)-4-methyl-2-(trifluoromethyl) -,ethyl ester. To 43.2 g (0.42 mol) of acetic anhydride at 0° C. was added 24.4 g (0.53 mol) of formic acid. This was warmed to room temperature, then heated at 50° C. for 15 min. This was then immediately cooled to 0° C. and 4.68 g (0.016 mol) of product of Example 71 was added. After stirring at room temperature for 40 min, the reaction mixture was concentrated in vacuo and the resulting solid was recrystallized from ethyl acetate to give 3.51 g (67%) of product as a white solid, mp 151°–152° C.

| Elemental Analysis: | C | H | N |
|---|---|---|---|
| Calculated | 44.18 | 3.40 | 8.59 |
| Found | 44.11 | 3.43 | 8.57 |

EXAMPLE 30

3-Pyridinecarboxylic acid, 5-[(α-chloroacetyl)amino]-6-(difluoromethyl)-4-ethyl-2-(trifluoromethyl)-,ethyl ester. A solution of 4.0 g (0.0128 mol) of product of Example 2, 1.50 g (0.013 mol) of chloroacetyl chloride and 10 mL of acetonitrile was stirred overnight at room temperature. A small amount of starting material remained, as determined by gas chromatography, so another 75 mg of chloroacetyl chloride was added and the reaction was stirred another 4 h. Concentration of the reaction mixture in vacuo gave 5.10 g (quantitative) of product as a white solid. Recrystallization from ethyl acetate/cyclohexane gave analytically pure material, mp 104°–106° C.

| Elemental Analysis: | C | H | N | Cl |
|---|---|---|---|---|
| Calculated | 43.26 | 3.63 | 7.21 | 9.12 |
| Found | 43.40 | 3.67 | 7.26 | 9.10 |

EXAMPLE 31

3-Pyridinecarboxylic acid, 5-[(α,α-dichloropropionyl)amino]-6-(difluoromethyl)-4-ethyl-2-(trifluoromethyl)-,ethyl ester. A solution of 4.0 g (0.0128 mol) of product of Example 2, 2.42 g (0.015 mol) of 2,2-dichloropropionyl chloride, 1.18 g (0.015 mol) of pyridine and 10 mL of acetonitrile was refluxed for 24 h. The reaction mixture was then poured into 50 mL of 1M hydrochloric acid and extracted with chloroform. Normal workup afforded a dark solid which was Kugelrohr distilled (160° C. @1 torr) to give 4.52 g (81%) of product as an off-white solid. Recrystallization from ethyl acetate/cyclohexane gave analytically pure material, mp 145°–146° C.

| Elemental Analysis: | C | H | N | Cl |
|---|---|---|---|---|
| Calculated | 41.21 | 3.46 | 6.41 | 16.22 |
| Found | 41.26 | 3.46 | 6.37 | 16.15 |

EXAMPLE 32

3-Pyridinecarboxylic acid, 6-(difluoromethyl)-5-[(ethoxymethylene)amino]-4-methyl-2-(trifluoromethyl)-,ethyl ester. A solution of 5.0 g (0.0168 mol) of product of Example 71, 7.0 g of triethyl orthoformate and 100 mg of p-toluenesulfonic acid was heated at 110° C. with removal of ethanol by distillation. After 3 h, the reaction mixture was concentrated in vacuo and the residue was Kugelrohr distilled (140° C. @1 torr) to afford 5.10 g (86%) of product as a colorless liquid; $n_D^{25}$ 1.465.

| Elemental Analysis: | C | H | N |
|---|---|---|---|
| Calculated | 47.46 | 4.27 | 7.91 |
| Found | 47.47 | 4.29 | 7.89 |

EXAMPLE 33

3-Pyridinecarboxylic acid, 6-(difluoromethyl)-5-[(ethoxymethylene)amino]-4-ethyl-2-(trifluoromethyl)-,ethyl ester. A solution of 4.0 g (0.013 mol) of product of Example 2, 5.7 g (0.038 mol) of triethyl orthoformate and 70 mg of p-toluenesulfonic acid was stirred at 100° C. for 2 h with removal of the ethanol formed by distillation. The reaction mixture was concentrated in vacuo and the residue was Kugelrohr distilled (150° C. @1 torr) to give 3.86 g (82%) of product as a colorless oil; $n_D^{25}$.

| Elemental Analysis: | C | H | N |
| --- | --- | --- | --- |
| Calculated | 48.92 | 4.65 | 7.61 |
| Found | 48.78 | 4.62 | 7.51 |

EXAMPLE 34

3-Pyridinecarboxylic acid, 6-(difluorofluoromethyl)-,ethyl ester. A solution of 4.0 g (0.013 mol) of product of Example 2, 4.0 g (0.038 mol) of trimethyl orthoformate and 70 mg of p-toluenesulfonic acid was heated at 100° C. for 2 h, removing the methanol formed by distillation. The reaction mixture was concentrated in vacuo and the residue was Kugelrohr distilled (150° C. @1 torr) to afford 3.90 g (86%) of product a colorless oil; $n_D^{25}$ 1 463.

| Elemental Analysis: | C | H | N |
| --- | --- | --- | --- |
| Calculated | 47.46 | 4.27 | 7.91 |
| Found | 47.67 | 4.36 | 7.86 |

EXAMPLE 35

5 3-Pyridinecarboxylic acid, 6-(difluoromethyl)-5-[(ethoxymethylene)amino]-4-(2-methylpropyl) -2-(trifluoromethyl)-,ethyl ester. A solution of 3.75 g (0.011 mol) of product of Example 1, 4.90 (0.033 mol) of triethyl orthoformate and 70 mg of p-toluenesulfonic acid was heated at 100° C. for 2 h, removing the ethanol which formed by distillation. The reaction mixture was concentrated in vacuo and the residue was Kugelrohr distilled (150° C. @1 torr) to give 3.83 g (88%) of product as a colorless liquid; $n_D^{25}$ 1.464.

| Elemental Analysis: | C | H | N |
| --- | --- | --- | --- |
| Calculated | 51.52 | 5.34 | 7.07 |
| Found | 51.80 | 5.48 | 7.03 |

EXAMPLE 36

3-Pyridinecarboxylio acid, 6-(difluoromethyl)-5-[{methoxymethylene)amino]-4-methyl-2-(trifluoromethyl)-,ethyl ester. A solution of 4.0 g (0.013 mol) of product of Example 71, 4.2 g (0.040 mol) of trimethyl orthoformate and 70 mg of p-toluenesulfonic acid was heated at 100° C. for 2 h, removing the methanol which formed by distillation. The reaction mixture was concentrated in vacuo and the residue was Kugelrohr distilled (150° C. @1 torr) to give 4.01 g (88%) of product as a light yellow oil; $n_D^{25}$ 1.463.

| Elemental Analysis: | C | H | N |
| --- | --- | --- | --- |
| Calculated | 45.89 | 3.85 | 8.23 |
| Found | 45.89 | 3.94 | 8.03 |

EXAMPLE 37

3-Pyridinecarboxylic acid, 6-(difluoromethyl)-4-ethyl-5-[(methoxymethylene)amino]-2-(trifluoromethyl)-,methyl ester. A solution of 3.50 g (0.012 mol) of product of Example 5, 3.82 g (0.036 mol) of trimethyl orthoformate and 30 mg of p-toluenesulfonic acid was stirred at reflux for 2 h, then concentrated in vacuo. The residue was Kugelrohr distilled (145° C. @1 torr) to give 3.47 g (84%) of product as a colorless oil which slowly solidified, mp 29°–30° C.

| Elemental Analysis: | C | H | N |
| --- | --- | --- | --- |
| Calculated | 45.89 | 3.85 | 8.23 |
| Found | 46.04 | 3.82 | 8.11 |

EXAMPLE 38

3-Pyridinecarboxylic acid, 6-(difluoromethyl)-5-[(methoxymethylene)amino]-4-propyl-2-(trifluoromethyl)-,ethyl ester. A solution of 3.0 g (0.0092 mol) of product of Example 16, 10 mL of trimethyl orthoformate and 70 mg of p-toluenesulfonic acid was stirred at 100° C. for 2 h. The reaction mixture was concentrated in vacuo and the residue was Kugelrohr distilled (135° C. ° C. @1 torr) to give 3.13 g (92%) of product as a colorless oil; $n_D^{25}$ 1 465.

| Elemental Analysis: | C | H | N |
| --- | --- | --- | --- |
| Calculated | 48.92 | 4.65 | 7.61 |
| Found | 48.66 | 4.57 | 7.33 |

EXAMPLE 39

3-Pyridinecarboxylic acid, 6-(difluoromethyl)-5-[(methoxymethylene)amino]-4-(2-methylpropyl) -2-(trifluoromethyl)-,ethyl ester. A solution of 4.10 g (0.012 mol) of product of Example 1, 7 mL of trimethyl orthoformate and 70 mg of p-toluenesulfonic acid was stirred overnight at 100° C. The reaction mixture was concentrated in vacuo and the residue was Kugelrohr distilled (150° C. @1 torr) to give 4.07 g (89%) of product as a colorless oil; $n_D^{25}$ 1 457.

| Elemental Analysis: | C | H | N |
| --- | --- | --- | --- |
| Calculated | 50.26 | 5.01 | 7.33 |
| Found | 50.16 | 5.19 | 7.01 |

EXAMPLE 40

3-Pyridinecarboxylic acid, 6-(difluoromethyl)-4-ethyl-5-[(methoxymethylene)amino]-2-(trifluoromethyl)-,methyl ester. A solution of 4.0 g (0.013 mol) of product of Example 1, 10 mL of triethyl orthoformate and 70 mg of p-toluenesulfonic acid was heated at 100° C. for 3 h. The reaction mixture was concentrated in vacuo and the residue was Kugelrohr distilled (150° C. ° C. @1 torr) to give 4.18 g (88%) of product as a colorless oil; $n_D^{25}$ 1.463.

| Elemental Analysis: | C | H | N |
|---|---|---|---|
| Calculated | 47.46 | 4.27 | 7.91 |
| Found | 47.41 | 4.29 | 7.80 |

EXAMPLE 41

3-Pyridinecarboxylic acid, 6-(difluoromethyl)-5-{[(2-methylpropoxy)methylene]amino}-4-propyl-2-(trifluoromethyl)-,ethyl ester. A solution of 4.0 g (.012 mol) of product of Example 16, 10 mL of tri-i-butyl orthoformate and 70 mg of p-toluenesulfonic acid was heated at 110° C. for 16 h. The reaction mixture was concentrated in vacuo and the residue was Kugelrohr distilled (150° C. ° C. @1 torr) to afford 4.6 g (81%) of product as a colorless oil; $n_D^{25}$ 1.503.

| Elemental Analysis: | C | H | N |
|---|---|---|---|
| Calculated | 52.68 | 5.65 | 6.83 |
| Found | 52.65 | 5.69 | 6.82 |

EXAMPLE 42

3-Pyridinecarboxylic acid, 5-(n-butoxymethylene)amino]-6-(difluoromethyl)-4-ethyl-2-(trifluoromethyl)-,ethyl ester. A solution of 8.7 g of tri-n-butyl orthoformate, 4.0 g (0.013 mol) of product of Example 2 and 70 mg of p-toluenesulfonic acid was heated at 110° C. for 18 h. The reaction was concentrated in vacuo and the residue was Kugelrohr distilled (150° C. ° C. @1 torr) to give a yellow oil. Chromatography on silica gel (2% ethyl acetate/cyclohexane) afforded 1.98 g (39%) of product as a colorless oil; $n_D^{25}$ 1.500.

| Elemental Analysis: | C | H | N |
|---|---|---|---|
| Calculated | 51.52 | 5.34 | 7.07 |
| Found | 51.76 | 5.42 | 7.00 |

EXAMPLE 43

3-Pyridinecarboxylic acid, 6-(difluoromethyl)-4-ethyl-5-[(n-propoxymethylene)amino]-2-(trifluoromethyl)-,ethyl ester. A solution of 5.0 g (0.016 mol) of product of Example 2, 10 mL of tri-n-propyl orthoformate and 70 mg of p-toluenesulfonic acid was heated at 110° C. for 1 h. The reaction mixture was concentrated in vacuo and the residue was Kugelrohr distilled (140° C. ° C. @1 torr) to give 4.25 g (69%) of product as a light yellow oil; $n_D^{25}$ 1.461.

| Elemental Analysis: | C | H | N |
|---|---|---|---|
| Calculated | 50.26 | 5.01 | 7.33 |
| Found | 50.24 | 5.02 | 7.30 |

EXAMPLE 44

3-Pyridinecarboxylic acid, 6-(difluoromethyl)-4-ethyl-5-{[(2-methylpropoxy)methylene]amino }-2-(trifluoromethyl)-,ethyl ester. A solution of 4.0 g (0.013 mol) of product of Example 2, 10 mL of triisobutyl orthoformate and 70 mg of p-toluenesulfonic acid was heated to 110° C. for 18 h. The reaction mixture was concentrated in vacuo and the residue was Kugelrohr distilled (140° C. ° C. @1 torr) to afford 3.8 g (75%) of product as a light yellow oil, which slowly crystallized, mp 34°-34° C.

| Elemental Analysis: | C | H | N |
|---|---|---|---|
| Calculated | 51.51 | 5.34 | 7.07 |
| Found | 51.37 | 5.35 | 7.01 |

EXAMPLE 45

3-Pyridinecarboxylic acid, 6-(difluoromethyl)-5-{[(N,N-dimethylamino)methylene]amino}-4-methyl-2-(trifluoromethyl)-,ethyl ester. A slurry of 5.0 g (0.168 mol) of product of Example 71, 4.0 g (0.34 mol) of dimethylformamide dimethylacetal and 100 mg of p-toluenesulfonic acid was heated at reflux for 1 h. The reaction mixture was concentrated in vacuo and Kugelrohr distilled (150° C. ° C. @1 torr) to give 5.20 g (88%) of product as a white solid, mp 70°-71° C.

| Elemental Analysis: | C | H | N |
|---|---|---|---|
| Calculated | 47.50 | 4.57 | 11.89 |
| Found | 47.61 | 4.43 | 11.64 |

EXAMPLE 46

3-Pyridinecarboxylic acid, 5-[(1-chloro -2,2,2-trifluoroethylidene)amino]-6-(difluoromethyl)-4-methyl-2-(trifluoromethyl)-,ethyl ester. A mixture of 4.0 g (0.010 mol) of product of Example 26 and 2.11 g (0.010 mol) of phosphorous pentachloride was heated to 140° C. and stirred there for 16 h. The reaction mixture was concentrated in vacuo and the residue was Kugelrohr distilled (130° C.° C. @1 torr) to give 3.24 g of product as a colorless oil; $n_D^{25}$ 1 435.

| Elemental Analysis: | C | H | N | Cl |
|---|---|---|---|---|
| Calculated | 37.84 | 2.20 | 6.79 | 8.59 |
| Found | 38.15 | 2.26 | 6.82 | 8.63 |

EXAMPLE 47

3-Pyridinecarboxylic acid, 5-[(1-chloro-2,2,2-trifluoroethylidene)amino]-6-(difluoromethyl) -4-ethyl-2-(trifluoromethyl)-,ethyl ester. A mixture of 33.5 g (0.082 mol) of product of Example 25 and 17.08 g (0.082 mol) of phosphorous pentachloride was heated at 140° C. for 18 h. The reaction mixture was concentrated in vacuo and the residue was Kugelrohr distilled (150° C. @1 torr) to give 31.7 g (91%) of product as a colorless oil; $n_D^{25}$ 1.436

| Elemental Analysis: | C | H | N | Cl |
|---|---|---|---|---|
| Calculated | 39.41 | 2.60 | 6.57 | 8.31 |
| Found | 39.81 | 2.65 | 6.59 | 8.35 |

EXAMPLE 48

3-Pyridinecarboxylic acid, 6-(difluoromethyl)-5-[(1-ethoxy-2,2,2-trifluoroethylidene)amino]-4-ethyl-2-(trifluoromethyl)-,ethyl ester. To an ethanolic sodium ethoxide solution, prepared from 0.25 g (0.011 mol) of sodium metal and 5 mL of absolute ethanol, was added a solution of 4.0 g (0.0094 mol) of product of Example 47 in 5 mL of ethanol. A white precipitate formed immediately. After stirring for 15 min the reaction mixture was poured into water and extracted with chloroform. Workup gave a light yellow oil which was Kugelrohr distilled (130° C. ° C. @1 torr) to give 3.67 (89%) of product as a colorless oil; $n_D^{25}$ 1.440.

| Elemental Analysis: | C | H | N |
|---|---|---|---|
| Calculated | 44.05 | 3.70 | 6.42 |
| Found | 44.46 | 3.76 | 6.48 |

EXAMPLE 49

3-Pyridinecarboxylic acid, 6-(difluoromethyl)-4-ethyl-5-[(1-methoxy-2,2, 2-trifluoroethylidine)amino-2-(trifluoromethyl)-,ethyl ester. To a methanolic sodium methoxide solution, prepared from 0.23 g (0.010 mol) of sodium metal and 4 mL of methanol was added a solution of 4.0 g (0.0094 mol) of product of Example 47 in 5 mL of methanol. A white precipitate formed immediately. After 15 min, the reaction mixture was poured into water and extracted with chloroform. Workup as usual gave a yellow oil which was Kugelrohr distilled (130° C. @1 torr) to give 3.63 g (91%) of product as a colorless oil which slowly solidified, mp 49°–51° C.

| Elemental Analysis: | C | H | N |
|---|---|---|---|
| Calculated | 42.67 | 3.34 | 6.63 |
| Found | 43.03 | 3.39 | 6.65 |

EXAMPLE 50

3-Pyridinecarboxylic acid, 6-(difluoromethyl)-4-ethyl-5-{[1-(ethylthio)-2,2,2-trifluoroethylidine]amino}-2-(trifluoromethyl)-,ethyl ester. To a slurry of 0.38 g (0.0094 mol) of 60% sodium hydride in 10 mL of anhydrous tetrahydrofuran under a nitrogen atmosphere was added 0.59 g (0.0094 mol) of ethanethiol. After gas evolution ceased, a solution of 4.0 g (0.0094 mol) of product of Example 47, 5 mL of tetrahydrofuran was added dropwise. After 15 min, the reaction mixture was poured into water and extracted with chloroform. Workup as usual gave a yellow oil which was Kugelrohr distilled (135° C. @1 torr) to give 3.87 g (91%) of product as a colorless liquid; $n_D^{25}$ 1.464.

| Elemental Analysis: | C | H | N | S |
|---|---|---|---|---|
| Calculated | 42.48 | 3.57 | 6.19 | 7.09 |
| Found | 42.86 | 3.64 | 6.24 | 7.24 |

EXAMPLE 51

3-PyridinecarboxYlic acid,5-{[1-(diethoxyphosphinyl)-2,2,2-trifluoroethylidene]amino}-6-(difluoromethyl) -4-ethyl-2-(trifluoromethyl)-,ethyl ester. A mixture of 2.5 g (0.0059 mol) of product of Example 47 and 0.98 g of triethylphosphite was heated at 160° C. for 30 min. The reaction mixture was then cooled to room temperature where solidification occurred. Trituration of this solid with cyclohexane gave 3.03 g (quantitative) of product as a light yellow solid, mp 73°–75° C.

| Elemental Analysis: | C | H | N |
|---|---|---|---|
| Calculated | 40.92 | 4.01 | 5.30 |
| Found | 40.72 | 4.00 | 5.19 |

EXAMPLE 52

3-Pyridinecarboxylic acid, 6-(difluoromethyl)-4-ethyl-2-(trifluoromethyl)-5-[5-(trifluoromethyl)-1H-tetrazol-1-yl]-,ethyl ester. To a solution of 4.0 g (0.0094 mol) of product of Example 47 and 20 mL of tetrahydrofuran was added 0.65 g (0.01 mol) of sodium azide. This was stirred at room temperature and 4 mL of water was added. The reaction mixture became warm immediately. After 5 min, the reaction mixture was diluted with water (25 mL) and extracted with chloroform (3×20 mL). Workup as usual afforded a thick oil which was Kugelrohr distilled (150° C. ° C. @1 torr) to give 3.83 g (94%) of product as a light yellow oil; $n_D^{25}$ 1.444.

| Elemental Analysis: | C | H | N |
|---|---|---|---|
| Calculated | 38.81 | 2.56 | 16.16 |
| Found | 39.12 | 2.68 | 15.92 |

EXAMPLE 53

3-Pyridinecarboxylic acid, 6-(difluoromethyl)-4-ethyl-2-(trifluoromethyl)]-5-{[1-(trifluoromethyl) ethylidene]amino}-,ethyl ester. To a solution of 2.3 g (0.0054 mol) of product of Example 47 in 5 mL of anhydrous tetrahydrofuran at 0° C. under a dry nitrogen atmosphere was added dropwise 1.7 mL (0.0054 mol) of 3.2 M methyl magnesium bromide in ether. This was stirred at 0° C. for 30 min, then was poured into 10 mL of saturated ammonium chloride. The reaction mixture was suction filtered and the filtrate was extracted with ether (3×25 mL). Workup as usual gave an oil which was chromatographed on silica gel using 5% ethyl acetate/cyclohexane. Workup of the first fraction afforded 1.0 g (46%) of product as a colorless oil; $n_D^{25}$ 1.500.

| Elemental Analysis: | C | H | N |
|---|---|---|---|
| Calculated | 44.35 | 3.47 | 6.89 |
| Found | 43.35 | 3.40 | 6.70 |

EXAMPLE 54

3-Pyridinecarboxylic acid, 6-(difluoromethyl)-4-ethyl-5-isocyanato-2-(trifluoromethyl)-, ethyl ester. The product of Example 46 (50.4 g, 0.14 mol) of European Patent Application No. 133,612 published Feb. 27, 1985, was added to 17.3 g of azidotrimethyl silane (0.15 mol) and 100 mL of carbon tetrachloride and heated at reflux until gas evolution ceased (~4 h). The reaction mixture was concentrated in vacuo and the residue was Kugelrohr distilled (140° C. @1 torr) to give 35.2 g (74%) of product as a light yellow oil; $n_D^{25}$ 1 457.

| Elemental Analysis: | C | H | N |
|---|---|---|---|
| Calculated | 46.16 | 3.28 | 8.28 |
| Found | 45.88 | 3.40 | 8.03 |

EXAMPLE 55

3-Pyridinecarboxylic acid, 6-(difluoromethyl)-4-ethyl-5-isocyanato-2-(trifluoromethyl)-, methyl ester. Methyl 5-chlorocarbonyl-6-(difluoromethyl)-4-ethyl-2-(trifluoromethyl)-3-pyridinecarboxylate (84.1 g, 0.243 mol) was added to 150 mL of carbon tetrachloride and 30 g (0.26 mol) of azidotrimethyl silane and stirred overnight at 55° C. The reaction mixture was concentrated in vacuo and the residue was Kugelrohr distilled to give 57.3 g (72%) of product as a white solid, mp 55°-57° C.

| Elemental Analysis: | C | H | N |
|---|---|---|---|
| Calculated | 44.46 | 2.80 | 8.64 |
| Found | 44.32 | 2.94 | 8.77 |

EXAMPLE 56

3-Pyridinecarboxylic acid, 6-(difluoromethyl)-5-isocyanato-4-(2-methylpropyl)-2-(trifluoromethyl)-,ethyl ester. Ethyl 5-chlorocarbonyl-4-(2-methylpropyl)-2-(trifluoromethyl)-3-pyridinecarboxylate (64.1 g, 0.165 mol) was added to 21.06 (0.182 mol) of azidotrimethyl silane and 120 mL of carbon tetrachloride and heated at reflux for 4h, at which time, gas evolution ceased. The reaction mixture was concentrated in vacuo and the residue was Kugelrohr distilled (100° C. @1 torr) to give 29.4 g (65%) of product as a light yellow oil; $n_D^{25}$ 1.455.

| Elemental Analysis: | C | H | N |
|---|---|---|---|
| Calculated | 49.19 | 4.13 | 7.65 |
| Found | 48.95 | 4.02 | 7.77 |

EXAMPLE 57

3-PYridinecarboxylic acid, 6-(difluoromethyl)-4-ethyl-5-{[(ethylthio)carbonyl]amino}-2-(trifluoromethyl)-,ethyl ester. To a solution of 4.5 g (0.013 mol) of product of Example 54 and 20 mL of methylene chloride was added 15 mL of ethanethiol. To this was added 30 mg of potassium t-butoxide causing an exotherm. The reaction mixture was allowed to stir overnight then was concentrated in vacuo affording a light yellow solid. Recrystallization from ethyl acetate/cyclohexane gave 4.63 g (90%) of product as a white solid, mp 124°-126° C.

| Elemental Analysis: | C | H | N | S |
|---|---|---|---|---|
| Calculated | 45.00 | 4.28 | 7.00 | 8.01 |
| Found | 44.73 | 4.14 | 6.80 | 7.83 |

EXAMPLE 58

3-Pyridinecarboxylic acid, 6-(difluoromethyl)-4-ethyl-5-{[(ethylthio)carbonyl]amino}-2-(trifluoromethyl)-,methyl ester. To a slurry of 0.49 g (0.012 mol) of 60% sodium hydride in 10 mL of anhydrous tetrahydrofuran was added a solution of 4.0 g (0.012 mol) of product of Example 55 in 25 mL of anhydrous tetrahydrofuran. This was stirred at room temperature for 1 h then 50 mL of water was added and the product was extracted into ethyl acetate (3×25 mL). Workup as usual gave 3.95 g (83%) of product as a white solid, mp 143°-145° C.

| Elemental Analysis: | C | H | N | S |
|---|---|---|---|---|
| Calculated | 43.52 | 3.91 | 7.25 | 8.30 |
| Found | 43.42 | 3.97 | 7.21 | 8.38 |

EXAMPLE 59

3-Pyridinecarboxylic acid, 6-(difluoromethyl)-4-ethyl-5-{[(methylthio)carbonyl]amino}-2-(trifluoromethyl)-,methyl ester. A solution of 15.0 g (0.046 mol) of product of Example 55 and 50 mL of tetrahydrofuran was cooled to 0° C. and 10 g of methanethiol was added. To this mixture was added 100 mg of potassium t-butoxide. The reaction mixture was slowly warmed to room temperature and stirred overnight. The reaction mixture was concentrated in vacuo and the residue taken up in chloroform (100 mL). Workup as usual afforded 15.21 g (89%) of product as a white solid. Recrystallization from ethyl acetate/cyclohexane afforded analytically pure material, mp 134°-135° C.

| Elemental Analysis: | C | H | N | S |
|---|---|---|---|---|
| Calculated | 41.94 | 3.52 | 7.52 | 8.61 |
| Found | 42.01 | 3.53 | 7.57 | 8.57 |

EXAMPLE 60

3-Pyridinecarboxylic acid, 6-(difluoromethyl)-5-{[(ethylthio)carbonyl]amino}-4-(2-methylpropyl)-2-(trifluoromethyl)-,ethyl ester. To a solution of 3.50 g (0.0095 mol) of product of Example 56, 0.93 g (0.015 mol) of ethanethiol and 20 mL of tetrahydrofuran was added 15 mg of potassium t-butoxide. This was stirred for 2 h at room temperature, then was concentrated in vacuo. This solid was dissolved in 75 mL of chloroform and worked up as usual to give 3.54 g (86%) of product as a white solid. Recrystallization from ethyl acetate/cyclohexane afforded analytically pure material, mp 113°-114° C.

| Elemental Analysis: | C | H | N | S |
|---|---|---|---|---|
| Calculated | 47.66 | 4.94 | 6.54 | 7.48 |
| Found | 47.65 | 4.96 | 6.52 | 7.56 |

EXAMPLE 61

3-Pyridinecarboxylic acid, 6-(difluoromethyl)-5-[(ethoxycarbonyl)amino]-4-ethyl-2-(trifluoromethyl)-,methyl ester. A solution of 4.1 g (0.013 mol) of product of Example 55, 25 mL of chloroform and 25 mL of ethanol was stirred at reflux for 15 min. The reaction mixture was concentrated in vacuo to give 4.53 g (97%) of product as a white solid. Recrystallization from ethyl acetate/cyclohexane afforded analytically pure material, mp 100°-101° C.

| Elemental Analysis: | C | H | N |
|---|---|---|---|
| Calculated | 45.41 | 4.08 | 7.75 |
| Found | 45.31 | 4.11 | 7.63 |

EXAMPLE 62

3-Pyridinecarboxylic acid, 6-(difluoro-2-(trifluoromethyl)-,methyl ester. A solution of 4.0 g (.012 mol) of product of Example 55, 25 mL of chloroform and 25 mL of 2-propanol was refluxed for 15 min. The reaction mixture was concentrated in vacuo to give 4.63 g (85%) of product as a white solid. Recrystallization from ethyl acetate/cyclohexane afforded analytically pure material, mp 130°–132° C.

| Elemental Analysis: | C | H | N |
|---|---|---|---|
| Calculated | 46.88 | 4.46 | 7.29 |
| Found | 46.67 | 4.47 | 7.37 |

EXAMPLE 63

3-Pyridinecarboxylic acid, 6-(difluoromethyl)-4-ethyl-5-(1-methylethylthio)carbonyl]amino}-2-(trifluoromethyl)-,methyl ester. To a solution of 4.0 g (0.012 mol) of product of Example 55, 5.0 g (0.066 mol) of 2-propanethiol and 20 mL of tetrahydrofuan was added 20 mg of potassium t-butoxide. The reaction mixture was stirred at room temperature for 2 hours then concentrated in vacuo to give a white solid. Recrystallization from ethyl acetate/cyclohexane afforded 4.37 (89%) of product as a white solid, mp 139°–140° C.

| Elemental Analysis: | C | H | N | S |
|---|---|---|---|---|
| Calculated | 45.00 | 4.28 | 7.00 | 8.01 |
| Found | 45.04 | 4.30 | 7.00 | 8.06 |

EXAMPLE 64

3-Pyridinecarboxylic acid, 6-(difluoromethyl)-5-([(1,1-dimethylethyl)thio]carbonyl}amino)-4-ethyl-2-(trifluoromethyl)-,methyl ester. A solution of 3.60 g (0.011 mol) of product of Example 55, 20 mL of chloroform and 20 mL of t-butanol was stirred at reflux for 15 min. The reaction mixture was concentrated in vacuo and the resulting solid was recrystallized from ethyl acetate/cyclohexane to give 4.01 g (91%) of product as a white solid, mp 99°–100° C.

| Elemental Analysis: | C | H | N |
|---|---|---|---|
| Calculated | 48.25 | 4.81 | 7.03 |
| Found | 48.31 | 4.93 | 7.00 |

EXAMPLE 65

3-Pyridinecarboxylic acid, 6-(difluoromethyl)-4-ethyl-5-[(methoxycarbonyl)amino]-2-(trifluoromethyl)-,methyl ester. A solution of 3.0 g (0.0093 mol) of product of Example 55, 20 mL of chloroform and 20 mL of methanol was stirred at reflux for 15 min, then concentrated in vacuo. The resulting solid was recrystallized from ethyl acetate/cyclohexane to give 3.08 g (93%) of product as a white solid, mp 111°–113° C.

| Elemental Analysis: | C | H | N |
|---|---|---|---|
| Calculated | 43.83 | 3.68 | 7.86 |
| Found | 44.21 | 3.75 | 8.12 |

EXAMPLE 66

3-Pyridinecarboxylic acid, 6-(difluoromethyl)-5-{[(dimethylamino)carbonyl]amino}-4-ethyl-2-(trifluoromethyl)-,methyl ester. To a solution of 3.0 g (0.0093 mol) of product of Example 55, 20 mL of dioxane was added 10 mL of 26% aqueous dimethylamine. This was stirred at 60° C. for 10 min, then was poured into 100 mL of water and extracted with chloroform (3×40 mL). Workup as usual afforded 3.06 g (89%) of product as a white solid. Recrystallization from ethyl acetate/cyclohexane gave analytically pure material, mp 177°–178° C.

| Elemental Analysis: | C | H | N |
|---|---|---|---|
| Calculated | 45.53 | 4.37 | 11.38 |
| Found | 45.64 | 4.41 | 11.29 |

EXAMPLE 67

3-Pyridinecarboxylic acid, 6-(difluoromethyl)-4-ethyl-5-{[(N-methylamino)carbonyl]amino}-2-(trifluoromethyl)-,methyl ester. To a solution of 3.57 g (0.011 mol) of product of Example 55 and 20 mL of dioxane was added 7 mL of 40% aqueous methylamine. A white preciptiate formed immediately. This was stirred at 50° C. for 10 min, cooled to room temperature, and suction filtered. Air drying afforded 3.56 g (91%) of product as a white solid, mp 202°–203° C.

| Elemental Analysis: | C | H | N |
|---|---|---|---|
| Calculated | 43.95 | 3.97 | 11.83 |
| Found | 43.82 | 4.02 | 11.78 |

EXAMPLE 68

3-Pyridinecarboxylic acid, 6-(difluoromethyl)-4-ethyl-5-(4,5-dihydro-5-oxo-1H-tetrazol -1-yl)-2-(trifluoromethyl)-,ethyl ester. A solution of 4.0 g (0.012 mol) of product of Example 54 and 2.72 g (0.024 mol) of azidotrimethyl silane was refluxed for 1.5 days then was concentrated in vacuo. The reaction mixture slowly solidified over a period of 3 days. Trituration with ethyl acetate/cyclohexane gave 2.20 g (49%) of product as a white solid, mp 139°–141° C.

| Elemental Analysis: | C | H | N |
|---|---|---|---|
| Calculated | 40.95 | 3.17 | 18.37 |
| Found | 40.88 | 3.21 | 18.33 |

EXAMPLE 69

3-Pyridinecarboxylic acid, 5-{(2-chloroethoxy)carbonyl]amino}-6-(difluoromethyl)-4-ethyl-2-(trifluoromethyl)-,ethyl ester. A solution of 4.0 g (0.12 mol) of product of Example 54, 9 mL of chloroform and 9 mL of 2-chloroethanol was heated at reflux for 1.5 days. The reaction mixture was concentrated in vacuo and the residue slowly solidified over 3 days. Trituration with ethyl acetate/cyclohexane gave 3.27 g (66%) of product as a white solid, mp 102°–103° C.

| Elemental Analysis: | C | H | N | Cl |
|---|---|---|---|---|
| Calculated | 43.02 | 3.85 | 6.69 | 8.47 |

-continued

| Elemental Analysis: | C | H | N | Cl |
|---|---|---|---|---|
| Found | 43.21 | 3.87 | 6.68 | 8.50 |

EXAMPLE 70

3-Pyridinecarboxylic acid,5-{[(diethoxyphosphinyl)-carbonyl]amino}-6-(difluoromethyl)-4-ethyl -2-(trifluoromethyl)-,methyl ester. To a solution of 4.0 g (0.012 mol) of product of Example 55 and 3 drops of triethylamine in 20 mL of toluene was added 1.70 g of diethyl phosphite. This was heated at 80° C. for 1.5 day, then was concentrated in vacuo. The residue was dissolved in chloroform, washed with water (20 mL), 1 M hydrochloric acid (20 mL) and brine (20 mL). Workup as usual afforded 5.1 g (90%) of product as a white solid, mp 91°–94° C.

| Elemental Analysis: | C | H | N |
|---|---|---|---|
| Calculated | 41.57 | 4.36 | 6.06 |
| Found | 41.24 | 4.28 | 6.29 |

EXAMPLE 71

3-Pyridinecarboxylic acid,5-amino-6-(difluoromethyl)-4-methyl-2-(trifluoromethyl)-,ethyl ester. To a slurry of 50 g of sodium azide, 90 mL of water and 315 mL of acetone was added 0.474 mol of ethyl 5-chlorocarbonyl-6-(difluoromethyl)-4-methyl-2-(trifluoromethyl)-3-pyridinecarboxylate in 35 mL of acetone with rapid stirring. An exothermic reaction resulted with vigorous gas evolution. After the reaction mixture cooled to room temperature, it was diluted with 200 mL of water and extracted with chloroform. Normal workup afforded 86.3 g (82%) of product as a white solid. Recrystallization from ethyl acetate/cyclohexane afforded analytically pure material, mp 71°–72° C.

| Elemental Analysis: | C | H | N |
|---|---|---|---|
| Calculated | 44.30 | 3.72 | 9.39 |
| Found | 44.30 | 3.73 | 9.40 |

EXAMPLE 72

3-Pyridinecarboxylic acid,5-amino-6-(difluoromethyl)-4-(1-methylethyl)-2-(trifluoromethyl)-, ethyl ester. To a rapidly-stirred solution of 21 g of sodium azide, 35 mL of water and 140 mL of acetone was added a solution of 0.096 mol of product of Example 44 of European Patent Application No. 133,612 published Feb. 27, 1985, in 20 mL of acetone. An exothermic reaction followed with gas evolution. After the reaction mixture cooled to room temperature, it was diluted with water (300 mL) and extracted with chloroform (3×100 mL). Normal workup afforded 28.4 g (91%) of product as a tan solid. Recrystallization from ethyl acetate/cyclohexane gave analytically pure material, mp 56°–58° C.

| Elemental Analysis: | C | H | N |
|---|---|---|---|
| Calculated | 47.86 | 4.63 | 8.59 |
| Found | 47.92 | 4.68 | 8.58 |

EXAMPLE 73

3-Pyridinecarboxylic acid, 5-chloro-6-(difluoromethyl)-4-methyl-2-(trifluoromethyl)-,ethyl ester. To a solution of 3.76 q (0.02B mol) of cupric chloride, 3.61 g (0.035 mol) of t-butyl nitrite and 80 mL of acetonitrile was added a solution of 7.0 g (0.023 mol) of product of Example 71 in 7 mL of acetonitrile. This was stirred at room temperature for 90 min, then poured into 200 mL of 1 M hydrochloric acid and extracted with chloroform. Normal workup afforded an orange oil which was filtered through a short silica gel column with 2% ethyl acetate/cyclohexane. Concentration in vacuo afforded 5.92 g (81%) of product as a colorless liquid; $n_D^{25}$ 1.452.

| Elemental Analysis: | C | H | N | Cl |
|---|---|---|---|---|
| Calculated | 41.59 | 2.86 | 4.41 | 11.16 |
| Found | 41.60 | 2.87 | 4.39 | 11.15 |

EXAMPLE 74

3-Pyridinecarboxylic acid, 5-bromo-6-(difluoromethyl)-4-methyl-2-(trifluoromethyl)-,ethyl ester. To a solution of 6.25 g (0.028 mol) of cupric bromide, 3.61 g (0.035 mol) of t-butyl nitrite and 80 mL of acetonitrile was added a solution of 7.0 g (0.023 mol) of product of Example 71 in 7 mL of acetonitrile. This was stirred at room temperature for 1.5 h, then poured into 200 mL of 10% hydrochloric acid and extracted with chloroform (3×50 mL). Normal workup gave a yellow oil which was filtered through a short silica gel column (2% ethyl acetate/cyclohexane) to give 7.54 g (91%) of product as a colorless liquid; $n_D^{25}$ 1.470.

| Elemental Analysis: | C | H | N | Br |
|---|---|---|---|---|
| Calculated | 36.49 | 2.51 | 3.87 | 22.07 |
| Found | 36.47 | 2.53 | 3.86 | 21.99 |

EXAMPLE 75

3-Pyridinecarboxylic acid, 6-(difluoromethyl)-5-iodo-4-methyl-2-(trifluoromethyl)-,ethyl ester. To a 0° C. solution of 7.0 g (0.023 mol) of product of Example 71, 4.21 g (0.023 mol) of 48% fluoroboric acid and 60 mL of acetonitrile was added 2.61 g of t-butyl nitrite dropwise. This was stirred at 0° C. for 1 h, then added to a rapidly stirred solution of 60 g of potassium iodide in 200 mL of water. After 15 min, the reaction mixture was diluted with 200 mL of water and extracted with chloroform (3×100 mL). The chloroform extract was washed with 10% sodium thiosulfate (2×50 mL), brine (50 mL) and dried through sodium sulfate. Concentration in vacuo afforded an orange oil which was filtered through a short plug of silica gel. The resulting oil was Kugelrohr distilled (150° C. @1 torr) to afford 1.73 g (18%) of product as a white solid, mp 41°–43° C.

| Elemental Analysis: | C | H | N |
|---|---|---|---|
| Calculated | 32.30 | 2.22 | 3.42 |
| Found | 32.51 | 2.12 | 3.60 |

EXAMPLE 76

3-Pyridinecarboxylic acid, 5-chloro-6-(difluoromethyl)-4-(1-methylethyl)-2-(trifluoromethyl)-, ethyl ester. To a mixture of 2.69 g (0.02 mol) of cupric chloride, 2.58 g (0.025 mol) of t-butyl nitrite and 40 mL of acetonitrile was added a solution of 5.44 g (0.017 mol) of product of Example 72 in 7 mL of acetonitrile. This was stirred at room temperature for 1.5 h, poured into 150 mL of 1 M hydrochloric acid and extracted into chloroform (3×50 mL). Normal workup gave 5.73 g of a brown oil which was passed through a short silica gel column with 2% ethyl acetate/cyclohexane. Kugelrohr distillation (140° C. @2 torr) of the resulting oil afforded 4.32 g (75%) of product as a colorless liquid; $n_D^{25}$ 1.457.

| Elemental Analysis: | C | H | N | Cl |
|---|---|---|---|---|
| Calculated | 45.17 | 3.79 | 4.05 | 10.26 |
| Found | 45.31 | 3.81 | 4.06 | 10.28 |

EXAMPLE 77

3-Pyridinecarboxylic acid, 5-bromo-6-(difluoromethyl)-4-(1-methylethyl)-2-(trifluoromethyl)-, ethyl ester. To a solution of 4.47 g (0.020 mol) of cupric bromide, 2.58 g (0.025 mol) of t-butyl nitrite and 40 mL of acetonitrile was added a solution of 5.49 g (0.17 mol) of product of Example 72 in 7 mL of acetonitrile. This was stirred at room temperature for 1.5 h, poured into 150 mL of 1 M hydrochloric acid and extracted with chloroform (3×75 mL). Normal workup afforded a brown oil which was filtered through a short silica gel column with 2% ethyl acetate/cyclohexane. Kugelrohr distillation (140° C. @2 torr) of the resulting oil afforded 5.13 g (78%) of product as a colorless liquid; $n_D^{25}$ 1.473.

| Elemental Analysis: | C | H | N | Br |
|---|---|---|---|---|
| Calculated | 40.02 | 3.36 | 3.59 | 20.48 |
| Found | 40.05 | 3.38 | 3.57 | 20.40 |

EXAMPLE 78

3-Pyridinecarboxylic acid, 6-(difluoromethyl)-5-iodo-4-(1-methylethyl)-2-(trifluoromethyl)-, ethyl ester. To a solution of 6.0 g (0.018 mol) of product of Example 72, 3.29 g (0.018 mol) of 48% fluoroboric acid and 45 mL of acetonitrile was added 2.04 g (0.02 mol) of t-butyl nitrite dropwise. This was stirred at 0° C. for 15 min, then was added to a rapidly stirred solution of 60 g of potassium iodide in 150 mL of water. The reaction mixture was stirred for 30 min, then was diluted with water (200 mL) and extracted with chloroform (3×50 mL). The chloroform extract was washed with 100 mL of 10% sodium thiosulfate, 100 mL of brine, and dried though sodium sulfate. Concentration in vacuo afforded a red-orange oil that was filtered through a short silica gel column with 2% ethyl acetate/cyclohexane. Kugelrohr distillation (160° C. @2 torr) of the resulting oil afforded 4.3 g (55%) of product as a light yellow oil; $n_D^{25}$ 1.498.

| Elemental Analysis: | C | H | N | I |
|---|---|---|---|---|
| Calculated | 35.72 | 3.00 | 3.20 | 29.03 |
| Found | 35.77 | 3.00 | 3.15 | 28.94 |

EXAMPLE 79

3-Pyridinecarboxylic acid, 5-chloro-6-(difluoromethyl)-4-propyl-2-(trifluoromethyl)-,ethyl ester. To a slurry of 4.97 g (0.037 mol) of cupric chloride, 4.84 g (0.047 mol) of t-butyl nitrite and 80 mL of acetonitrile was added a solution of 10.0 g (0.031 mol) of product of Example 16 in 10 mL of acetonitrile. Gas evolution occurred immediately. After the reaction was stirred at room temperature for 90 min, it was poured into 250 mL of 1 M hydrocholoric acid and extracted with chloroform. Normal workup afforded 10.45 g of a brown oil which was filtered through a short silica gel column (2% ethyl acetate/cyclohexane) and Kugelrohr distilled 130° C. @2 torr) to afford 7.33 g (68%) of product as a colorless liquid; $n_D^{25}$ 1.454.

| Elemental Analysis: | C | H | N | Cl |
|---|---|---|---|---|
| Calculated | 45.17 | 3.79 | 4.05 | 10.26 |
| Found | 45.19 | 3.81 | 4.02 | 10.34 |

EXAMPLE 80

3-Pyridinecarboxylic acid, 5-bromo-6-(difluoromethyl)-4-propyl-2-(trifluoromethyl)-,ethyl ester. To a solution of 8.26 g (0.037 mol) of cupric bromide, 4.84 g (0.047 mol) of t-butyl nitrite and 80 mL of acetonitrile was added 10.0 g (0.031 mol) of product of Example 16 in 10 mL of acetonitrile, resulting in immediate gas evolution. After 90 min the reaction mixture was poured into 250 mL of 1M hydrochloric acid. Extraction with chloroform (3×75 mL) and workup as usual afforded 11.81 g of a brown oil. This material was filtered through a short silica gel column (2% ethyl acetate/cyclohexane), then Kugelrohr distilled (135° C. @1.5 torr) to afford 8.7 g (72%) of product as a colorless oil; $n_D^{25}$ 1.467.

| Elemental Analysis: | C | H | N | Br |
|---|---|---|---|---|
| Calculated | 40.02 | 3.36 | 3.59 | 20.48 |
| Found | 40.14 | 3.38 | 3.58 | 20.58 |

EXAMPLE 81

3-Pyridinecarboxylic acid, 6-(difluoromethyl)-5-iodo-4-propyl-2-(trifluoromethyl)-,ethyl ester. To a 0° C. solution of 10.0 g (0.031 mol) of product of Example 16, 5.67 g of 48% fluoroboric acid (0.031 mol) and 55 mL of acetonitrile was added 3.50 g (0.034 mol) of t-butyl nitrite dropwise. After 20 min at 0° C., the reaction mixture was added to a rapidly-stirred solution of 80 g of potassium iodide in 175 mL of water. This was stirred for 45 min, diluted with 200 mL of water and extracted with chloroform (3×75 mL). The chloroform extract was washed with 10% sodium thiosulfate (2×50 mL), brine (100 mL) and dried through sodium sulfate. Normal workup afforded 12.8 g of an oily brown solid which was filtered through a short silica gel column with 2% ethyl acetate/cyclohexane. Kugelrohr distillation (140° C. at 1.5 torr) afforded 9.32 g (69%) of product as a white solid, mp 45°–48° C.

| Elemental Analysis: | C | H | N | I |
|---|---|---|---|---|
| Calculated | 35.72 | 3.00 | 3.20 | 29.03 |

| Elemental Analysis: | C | H | N | I |
|---|---|---|---|---|
| Found | 35.77 | 3.00 | 3.17 | 28.96 |

EXAMPLE 82

3-Pyridinecarboxylic acid, 5-chloro-4-ethyl -6-methyl-2-(trifluoromethyl)-,ethyl ester. To a stirred slurry of 2.92 g (0.022 mol) of cupric chloride, 2.80 g (0.027 mol) of t-butyl nitrite and 50 mL of acetonitrile was added a solution of 5.0 g (0.018 mol) of product of Example 18 in 10 mL of acetonitrile. This was stirred at room temperature for 2 h, then was poured into 150 mL of 1 M hydrochloric acid and extracted with chloroform (3×75 mL). Workup as usual afforded a brown oil that was Kugelrohr distilled (120° C. @1 torr) to give 4.73 g (88%) of product as a yellow liquid; $n_D^{25}$ 1.470.

| Elemental Analysis: | C | H | N | Cl |
|---|---|---|---|---|
| Calculated | 48.74 | 4.43 | 4.74 | 11.99 |
| Found | 48.83 | 4.20 | 5.11 | 12.26 |

EXAMPLE 83

3-Pyridinecarboxylic acid, 5-bromo-4-ethyl -6-methyl-2-(trifluoromethyl)-,ethyl ester. To a stirred solution of 4.85 g (0.022 mol) of cupric bromide, 2.80 g (0.027 mol) of t-butyl nitrite and 50 mL of acetonitrile was added a solution of 5.0 g (0.018 mol) of product of Example 18 in 10 mL of acetonitrile. This was stirred at room temperature for 2 h, then was diluted with 200 mL of 1M hydrochloric acid and extracted with chloroform (3×75 mL). Normal workup afforded an orange oil that was Kugelrohr distilled (120° C. @1 torr) to give 5.21 g (84%) of product as a light yellow oil; $n_D^{25}$ 1.470.

| Elemental Analysis: | C | H | N | Br |
|---|---|---|---|---|
| Calculated | 42.37 | 3.85 | 4.12 | 23.49 |
| Found | 42.43 | 3.88 | 4.11 | 23.41 |

EXAMPLE 84

3-Pyridinecarboxylic acid, 4-ethyl-5-iodo-6-methyl-2-(trifluoromethyl)-, ethyl ester. To a 0° C. solution of 4.66 g (0.017 mol) of product of Example 18, 3.08 g of 48% fluoroboric acid and 35 mL of acetonitrile was added 1.91 g (0.019 mol) of t-butyl nitrite dropwise. This was stirred at 0° C. for 25 min, then was added to a rapidly stirred solution of 40 g of potassium iodide in 120 mL of water. After 30 min, 120 mL of water was added and the reaction mixture was j extracted with chloroform (3×70 mL). The chloroform extracts were washed with 10% sodium thiosulfate (2×50 mL), brine (50 mL) and dried through sodium sulfate. Workup as usual afforded an orange oil that was Kugelrohr distilled (120° C. @1 torr) to give 4.88 g (75%) of product as a light yellow oil; $n_D^{25}$ 1 504.

| Elemental Analysis: | C | H | N | I |
|---|---|---|---|---|
| Calculated | 37.23 | 3.38 | 3.62 | 32.78 |
| Found | 37.35 | 3.42 | 3.55 | 32.50 |

EXAMPLE 85

3-Pyridinecarboxylic acid, 5-azido-6-(difluoromethyl)-4-ethyl-2-(trifluoromethyl)-,ethyl ester. To a 0° C. solution of 4.0 9 (0.013 mol) of product of Example 2, 2.34 g (0.013 mol) of 48% fluoroboric acid and 30 mL of acetonitrile was added 1.46 g (0.014 mol) of t-butyl nitrite dropwise. After 30 min, a solution of 1.7 g (0.026 mol) of sodium azide in 9 mL of water was added dropwise, resulting in vigorous gas evolution. This was stirred at room temperature for 30 min, diluted with water (50 mL) and extracted with chloroform (3×25 mL). Workup as usual afforded a yellow oil. Chromatography on silica gel (2% ethyl acetate/cyclohexane) afforded 2.44 g (55%) of product as a light yellow oil; $n_D^{25}$ 1.476.

| Elemental Analysis: | C | H | N |
|---|---|---|---|
| Calculated | 42.61 | 3.28 | 16.56 |
| Found | 42.76 | 3.33 | 16.49 |

EXAMPLE 86

3-Pyridinecarboxylic acid, 6-(difluoromethyl)-4-ethyl-5-{[(1-methylethoxy)methylene]amino}-2-(trifluoromethyl)-,ethyl ester. A solution of 4.0 g (0.013 mol) of product of Example 2, 10 mL of triisopropyl orthoformate and 70 mg of p-toluenesulfonic acid was heated to 100° C. and stirred for 4 h. The temperature was then raised to 130° C. and stirring was continued for another 18 hours. The reaction mixture was then concentrated in vacuo and the residue was Kugelrohr distilled (150° C. @1 torr) to give 1.58 g (32%) of product as a colorless oil; $n_D^{25}$ 1.502.

| Elemental Analysis: | C | H | N |
|---|---|---|---|
| Calculated | 50.26 | 5.01 | 7.33 |
| Found | 49.97 | 4.95 | 7.67 |

EXAMPLE 87

3-Pyridinecarboxylic acid, 6-(difluoromethyl)-5-{[(2-methylpropoxy)methylene]amino}-4-(2-methylpropyl)-2-(trifluoromethyl)-,ethyl ester. A solution of 4.0 g (0.012 mol) of product of Example 1, 10 mL of triisobutyl orthoformate and 70 mg of p-toluenesulfonic acid was stirred at 100° C. for 18 h, then at 120° C. for another 18 h. The reaction mixture was concentrated in vacuo. The residue was chromatographed on silica gel using 2% ethyl acetate/cyclohexane. Workup of the correct fraction gave 1.93 g (39%) of product as a light yellow oil; $n_D^{25}$ 1.500.

| Elemental Analysis: | C | H | N |
|---|---|---|---|
| Calculated | 53.77 | 5.94 | 6.60 |
| Found | 54.30 | 6.00 | 6.34 |

EXAMPLE 88

3-Pyridinecarboxylic acid, 6-(difluoromethyl)-4-(2-methylpropyl)-5-[(propoxymethylene) amino]-2-(trifluoromethyl)-,ethyl ester. A solution of 4.0 g (0.012 mol) of product of Example 1, 10 mL of tripropyl orthoformate and 70 mg of p-toluenesulfonic acid was stirred at 100° C. for 18 h. The reaction mixture was concentrated in vacuo and the residue was chromatographed on silica gel using 2% ethyl acetate/cyclohexane. Workup of the correct fraction gave 2.71 g (56%) of product as a colorless oil; $n_D^{25}$ 1.458.

| Elemental Analysis: | C | H | N |
|---|---|---|---|
| Calculated | 52.68 | 5.65 | 6.83 |
| Found | 52.85 | 5.76 | 6.43 |

EXAMPLE 89

3-Pyridinecarboxylic acid, 6-(difluoromethyl)-4-ethyl-5-{2,2,2-trifluoro-1-(dimethylamino) ethylidene]amino}-2-(trifluoromethyl)-,ethyl ester. To a rapidly stirred solution of 4.3 g (0.010 mol) of product of Example 47 in 5 mL of dioxane was added 4.5 mL (0.025 mol) of 26% aqueous dimethylamine. An exothermic reaction occurred. When the reaction cooled to room temperature, 50 mL of water was added and the product was extracted into methylene chloride (3×25 mL). Workup as usual afforded a dark oil that was Kugelrohr distilled (130° C. @1 torr) to give 2.35 g (54%) of product as a yellow oil; $n_D^{25}$ 1.466.

| Elemental Analysis: | C | H | N |
|---|---|---|---|
| Calculated | 44.15 | 3.94 | 9.65 |
| Found | 44.17 | 3.77 | 9.37 |

EXAMPLE 90

3-Pyridinecarboxylic acid, 6-(difluoromethyl)-4-ethyl-5-{2,2,2-trifluoro-1-(methylamino) ethylidene]amino}-2-(trifluoromethyl)-, ethyl ester. To a stirred solution of 4.0 g (0.0094 mol) of product of Example 47 and 5 mL of dioxane was added 2 mL of 40% aqueous methylamine. After 30 min, 50 mL of water was added and the product was extracted with methylene chloride. Workup as usual, followed by Kugelrohr distillation (170° C. @1 torr) gave 3.07 g (78%) of product as a white solid, mp 95°-97° C.

| Elemental Analysis: | C | H | N |
|---|---|---|---|
| Calculated | 42.77 | 3.59 | 9.97 |
| Found | 42.59 | 3.63 | 9.98 |

EXAMPLE 91

3-Pyridinecarboxylic acid, 5-(ethoxymethylene)amino]-4-ethyl-6-methyl-2-(trifluoromethyl)-,ethyl ester. A solution of 3.5 g (0.013 mol) of product of Example 18, 10 mL of triethyl orthoformate and 70 mg of p-toluenesulfonic acid was stirred at 100° C. for the weekend. The reaction mixture was then concentrated in vacuo and the residue was Kugelrohr distilled (150° C. @1 torr) to give 3.73 g (88%) of product as a colorless oil; $n_D^{25}$ 1.477.

| Elemental Analysis: | C | H | N |
|---|---|---|---|
| Calculated | 54.21 | 5.76 | 8.43 |
| Found | 54.16 | 5.80 | 8.23 |

EXAMPLE 92

3-Pyridinecarboxylic acid, 5-{[(dimethylamino)methylene]amino}-4-ethyl-6-methyl-2-(trifluoromethyl)-, ethyl ester. A solution of 3.70 g (0.013 mol) of product of Example 18, 10 mL of dimethylformamide dimethyl acetal, and 70 mg of p-toluenesulfonic acid was stirred at 100° C. overnight. The reaction mixture was concentrated in vacuo and the residue was Kugelrohr distilled (150° C. @1 torr) to give 3.55 g (80%) of product as a yellow solid. Recrystallization from ethyl acetate/cyclohexane gave analytically pure material as a white solid, mp 71°-73° C.

| Elemental Analysis: | C | H | N |
|---|---|---|---|
| Calculated | 54.37 | 6.08 | 12.68 |
| Found | 54.38 | 6.13 | 12.62 |

EXAMPLE 93

3-Pyridinecarboxylic acid, 5-azido-6-(difluoromethyl)-4-(2-methylpropyl)-2-(trifluoromethyl)-, ethyl ester. To a 0° C. solution of 4.0 g (0.012 mol) of product of Example 1, 2.16 g (0.012 mol) of (48%) fluoroboric acid and 40 mL of acetonitrile was added 1.34 g of t-butyl nitrite dropwise. This was stirred at 0°0 C. for 20 min then a solution of 2.1 g of sodium azide in 11 mL of water was added slowly, causing immediate gas evolution. After 10 min, 50 mL of water was added and the product was extracted into chloroform. Workup as usual afforded a yellow oil which was chromatographed on silica gel using 2% ethyl acetate/cyclohexane. Workup of the first fraction gave 2.85 g (66%) of product was a light yellow oil; $n_D^{25}$ 1.470.

| Elemental Analysis: | C | H | N |
|---|---|---|---|
| Calculated | 45.91 | 4.13 | 15.30 |
| Found | 45.71 | 4.21 | 15.37 |

Example 94

3-Pyridinecarboxylic acid, 6-(difluoromethyl)-4-ethyl-5-({1-[(1-methylethyl)thio]-2,2,2-trifluoroethylidene}amino)-2-(trifluoromethyl)-, ethyl ester. To a slurry of 0.40 g (0.010 mol) of 60% sodium hydride in 7 mL of anhydrous tetrahydrofuran under a nitrogen atmosphere was added 0.74 g (0.0097 mol) of 2-propanethiol. This was stirred at room temperature for 30 min, then a solution of 4.0 g (0.0094 mol) of product of Example 47 in 5 mL of tetrahydrofuran was added dropwise. This was stirred for 30 min, diluted with 25 mL of water and extracted with ether (3×15 mL). Workup as usual, followed by Kugelrohr distillation (150° C. @1 torr) afforded 2.92 g (67%) of product as a yellow liquid; $n_D^{25}$ 1.466.

| Elemental Analysis: | C | H | N | S |
|---|---|---|---|---|
| Calculated | 43.78 | 3.89 | 6.01 | 6.87 |
| Found | 44.09 | 3.90 | 5.90 | 6.89 |

EXAMPLE 95

3-Pyridinecarboxylic acid, 6-(difluoromethyl)-4-ethyl-5-(methylamino)-2-(trifluoromethyl)-, ethyl ester. To 40 ml of acetic anhydride at 0° C. was added 20 ml of formic acid. This was warmed to room temperature, then was heated to 50° C. for 15 min. The flask was immediately re-cooled to 0° C. and 5.0 g (0.016 mol) of product of Example 2 was added. This was stirred at room temperature for 18 hours, then was concentrated in vacuo to afford a yellow oil. This was dissolved in 15 ml of anhydrous tetrahydrofuran, and stirred at 0° C. under a dry nitrogen atmosphere. To this, 20 ml (0.04 mol) of 2.0 M borane-dimethyl sulfide complex in tetrahydrofuran was added dropwise. After the addition was complete, the reaction mixture was stirred at 70° C. for 3.5 hours. The reaction mixture was then cooled to 0° C. and 10 ml of methanol was added slowly. After frothing ceased, the mixture was warmed to room temperature and stirred for 1 hour. The 7 ml of concentrated hydrochloric acid was added and the mixture was refluxed for 1 hour. The reaction mixture was concentrated in vacuo to afford a yellow solid, which was slurried with ethyl acetate and stirred with 25 ml of 10% sodium hydroxide solution. The organic layer was separated and workup as usual gave a yellow oil. Chromatography on silica gel using 5% ethyl acetate/cyclohexane gave 2.77 g of product as a yellow oil which slowly solidified, mp 38°–40° C.

| Elemental Analysis: | C | H | N |
|---|---|---|---|
| Calculated | 47.86 | 4.63 | 8.59 |
| Found | 47.88 | 4.63 | 8.56 |

EXAMPLE 96

3-Pyridinecarboxylic acid, 6-(difluoromethyl)-4-ethyl-5-[(2,2,2-trifluoroethyl)amino]-2-(trifluoromethyl)-,ethyl ester. To a solution of 5.16 g (0.0128 mol) of product of Example 25 in 12 ml of anhydrous tetrahydrofuran at 0° C. under a nitrogen atmosphere, was added 16 ml of 2.0M borane-dimethyl sulfide complex in tetrahydrofuran dropwise. The reaction mixture was heated at 70° C. for 3 hours. Then the mixture was cooled to 0° C. and 10 ml of methanol was added carefully. After frothing ceased 10 ml of concentrated hydrochloric acid was added and the mixture was refluxed for 1 hour. The reaction mixture was concentrated in vacuo and the residue was slurried with 50 ml of ethyl acetate and stirred with 25 ml of 10% sodium hydroxide. Workup of the ethyl acetate solution afforded a yellow oil that was chromatographed on silica gel with 5% ethyl acetate/cyclohexane. Workup of the correct fraction gave 2.15 g (43%) of product as a colorless oil; $n_D^{25}$ 1.439.

| Elemental Analysis: | C | H | N |
|---|---|---|---|
| Calculated | 42.65 | 3.58 | 7.11 |
| Found | 42.93 | 3.58 | 7.13 |

EXAMPLE 97

3-Pyridinecarboxylic acid, 5-azido-6-(difluoromethyl)-4-methyl-2-(trifluoromethyl)-, ethyl ester. A solution of 4.0 g (0.0134 mol) of product of Example 71, 2.45 g (0.0134 mol) of 48% fluoroboric acid and 45 ml of acetonitrile was stirred at 0° C. and 1.44 g (0.014 mol) of t-butyl nitrite was added dropwise. This was allowed to stir at 0° C. for 20 minutes, then a solution of 2.1g of sodium azide in 11 ml of water was added dropwise, resulting in immediate gas evolution. After stirring for an additional 10 minutes the reaction mixture was diluted with water and extracted with chloroform. Workup as usual gave a yellow oil which was chromatographed on silica gel using 2% ethyl acetate/cyclohexane. Workup of the correct fraction gave 2.27 g (52%) of product as a yellow oil; $n_D^{25}$ 1 474.

| Elemental Analysis: | C | H | N |
|---|---|---|---|
| Calculated | 40.75 | 2.80 | 17.28 |
| Found | 40.96 | 2.71 | 17.03 |

EXAMPLE 98

3-Pyridinecarboxylic acid, 6-(difluoromethyl)-5-[(methoxymethylene)amino]-4-(1-methylethyl)-2-(trifluoromethyl)-, ethyl ester. A solution of 5.0 g (0.015 mol) of product of Example 72, 10 ml of trimethyl orthoformate and 70 mg of p-toluenesulfonic acid was heated to 100° C. and stirred for 2 hours. The reaction mixture was concentrated in vacuo and the residue was kugelrohr distilled (140° C. at 1 torr) to afford 5.05 g (90%) of product as a colorless oil which slowly crystallized, mp 57°–59° C.

| Elemental Analysis: | C | H | N |
|---|---|---|---|
| Calculated | 48.92 | 4.65 | 7.61 |
| Found | 48.91 | 4.66 | 7.59 |

EXAMPLE 99

3-Pyridinecarboxylic acid, 6-(difluoromethyl)-5-[(ethoxymethylene)amino]-4-(1-methylethyl)-2-(trifluoromethyl)-, ethyl ester. A solution of 5.0 g (0.015 mol) of product of Example 72, 10 ml of triethyl orthoformate and 70 mg of p-toluenesulfonic acid was heated at 100° C. overnight. The reaction mixture was concentrated in vacuo and the residue was kugelrohr distilled (145° C. @1 torr) to give 5.07 g of product as a colorless oil; $n_D^{25}$ 1.464.

| Elemental Analysis: | C | H | N |
|---|---|---|---|
| Calculated | 50.26 | 5.01 | 7.33 |
| Found | 50.26 | 5.05 | 7.30 |

EXAMPLE 100

3-Pyridinecarboxylic acid, 6-(difluoromethyl)-4-ethyl-5-{[(dimethylamino)methylene]amino}-2-(trifluoromethyl)-, ethyl ester. A solution of 4.0 g (0.0128 mol) of product of Example 2, 10 ml of dimethylformamide dimethyl acetal and 70 mg of p-toluenesulfonic acid was refluxed overnight. The reaction mixture was concentrated in vacuo and the residue was kugelrohr distilled (145° C. at 1 torr) to afford 3.90 g of product as a yellow solid, mp 50°–52° C.

| Elemental Analysis: | C | H | N |
|---|---|---|---|
| Calculated | 49.05 | 4.94 | 11.44 |
| Found | 49.02 | 4.93 | 11.33 |

EXAMPLE 101

20 3-Pyridinecarboxylic acid, 6-(difluoromethyl)-5-{[(dimethylamino)methylene]amino}-4-(1-methylethyl)-2-(trifluoromethyl)-, ethyl ester. A solution of 4.25 g (0.013 mol) of product of Example 72, 10 ml of dimethylformamide dimethyl acetal and 70 mg of p-toluenesulfonic acid was heated overnight at ° C. The reaction mixture was concentrated in vacuo and the residue was chromatographed on silica gel ethyl acetate/cyclohexane. Workup of the correct fraction afforded 4.17 g (84%) of product as a yellow oil; $n_D^{25}$ 1.487.

| Elemental Analysis: | C | H | N |
|---|---|---|---|
| Calculated | 50.39 | 5.29 | 11.02 |
| Found | 50.33 | 5.22 | 11.28 |

EXAMPLE 102

3-Pyridinecarboxylic acid, 5-azido-6-(difluoromethyl)-4-(1-methylethyl)-2-(trifluoromethyl)-, ethyl ester. To a 0° C. solution of 4.0 g (0.012 mol) of product of Example 72, 2.25 g (0.012 mol) of 48% fluoroboric acid and 40 ml of acetonitrile was added 1.40 g (0.013 mol) of t-butyl nitrite dropwise. This was stirred at 0° C. for 20 minutes, then a solution of 2.1g of sodium azide in 11 ml of water was added slowly, resulting in vigorous gas evolution. After stirring for 10 minutes, 100 ml of water was added and the product was extracted into chloroform (3×50 ml). Workup as usual afforded an orange oil which was chromatrographed on silica gel using 2% ethyl acetate/cyclohexane. Workup of the correct fraction gave 2.41 g (56%) of product as a slightly yellow oil; $n_D^{25}$ 1.472.

| Elemental Analysis: | C | H | N |
|---|---|---|---|
| Calculated | 44.33 | 3.72 | 15.91 |
| Found | 44.11 | 3.72 | 15.91 |

EXAMPLE 103

3-Pyridinecarboxylic acid, 6-(difluoromethyl)-4-ethyl-5-(sulfinylamino)-2-(trifluoromethyl)-, ethyl ester. A solution of 4.0 g of product of Example 2 and 15 ml of thionyl chloride was stirred at reflux overnight. The excess thionyl chloride was removed in vacuo and the residue was kugelrohr distilled (145° C. at 1 torr) to give 4.21 g (92%) of product as a bright yellow oil; $n_D^{25}$ 1 477.

| Elemental Analysis: | C | H | N | S |
|---|---|---|---|---|
| Calculated | 40.23 | 3.09 | 7.82 | 8.95 |
| Found | 40.30 | 3.11 | 7.80 | 8.87 |

EXAMPLE 104

3-Pyridinecarboxylic acid, 6-(difluoromethyl)-5-isocyanato-4-propyl-2-(trifluoromethyl)-, ethyl ester. The product of Example 47 (5.0 g, 0.0134 mol) of European Patent Application No. 133,612 published Feb. 27, 1985, was added to 1.66 g (0.0144 mol) of azidotrimethyl silane and 10 ml of carbon tetrachloride and stirred at reflux until gas u evolution ceased (~45 minutes). The reaction mixture was concentrated in vacuo and the residue was kugelrohr distilled (130° C. at 1 torr) to give 2.65 g of product as a light yellow oil; $n_D^{25}$ 1.4S9.

| Elemental Analysis: | C | H | N |
|---|---|---|---|
| Calculated | 47.74 | 3.72 | 7.95 |
| Found | 47.74 | 3.89 | 7.80 |

EXAMPLE 105

3-Pyridinecarboxylic acid, 6-(difluoromethyl)-4-propyl-5-[(2,2,2-trifluoro-1-methoxyethylidene)amino]-2-(trifluoromethyl)-, ethyl ester. To a solution of 2.16 g (0.01 mol) of 25% methanolic sodium methoxide in 5 ml of methanol was added a solution of 4.0 g (0.0091 mol) of product of Example 08 in 5 ml of methanol, resulting in the immediate formation of a white precipitate. The reaction mixture was stirred for 1 hour, then was poured into water (50 ml) and extracted with ether (3×15 ml). Workup as usual afforded a colorless oil which was kugelrohr distilled (130° at 1.5 torr) to give 3.27 g (82%) of product as a colorless oil; $n_D^{25}$ 1.438.

| Elemental Analysis: | C | H | N |
|---|---|---|---|
| Calculated | 44.05 | 3.70 | 6.42 |
| Found | 44.13 | 3.69 | 6.44 |

EXAMPLE 106

3-Pyridinecarboxylic acid, 6-(difluoromethyl)-5-{[(dimethylamino)methylene]amino}-4-propyl2-(trifluoromethyl)-, ethyl ester. A solution of 4.0 g (0.012 mol) of product of Example 16, 10 ml of dimethylformamide dimethyl acetal and 70 mg of p-toluenesulfonic acid was stirred at reflux overnight. The reaction mixture was then concentrated in vacuo and the residue was kugelrohr distilled (165° C. at 1.5 torr) to give 4.10g (87%) of product as a yellow oil; $n_D^{25}$ 1.486.

| Elemental Analysis: | C | H | N |
|---|---|---|---|
| Calculated | 50.39 | 5.29 | 11.02 |
| Found | 50.50 | 5.29 | 10.99 |

EXAMPLE 107

3-Pyridinecarboxylic acid, 6-(difluoromethyl)-5-[(trifluoroacetyl)amino]-4-propyl-2-(trifluoromethyl)-, ethyl ester. A solution of 35.0 g (0.107 mol) of product of Example 16, 100 ml of methylene chloride and 30 g (0.14 mol) of trifluoroacetic anhydride was stirred at room temperature overnight. Concentration in vacuo afforded 45.7 g (~100%) of product as a white solid. Recrystallization from ethyl acetate/cyclohexane gave analytically pure material, mp 95°-97° C.

| Elemental Analysis: | C | H | N |
|---|---|---|---|
| Calculated | 42.67 | 3.34 | 6.63 |
| Found | 42.80 | 3.20 | 6.74 |

EXAMPLE 108

3-Pyridinecarboxylic acid, 5-(1-chloro-2,2,2-trifluoroethylidene)amino]-6-(difluoromethyl) -4-propyl-2-(trifluoromethyl)-, ethyl ester. A mixture of 39.58 g (0.0937 mol) of product of Example 107 and 19.51 g (0.0937 mol) of phosphorous pentachloride was heated at 135° C. for 3 hours. The reaction mixture was concentrated in vacuo and the residue was kugelrohr distilled (130° C. at 1 torr) to give 40.07 g (97%) of product as a colorless oil; $n_D^{25}$ 1.434.

| Elemental Analysis: | C | H | N | Cl |
|---|---|---|---|---|
| Calculated | 40.88 | 2.97 | 6.36 | 8.04 |
| Found | 40.53 | 2.73 | 6.26 | 8.08 |

EXAMPLE 109

3-Pyridinecarboxylic acid, 5-{[1-(diethoxyphosphinyl)-2,2,2-trifluoroethylidene]amino}-6-(difluoromethyl)-4-propyl-2-(trifluoromethyl)-, ethyl ester. A solution of 6.0 g (0.0136 mol) of product of Example 108 and 2.26 g (0.0136 mol) of triethyl phosphine was stirred at 160° C. for 30 min. The reaction mixture was then cooled to room temperature affording 7.35 g (~quant.) of product as a yellow oil; $n_D^{25}$ 1.437.

| Elemental Analysis: | C | H | N |
|---|---|---|---|
| Calculated | 42.08 | 4.27 | 5.17 |
| Found | 41.68 | 4.29 | 5.14 |

EXAMPLE 110

3-Pyridinecarboxylic acid, 6-(difluoromethyl)-4-propyl-5-[(2,2,2-trifluoro-1-ethoxyethylidene)amino]-2-(trifluoromethyl)-, ethyl ester. To a solution of 3.24 g (0.010 mol) of 21% ethanolic sodium ethoxide and 5 ml of ethanol was added a solution of 4.0 g (0.0091 mol) of product of Example 108 in 5 ml of ethanol. This was stirred at room temperature for 15 minutes during which time a white precipitate formed. The reaction mixture was poured into water (50 ml) and extracted with ether. Workup as usual gave a yellow oil which was kugelrohr distilled (150° at 1.5 torr) to give 3.87 g (84%) of product as a colorless oil; $n_D^{25}$ 1.438.

| Elemental Analysis: | C | H | N |
|---|---|---|---|
| Calculated | 45.34 | 4.03 | 6.22 |
| Found | 45.44 | 4.00 | 6.26 |

EXAMPLE 111

3-Pyridinecarboxylic acid, 6-(difluoromethyl)-4-propyl-2-(trifluoromethyl)-5-[5-(trifluoromethyl)-1H-tetrazol-1-yl]-, ethyl ester. To a solution of 4.0 g (0.0091 mol) of product of Example 108 in 20 ml of tetrahydrofuran was added 0.65 g (0.01 mol) of sodium azide followed by the addition of 4 ml of water. The reaction mixture was stirred at room temperature for 30 minutes, then was diluted with water (50 ml) and extracted with chloroform (3×25 ml). Normal workup gave 3.87 g (86%) of product as a white solid. Recrystallization from ethyl acetate/cyclohexane gave analytically pure material, mp 66°-68° C.

| Elemental Analysis: | C | H | N |
|---|---|---|---|
| Calculated | 40.28 | 2.93 | 15.66 |
| Found | 40.07 | 2.87 | 15.77 |

EXAMPLE 112

3-Pyridinecarboxylic acid, 6-(difluoromethyl)-5-{[1-(dimethylamino)-2,2,2-trifluoroethylidene]amino}-4-propyl-2-(trifluoromethyl)-, ethyl ester. To a solution of 4.0 g (0.0091 mol) of product of Example 108 and 10 ml of dioxane was added 4.5 ml of 26% aq. dimethylamine. The solution became warm immediately. This was allowed to stir for 30 minutes, then was diluted with water (50 ml) and extracted with 10 chloroform (3×25 ml). Normal workup gave an orange oil which was kugelrohr distilled (165° C. at 1 torr) to give 3.77 g (84%) of product as a colorless oil; $n_D^{25}$ 1.464.

| Elemental Analysis: | C | H | N |
|---|---|---|---|
| Calculated | 45.44 | 4.26 | 9.35 |
| Found | 45.42 | 4.18 | 9.19 |

EXAMPLE 113

3-Pyridinecarboxylic acid, 6-(difluoromethyl)-5-{[2,2,2-L. iflucrc 1-(methylamino) ethylidene]amino}-4-propyl-2-(trifluoromethyl)-, ethyl ester. To a stirred solution of 4.0 g (0.0091 mol) of product of Example 108 and 10 ml of dioxane was added 2 ml of 40% aq. methylamine. The reaction mixture became warm. This was allowed to stir for 30 minutes, then was diluted with water (50 ml) and extracted with chloroform (3×25 ml). Normal workup gave a yellow oil which was kugelrohr distilled (165° C. at 1 torr) to give 3.53 g (89%) of product as a thick colorless oil; $n_D^{25}$ 1 461.

| Elemental Analysis: | C | H | N |
|---|---|---|---|
| Calculated | 44.15 | 3.94 | 9.65 |
| Found | 44.25 | 3.77 | 9.38 |

EXAMPLE 114

3-Pyridinecarboxylic acid, 2-(difluoromethyl)-5-[(ethoxymethylene)amino]-4-(2-methylpropyl) -6-(trifluoromethyl)-, methyl ester. A solution of 4.0 g (0.013 mol) of product of Example 209, 7.8 ml of triethyl orthoformate and 78 mg of p-toluenesulfonic acid was heated to 100° C. and stirred for 6 hours. The reaction mixture was concentrated in vacuo to give 5.39 g (100%) of product as a colorless oil. Chromatography on silica gel (1% ethyl acetate/cyclohexane) gave analytically pure material; $n_D^{25}$ 1.462.

| Elemental Analysis: | C | H | N |
|---|---|---|---|
| Calculated | 50.26 | 5.01 | 7.33 |
| Found | 50.50 | 5.09 | 7.30 |

EXAMPLE 115

3-Pyridinecarboxylic acid, 5-amino-2-(difluoromethyl)-4-ethyl-6-(trifluoromethyl)-, methyl ester. To a stirred slurry of 14.3 g of sodium azide, 25 ml of water and 75 ml of acetone was slowly added a solution of 35.77 g (0.103 mol) of methyl 5-chlorocarbonyl-2-(difluoromethyl)-4-ethyl-6-(trifluoromethyl)3-pyridinecarboxylic in 20 ml of acetone. An exothermic reaction followed with vigorous gas evolution. The reaction mixture was allowed to cool to room temperature and diluted with water (300 ml) and extracted into chloroform (3×100 ml). Normal workup afforded 26.61 g (82%) of product as a light yellow solid. Trituration with cyclohexane gave analytically pure material, mp 54°–56° C.

| Elemental Analysis: | C | H | N |
|---|---|---|---|
| Calculated | 44.30 | 3.72 | 9.39 |
| Found | 44.37 | 3.72 | 9.37 |

EXAMPLE 116

3-Pyridinecarboxylic acid, 2-(difluoromethyl)-4-ethyl-5-[dimethoxymethylene)amino]-6-(trifluoromethyl)-, methyl ester. A solution of 4.0 g (0.013 mol) of product of Example 115, 7.4 ml of trimethyl orthoformate and 74 mg of p-toluenesulfonic acid was refluxed overnight. The reaction mixture was then concentrated in vacuo and the residue kugelrohr distilled (150°–165° C. at 1 torr) to give 4.24 g (98%) of product as white solid, mp 67°–69° C.

| Elemental Analysis: | C | H | N |
|---|---|---|---|
| Calculated | 45.89 | 3.85 | 8.23 |
| Found | 45.92 | 3.85 | 8.21 |

EXAMPLE 117

3-Pyridinecarboxylic acid, 2-(difluoromethyl)-5-[(ethoxymethylene)amino]-4-ethyl-6-(trifluoromethyl)-, methyl ester. A solution of 4.0 g (0.013 mol) of product of Example 115, 7.8 ml of triethyl orthoformate and 78 mg of p-toluenesulfonic acid was refluxed overnight. The reaction mixture was concentrated in vacuo and the residue was kugelrohr distilled (150°–165° C. at 1 torr) to give 4.3 g (0.012 mol) of product as a white solid. Trituration with cyclohexane gave analytically pure material, mp 68°–69° C.

| Elemental Analysis: | C | H | N |
|---|---|---|---|
| Calculated | 47.46 | 4.27 | 7.91 |
| Found | 47.37 | 4.30 | 7.90 |

EXAMPLE 118

3-Pyridinecarboxylic acid, 2-(difluoromethyl)-5-[(methoxymethylene)amino]-4-(2-methylpropyl)-6-(trifluoromethyl)-, methyl ester. A solution of 3.5 g (0.011 mol) of product of Example 209, 6.7 ml of trimethyl orthoformate, and 67 mg of p-toluenesulfonic acid was refluxed for 2 hours. Reaction mixture was then concentrated in vacuo and the residue kugelrohr distilled (150°–160° C. at 1 torr) to give 3.67 g (93%) of product as a colorless oil; $n_D^{25}$ 1.466.

| Elemental Analysis: | C | H | N |
|---|---|---|---|
| Calculated | 48.92 | 4.65 | 7.61 |
| Found | 48.98 | 4.66 | 7.61 |

EXAMPLE 119

3-Pyridinecarboxylic acid, 5-bromo-2-(difluoromethyl)-4-ethyl-6-(trifluoromethyl)-, methyl ester. To a stirred solution of 3.41 g (0.015 mol) of copper (II) bromide and 1.96 g (0.019 mol) of t-butyl nitrite in 36 ml of acetonitrile was added a solution of 4.0 g (0.013 mol) of product of Example 115 in 7 ml of acetonitrile. The reaction was stirred at room temperature for 1 hour, then was poured into 180 ml of 20% aqueous hydrochloric acid and extracted with ether (3×50 ml). Normal workup followed by kugelrohr distillation (130°–145° C. at 1 torr) gave 3.63 g (79%) of product as a colorless oil. Chromatography of a small amount of product on silica gel (2% ethyl acetate/cyclohexane) gave an analytically pure white solid, mp 49°–51° C.

| Elemental Analysis: | C | H | N | Br |
|---|---|---|---|---|
| Calculated | 36.49 | 2.51 | 3.87 | 22.07 |
| Found | 37.14 | 2.59 | 3.92 | 22.39 |

EXAMPLE 120

3-Pyridinecarboxylic acid, 5-chloro-2-(difluoromethyl)-4-ethyl-6-(trifluoromethyl)-, methyl ester. To a stirred solution of 2.05 g (0.015 mol) of copper (II) chloride and 1.96 g (.019 mol) of t-butyl nitrite in 36 ml of acetonitrile was added a solution of 4.0 g (0.013 mol) of product of Example 115 in 7 ml of acetonitrile. The reaction was stirred at room temperature for 1 hour. The reaction mixture was poured into 180 ml of 20% aqueous hydrochloric acid and extracted with ether (3×50 ml). Workup as usual followed by kugelrohr distillation (130°–145° C.) gave 3.28 g (81%) of product as a colorless oil. Chromatography of a small amount of product on silica gel (2% ethyl acetate/cyclohexane) gave analytically pure material; $n_D^{25}$ 1.454.

| Elemental Analysis: | C | H | N | Cl |
|---|---|---|---|---|
| Calculated | 41.59 | 2.86 | 4.41 | 11.16 |
| Found | 41.72 | 2.88 | 4.47 | 11.20 |

EXAMPLE 121

3-Pyridinecarboxylic acid, 2-(difluoromethyl)-4-ethyl-5-iodo-6-(trifluoromethyl)-, methyl ester. To a stirred solution of 3.98 g (0.013 mol) of product of Example 115, 2.32 g (0.013 mol) of 48% fluoroboric acid and 33 ml of acetonitrile in an ice bath was slowly added 1.44 g (0.014 mol) of t-butyl nitrite. The solution was stirred at 0° C. for 30 minutes and then added to a rapidly stirred solution of 33.17 g (0.20 mol) of potassium iodide in 120 ml water. After 30 minutes, the reaction mixture was diluted with 120 ml of water and extracted with chloroform (3×75 ml). The chloroform solution was washed with 10% sodium thiosulfate solution (2×75 ml). Workup as usual followed by kugelrohr distillation (140°–165° C. at 1 torr) gave 3.75 g (72%) of product as an off-white solid, mp 63°–65° C. Chromatography of a small amount of product on silica gel (2% ethyl acetate/cyclohexane) gave an analytically pure white solid, mp 72°–73° C.

| Elemental Analysis: | C | H | N | I |
|---|---|---|---|---|
| Calculated | 32.30 | 2.22 | 3.42 | 31.02 |
| Found | 32.12 | 2.23 | 3.37 | 30.98 |

EXAMPLE 122

3-Pyridinecarboxylic acid, 5-bromo-2-(difluoromethyl)-4-(2-methylpropyl)-6-(trifluoromethyl) -, methyl ester. To a stirred solution of 16.22 g (0.072 mol) of copper (II) bromide and 9.32 g (0.091 mol) of t-butyl nitrite in 170 ml of acetonitrile was added a solution of 19.71 g (0.060 mol) of product of Example 209 in 34 ml of acetonitrile. The reaction was stirred at room temperature for 1 hour. The reaction mixture was poured into 856 ml of 20% hydrochloric acid and then extracted with ether. Normal workup yielded 20.22 g (86%) of product as a bright yellow oil. Chromatography on silica gel (1% ethyl acetate/cyclohexane) yielded 12.24 g (52%) of product as a colorless oil; $n_D^{25}$ 1.472.

| Elemental Analysis: | C | H | N | Br |
|---|---|---|---|---|
| Calculated | 40.02 | 3.36 | 3.59 | 20.48 |
| Found | 40.15 | 3.37 | 3.58 | 20.42 |

EXAMPLE 123

3-Pyridinecarboxylic acid, 5-amino-6-(difluoromethyl)-4-(2-methylpropyl)-2-(trifluoromethyl) -, methyl ester. To a stirred slurry of 26.9 g (0.414 mol) of sodium azide, 47 ml of water and 158 ml acetone was slowly added a solution of 62.53 g (0.168 mol) of methyl 5-chlorocarbonyl-6-(difluoromethyl)-4-(2-methylpropyl)-2-(trifluoromethyl)-3-pyridinecarboxylate in 21 ml of acetone. An exothermic reaction followed with vigorous gas evolution. The reaction was allowed to cool to room temperature and diluted with 565 ml water and extracted with chloroform (3×100 ml). Workup as usual gave 52.9 g (97%) of product as a light yellow solid. Chromatography on silica gel (20% ethyl acetate/cyclohexane to elute product) gave 37.25 g (68%) of analytically pure material, mp 104°-106° C.

| Elemental Analysis: | C | H | N |
|---|---|---|---|
| Calculated | 47.86 | 4.63 | 8.59 |
| Found | 47.78 | 4.68 | 8.56 |

EXAMPLE 124

3-Pyridinecarboxylic acid, 6-(difluoromethyl)-5-[(methoxymethylene)amino]-4-(2-methylpropyl)-2-(trifluoromethyl)-, methyl ester. A solution of 3.25 g (0.01 mol) of product of Example 123, 6.0 ml of trimethyl orthoformate, and 60 mg of p-toluenesulfonic acid was stirred for 28 hours at 100° C. The reaction mixture was concentrated in vacuo and kugelrohr distilled (145°-155° C. at 1 torr) to yield 3.39 g (92%) of product as a colorless oil. Chromatography of product on silica gel (2% ethyl acetate/cyclohexane) gave analytically pure material; $n_D^{25}$ 1.466.

| Elemental Analysis: | C | H | N |
|---|---|---|---|
| Calculated | 48.92 | 4.65 | 7.61 |
| Found | 48.84 | 4.69 | 7.61 |

EXAMPLE 125

3-Pyridinecarboxylic acid, 6-(difluoromethyl)-5-[(ethoxymethylene)amino]-4-(2-methylpropyl) -2-(trifluoromethyl)-, methyl ester. A solution of 3.25 g (0.010 mol) of product of Example 123, 6.2 ml of triethyl orthoformate and 62 mg of p-toluenesulfonic acid was stirred at 100° C. for 8 hours. An additional 62 mg of p-toluenesulfonic acid was added and the reaction was complete 20 hours later. The reaction mixture was concentrated in vacuo and kugelrohr distilled (135°-145° C. at 1 torr) to give 3.8 g (99%) of product as a colorless oil; $n_D^{25}$ 1.4655.

| Elemental Analysis: | C | H | N |
|---|---|---|---|
| Calculated | 50.26 | 5.01 | 7.33 |
| Found | 50.32 | 5.02 | 7.23 |

EXAMPLE 126

3-Pyridinecarboxylic acid, 2-(difluoromethyl)-5-{(dimethylamino)methylene]amino}-4-ethyl-6-(trifluoromethyl)-, methyl ester. A stirred solution of 4.0 g (0.013 mol) of product of Example 115, 10 ml of dimethylformamide dimethyl acetal, and 70 mg of p-toluenesulfonic acid was refluxed overnight. The reaction mixture was concentrated in vacuo and kugelrohr distilled (170°-185° C. at 1 torr) to give 3.98 g (89%) of product as a yellow solid, mp 89°-91° C.

| Elemental Analysis: | C | H | N |
|---|---|---|---|
| Calculated | 47.60 | 4.56 | 11.89 |
| Found | 47.63 | 4.59 | 11.88 |

EXAMPLE 127

3-Pyridinecarboxylic acid, 6-(difluoromethyl)-5-{[(dimethylamino)methylene]amino}-4-(2-methylpropyl)-2-(trifluoromethyl)-, methyl ester. A stirred solution of 4.0 g (0.012 mol) of product of Example 123, 10 ml of dimethylformamide dimethyl acetal, and 70 mg p-toluenesulfonic acid was refluxed overnight. The reaction mixture was concentrated in vacuo and the residue kugelrohr distilled (170°-185° C. at 1 torr) to give 4.11 g (88%) of product as yellow liquid that slowly solidified, mp 59°-60° C.

| Elemental Analysis: | C | H | N |
|---|---|---|---|
| Calculated | 50.39 | 5.29 | 11.02 |
| Found | 50.41 | 5.28 | 10.98 |

EXAMPLE 128

3-Pyridinecarboxylic acid, 6-(difluoromethyl)-5-{[(dimethylamino)methylene]amino}-4-(2-methylpropyl)-2-(trifluoromethyl)-, ethyl ester. A solution of 4.0 g of product of Example 1, 9 ml of dimethylformamide dimethyl acetal, and 91 mg of p-toluenesulfonic acid was stirred at reflux for 3 hours. The reaction mixture was concentrated in vacuo and the residue kugelrohr distilled (185°-200° C. at 1 torr) to yield a brown oil. Chromatography on silica gel (7% ethyl acetate/cyclohexane) gave 3.29 g (71%) of product as a colorless oil; $n_D^{25}$ 1.486.

| Elemental Analysis: | C | H | N |
|---|---|---|---|
| Calculated | 51.64 | 5.61 | 10.63 |

| Elemental Analysis: | C | H | N |
|---|---|---|---|
| Found | 51.73 | 5.62 | 10.61 |

EXAMPLE 129

3-Pyridinecarboxylic acid, 5-azido-2-(difluoromethyl)-4-ethyl-6-(trifluoromethyl)-, methyl ester. To a 0° C. solution of 5.0 g (0.016 mol) of product of Example 115, 2.9 g (0.016 mol) of 48% fluoroboric acid, and 52 ml of acetonitrile was added 1.75 g (0.017 mol) of t-butyl nitrite dropwise. The reaction mixture was stirred at 0° C. for 20 minutes, then a solution of 2.72 g (0.042 mol) of sodium azide in 14 ml of water was added. Vigorous gas evolution followed. The reaction was stirred for 10 minutes at room temperature, then diluted with 100 ml of water and extracted with chloroform (3×25 ml). Normal workup afforded 5.07 g (98%) of product as an orange oil. Chromatography on silica gel (2% ethyl acetate/cyclohexane) gave 2.61 g (50%) of product as a colorless oil; $n_D^{25}$ 1.570.

| Elemental Analysis: | C | H | N |
|---|---|---|---|
| Calculated | 40.75 | 2.80 | 17.28 |
| Found | 40.82 | 2.77 | 17.10 |

EXAMPLE 130

3-Pyridinecarboxylic acid,5-(1-chloro-2,2,2-trifluoroethylidene)amino]-6-(difluoromethyl)-4-(2-methylpropyl)-2-(trifluoromethyl)-,ethyl ester. A mixture of 37.65 g (0.086 mol) of product of Example 7 and 17.97 g (1 equivalent) of PCl5 was stirred overnight at 130° C. in a flask fitted with a reflux condenser and a drying tube. The reaction mixture was concentrated in vacuo, then kugelrohr distilled at 90° C. to remove low-boiling impurities and finally at 130° C. to afford 35.78 g (0.078 mol) of product as a yellow oil which gradually solidified. Yield was 91%. mp 33.0°–34.0° C.

| Elemental Analysis: | C | H | N | Cl |
|---|---|---|---|---|
| Calculated | 42.26 | 3.32 | 6.16 | 7.80 |
| Found | 42.69 | 3.39 | 6.22 | 7.86 |

EXAMPLE 131

3-Pyridinecarboxylic acid, 6-(difluoromethyl)-4-{2-methylpropyl)-5-[(2,2,2-trifluoro-1-methoxyethylidene)amino]-2-(trifluoromethyl)-, ethyl ester. To a room temperature solution of 2.09 g (0.010 mol) of 25% sodium methoxide/methanol and 5 ml of methanol was added a solution of 4.0 g (0.009 mol) of product of Example 130 in 4.7 ml methanol. A yellow precipitate formed immediately and the reaction mixture was stirred at room temperature for 1 hour, then diluted with 25 ml of water and extracted with ether (3×20 ml). Workup as usual followed by kugelrohr distillation (135° C. at 1 torr) gave 2.57 g (65%) of product as a colorless oil. Chromatography on silica gel (0.5% ethyl acetate/cyclohexane) gave 1.89 g (48%) of pure product as a colorless oil; $n_D^{25}$ 1.438.

| Elemental Analysis: | C | H | N |
|---|---|---|---|
| Calculated | 45.34 | 4.03 | 6.22 |
| Found | 45.32 | 3.91 | 6.25 |

EXAMPLE 132

3-Pyridinecarboxylic acid, 6-(difluoromethyl)-4-(2-methylpropyl)-2-(trifluoromethyl)-5-[(2,2,2-trifluoro-1-ethoxyethylidine)amino]-, ethyl ester. To a solution of 3.24 g (0.010 mol) of 21% sodium ethoxide/ethanol and 5 ml of ethanol was added a solution of 4.0 g (0.009 mol) of product of Example 130 in 5 ml ethanol. The reaction was stirred at room temperature for 15 minutes. The reaction mixture was diluted with 100 ml water and extracted with ether (3×25 ml) which was worked up as usual. Kugelrohr distillation (135°–145° C. at 1 torr) gave 2.87 g (70%) of product as a colorless oil. Chromatography on silica gel (1% ethyl acetate/cyclohexane) gave 1.89 g (46%) of product as a colorless oil; $n_D^{25}$ 1 439.

| Elemental Analysis: | C | H | N |
|---|---|---|---|
| Calculated | 46.56 | 4.34 | 6.03 |
| Found | 46.64 | 4.34 | 6.14 |

EXAMPLE 133

3-Pyridinecarboxylic acid, 5-{[1-(dimethylamino)-2,2,2-trifluoroethylidene]amino]-6-(difluoromethyl)-4-(2-methylpropyl)-2-(trifluoromethyl)-, ethyl ester. To a room temperature solution of 4.0 g (0.009 mol) of product of Example 130 and 10 ml of dioxane was added 4.5 ml (0.026 mol) of 26% aqueous solution of dimethylamine. The solution became warm and was stirred for 30 minutes. The reaction mixture was diluted with 250 ml of water and extracted with chloroform (3×30 ml). Workup as usual gave a brown oil which was kugelrohr distilled (165° C. at 1 torr) to give 2.06 g (50%) of product as a yellow oil; $n_D^{25}$ 1.467.

| Elemental Analysis: | C | H | N |
|---|---|---|---|
| Calculated | 46.66 | 4.57 | 9.07 |
| Found | 46.44 | 4.56 | 9.01 |

EXAMPLE 134

3-Pyridinecarboxylic acid, 6-(difluoromethyl)-5-{1-(methylamino)-2,2,2-trifluoroethylidene]amino}-4-(2-methylpropyl)-2-(trifluoromethyl)-, ethyl ester. To a room temperature solution of 4.0 g (0.009 mol) of product of Example 130 in 10 ml dioxane was added 2 ml (0.026 mol) of 40% aqueous methylamine. The reaction became warm and was stirred for 30 minutes. The reaction mixture was diluted with 250 ml of water and extracted with chloroform (3×30 ml). Normal workup gave a yellow oil which was kugelrohr distilled (175° C. at 1 torr) to yield product as a thick yellow oil; $n_D^{25}$ 1.454.

| Elemental Analysis: | C | H | N |
|---|---|---|---|
| Calculated | 45.44 | 4.26 | 9.35 |
| Found | 45.54 | 4.27 | 9.18 |

EXAMPLE 135

Ethyl 2,6-bis-(trifluoromethyl)-5-bromo-4-hydroxy-3-pyridinecarboxylate. The precursor ethyl 2,6-bis(trifluoromethyl)-4-hydroxy-3-pyridinecarboxylate was prepared as follows:

To a flame dried 3-liter, four-necked flask equipped with nitrogen inlet, low temperature thermometer, 500 ml addition funnel and mechanical stirrer was charged 91.0 g (126 ml, 0.899 mol) of diisopropylamine and 500 ml of dry tetrahydrofuran. The resulting solution was cooled to −78° C. using an acetone-dry ice bath. To this was slowly added 383 ml (0.880 mol) of 2.3M n-BuLi in hexane at such a rate that the reaction temperature was kept below −60° C. After stirring at −78° C. for 1 hour, a solution of 90.0 g (0.400 mol) of ethyl 2-acetyl-3-amino-4,4,4-trifluoro 2-butenoate in 150 ml of dry tetrahydrofuran was added in such a rate that the reaction temperature was kept below −60° C. The reaction mixture turned yellow and a solid suspension formed.

After 1 hour of stirring at −78° C., the reaction mixture was treated with 184.7 g (155 ml, 1.300 mol) of ethyl trifluoroacetate in such rate that the reaction temperature was kept below −60° C. This reaction mixture was left at −78° C. for 1 hour, then warmed to room temperature (the yellow suspension disappeared and a brown solution was formed) and stirred for 18 hours. The resulting solution was poured into 1.5 L of 10% HcL (aqueous) and extracted 3 times with methylene chloride. The combined methylene chloride layers were dried (MgSO$_4$) and reduced in vacuo affording a thick brown oil. The residue was kugelrohr distilled at 47 Pa. The earlier fraction (pot temperature 50° C.) was discarded. The later fraction (pot temperature 80° C.) afforded 80.0 g (66%) of the pyridine intermediate; mp 70°–77° C.

To a solution of 5.0 g (0.165 mol) of the compound prepared above in 50 mL of 10% NaOH was added 5 mL of bromine. An exothermic reaction occurred instantly. The reaction mixture was stirred for 5 minutes and poured into a mixture of 20 mL of concentrated HCl and 50 mL of water. To the above mixture was added sodium sulfite until all red bromine color disappeared. The white oil precipitate was extracted into ether. The ether solution was dried and concentrated. The residue was kugelrohr distilled at 0.8 mm (pot temperature 95° C.) to give 5.7 g of an oil which was crystallized from petroleum ether at low temperature to give 3.5 g (55.9%) of product, mp 30°–32° C., which turned into a liquid upon standing, n$_D^{25}$, 1.4646.

| Elemental Analysis: | C | H | N | Br |
|---|---|---|---|---|
| Calculated | 31.44 | 1.58 | 3.67 | 20.92 |
| Found | 31.30 | 1.59 | 3.64 | 20.86 |

Using preparative techniques similar to those set out in detail above in Examples 1 through 136, additional compounds were prepared. These additional compounds are shown in the following Table 1, along with a physical property for each where available.

TABLE 1

| Example | R$_1$ | R$_2$ | R | Ra | X | MP(°C.) | n$_D^{25}$ |
|---|---|---|---|---|---|---|---|
| 136 | CF$_3$ | CF$_2$H | OCH$_3$ | —N=CH—S—CH$_3$ | Cyclobutyl | 59.8–64.8 | |
| 137 | CF$_3$ | CF$_2$H | OCH$_2$CH$_3$ | Br | Isobutyl | | 1.473 |
| 138 | CF$_3$ | CF$_2$H | OCH$_3$ | —N=CH—S—CH$_2$CH$_3$ | Cyclobutyl | | |
| 139 | CF$_3$ | CF$_3$ | OCH$_2$CH$_3$ | NH$_2$ | Methoxy | 70.0–71.0 | |
| 140 | CF$_3$ | CF$_3$ | OCH$_2$CH$_3$ | Br | Methoxy | | 1.449 |
| 141 | CF$_3$ | CF$_3$ | OCH$_2$CH$_3$ | I | Methoxy | 39.0–40.0 | |
| 142 | CF$_3$ | CF$_2$H | SCH$_3$ | N=C(CH$_3$)(SCH$_3$) | Isobutyl | | 1.518 |
| 143 | CF$_3$ | CF$_2$H | SCH$_3$ | N=CH—OCH$_2$CH$_3$ | Cyclopropylmethyl | | 1.480 |
| 144 | CF$_3$ | CF$_2$H | SCH$_3$ | N=C(CH$_3$)(N(CH$_3$)$_2$) | Isobutyl | 96.0–97.0 | |
| 145 | CF$_3$ | CF$_2$H | OCH$_3$ | Br | Cyclobutyl | 50.0–54.0 | |
| 146 | CF$_3$ | CF$_2$H | OCH$_3$ | N=C(CH$_3$)(OCH$_3$) | Cyclobutyl | 83.0–83.7 | |
| 147 | CF$_3$ | CF$_2$H | OCH$_3$ | Br | Isobutyl | | 1.471 |
| 148 | CF$_3$ | CH$_3$ | OCH$_2$CH$_3$ | NH$_2$ | Isobutyl | 94.0–96.0 | |
| 149 | CF$_3$ | CH$_3$ | OCH$_2$CH$_3$ | N=CHOCH$_3$ | Isobutyl | | 1.477 |
| 150 | CF$_3$ | CH$_3$ | OCH$_2$CH$_3$ | Br | Isobutyl | | 1.483 |

TABLE 1-continued $$\text{structure with substituents } R_a, R_2, R_1, X, \text{ and } C(=O)-R \text{ on pyridine ring}$$

| Example | R₁ | R₂ | R | Ra | X | MP(°C.) | $n_D^{25}$ |
|---|---|---|---|---|---|---|---|
| 151 | CF₃ | CF₂H | OCH₂CH₃ | N=CH—C₆H₄—CF₃ | Propyl | 82.0–84.0 | |
| 152 | CF₃ | CF₂H | OCH₃ | N=C(CH₃)N(CH₃)₂ | Cyclobutyl | | |
| 153 | CF₃ | CF₂H | OCH₂CH₃ | N=S=O | Propyl | | 1.476 |
| 154 | CF₃ | CF₂H | SCH₃ | N=C(CH₃)OCH₃ | Isobutyl | | 1.493 |
| 155 | CF₃ | CF₂H | OCH₂CH₃ | N=C(CH₃)P(=O)(OCH₂CH₃)₂ | Isobutyl | | 1.442 |
| 156 | CF₂H | CF₃ | OCH₃ | N=CH—N(CH₃)₂ | Isobutyl | 54.0–57.0 | |
| 157 | CF₃ | CH₃ | OCH₂CH₃ | N=CH—N(CH₃)₂ | Isobutyl | | 1.497 |
| 158 | CF₃ | CF₂H | OCH₂CH₃ | NHCH₃ | Isobutyl | | 1.473 |
| 159 | CF₃ | CH₃ | OCH₂CH₃ | NO₂ | Isobutyl | | 1.465 |
| 160 | CF₂H | CF₃ | OCH₃ | NO₂ | Ethyl | | 1.451 |
| 161 | CF₃ | CF₂H | SCH₃ | N=C(CH₃)NHCH₃ | Isobutyl | | 1.502 |
| 162 | CF₃ | CF₂H | OCH₃ | N=C=O | Isobutyl | | 1.466 |
| 163 | CF₃ | CF₂H | OCH₃ | N=S=O | Isobutyl | | 1.479 |
| 164 | CF₃ | CF₂H | OCH₂CH₃ | N=C(CH₃)N(CH₃)₂ | Propyl | 64.0–66.0 | |
| 165 | CF₂H | CF₃ | OCH₃ | N=S=O | Isobutyl | | 1.482 |
| 166 | CF₃ | CF₂H | OCH₃ | NH—C(=O)CH₃ | Isobutyl | 168.0–171.0 | |
| 167 | CF₃ | CF₂H | OCH₂CH₃ | N=C(F)CF₃ | Isobutyl | | 1.418 |
| 168 | CF₃ | CF₂H | SCH₃ | NH₂ | Isobutyl | 108.0–110.0 | |
| 169 | CF₃ | CF₂H | OCH₂CH₃ | NHCHO | Isobutyl | 90.0–92.0 | |
| 170 | CF₃ | CF₂H | SCH₃ | N=CHN(CH₃)₂ | Isobutyl | 70.0–71.0 | |
| 171 | CF₃ | CF₂H | SCH₃ | N=CHOCH₃ | Isobutyl | | 1.494 |
| 172 | CF₃ | CF₂H | SCH₃ | N=CHOCH₂CH₃ | Isobutyl | | 1.492 |
| 173 | CF₃ | CF₂H | OCH₂CH₃ | N=CHSCH₃ | Isobutyl | | 1.4925 |
| 174 | CF₃ | CF₂H | OCH₃ | NHCHO | Isobutyl | 118.0–120.0 | |
| 175 | CF₃ | CF₂H | OCH₂CH₃ | N=S=O | Isobutyl | | 1.477 |

TABLE 1-continued

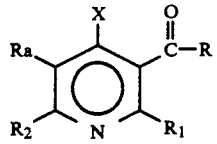

| Example | R₁ | R₂ | R | Ra | X | MP(°C.) | $n_D^{25}$ |
|---|---|---|---|---|---|---|---|
| 176 | $CF_3$ | $CF_2H$ | $SCH_3$ | Br | Isobutyl | 37.0–38.0 | |
| 177 | $CF_3$ | $CF_2H$ | $OCH_2CH_3$ | 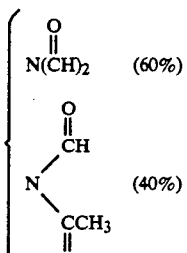 (60%) / 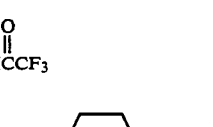 (40%) | Isobutyl | | |
| 178 | $CF_3$ | $CF_2H$ | $OCH_3$ | $N=CHSCH_3$ | Isobutyl | | 1.493 |
| 179 | $CF_3$ | $CF_2H$ | $OCH_3$ | $N(CHO)_2$ | Isobutyl | | 1.457 |
| 180 | $CF_3$ | $CF_2H$ | $OCH_3$ | $N=CHSCH_2CH_3$ | Isobutyl | | 1.493 |
| 181 | $CF_2H$ | $CF_3$ | $OCH_3$ |  NHCCF₃ | Isobutyl | 182.0–184.0 | |
| 182 | $CF_3$ | $CF_2H$ | $OCH_3$ | 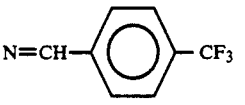 | Isobutyl | | 1.488 |
| 183 | $CF_2H$ | $CF_3$ | $OCH_3$ | 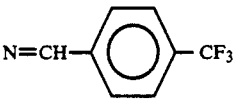 | Isobutyl | | 1.494 |
| 184 | $CF_3$ | $CF_2H$ | $OCH_3$ | 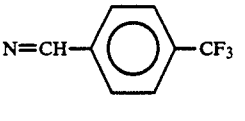 | Isobutyl | 112.0–114.0 | |
| 185 | $CF_3$ | $CF_2H$ | $OCH_3$ | 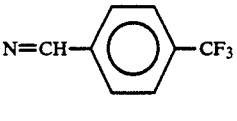 | Isobutyl | | 1.483 |
| 186 | $CF_2H$ | $CF_3$ | $OCH_3$ | 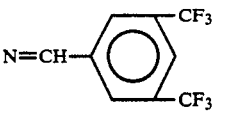 NHCCF₂CF₃ | Isobutyl | 160.0–161.0 | |
| 187 | $CF_2H$ | $CF_3$ | $SCH_3$ | Br | Isobutyl | | 1.507 |
| 188 | $CF_3$ | $CF_2H$ | $SCH_2CH_3$ | $N=CH-N(CH_3)_2$ | Isobutyl | | 1.511 |
| 189 | $CF_3$ | $CF_2H$ | $OCH_3$ | 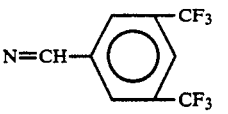 | Isobutyl | | 1.470 |
| 190 | $CF_3$ | $CF_2H$ | $OCH_3$ | 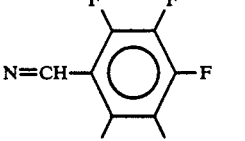 | Isobutyl | | 1.4845 |
| 191 | $CF_3$ | $CF_2H$ | $OCH_3$ | 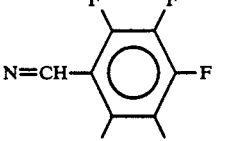 | Isobutyl | | 1.462 |

TABLE 1-continued

![structure: pyridine with Ra at 4-position, X at 3-position, C(=O)-R at... actually the structure shows Ra-C=C with X, C(=O)R, R2, N, R1]

| Example | R₁ | R₂ | R | Ra | X | MP(°C.) | $n_D^{25}$ |
|---|---|---|---|---|---|---|---|
| 192 | CF₃ | CF₂H | OCH₃ | N=C(CH₃)(NHCH₃) | Isobutyl | | 1.477 |
| 193 | CF₃ | CF₂H | OCH₃ | N=CFCH₃ | Isobutyl | 158.0–160.0 | |
| 194 | CF₃ | CF₂H | OCH₃ | N=C(CH₃)(SCH₃) | Isobutyl | | 1.492 |
| 195 | CF₃ | CF₂H | OCH₃ | NHC(O)CH₃ | Isobutyl | 118.0–119.0 | |
| 196 | CF₃ | CF₂H | SCH₃ | N=CHSCH₃ | Isobutyl | | 1.523 |
| 197 | CF₃ | CF₂H | SCH₃ | NHCOCH₃ | Isobutyl | 140.0–142.0 | |
| 198 | CF₃ | CF₂H | SCH₃ | NH₂ | Cyclopropylmethyl | 90.0–92.0 | |
| 199 | CF₃ | CF₂H | SCH₃ | N=CHN(CH₃)₂ | Cyclopropylmethyl | 109.0–112.0 | |
| 200 | CF₃ | CF₂H | OCH₃ | N=CHOCH₃ | Cyclobutyl | 64.0–66.0 | |
| 201 | CF₃ | CF₂H | OCH₃ | N=CHOCH₂CH₃ | Cyclobutyl | 48.0–52.0 | |
| 202 | CF₃ | CF₂H | OCH₃ | N=CHN(CH₃)₂ | Cyclobutyl | 86.6–88.4 | |
| 203 | CF₃ | CF₂H | OCH₃ | NH₂ | Cyclobutyl | 88.8–90.5 | |
| 204 | CF₂H | CF₃ | OCH₃ | NH₂ | Cyclobutyl | 89.0–92.8 | |
| 205 | CF₂H | CF₃ | OCH₃ | N=CHOCH₃ | Cyclobutyl | | |
| 206 | CF₂H | CF₃ | OCH₃ | N=CHOCH₂CH₃ | Cyclobutyl | | |
| 207 | CF₂H | CF₃ | OCH₃ | N=CHN(CH₃)₂ | Cyclobutyl | 69.0–74.0 | |
| 208 | CF₂H | CF₃ | OCH₃ | Br | Cyclobutyl | | |

EXAMPLE 209

3-Pyridinecarboxylic acid, 5-amino-2-(difluoromethyl) -4-(2-methylpropyl)-6-(trifluoromethyl)-, methyl ester. To a stirred slurry of 27.8 g of sodium azide, 50 ml of water and 164 ml of acetone was slowly added a solution of 65.2 g (0.183 mol) of methyl 5-chlorocarbonyl-6-(difluoromethyl)-4-(2-methylpropyl)-2-(trifluoromethyl)-3-pyridinecarboxylate in 16 ml of acetone. An exothermic reaction followed with vigorous gas evolution. The reaction mixture was allowed to cool to room temperature and diluted with water (500 ml) and extracted into chloroform (3 × 100 ml). Normal workup afforded 51.93 g (94%) of product as green solid. Chromatography on silica gel (10% ethyl acetate/cyclohexane) gave analytically pure material, mp 48°–50° C.

| Elemental Analysis: | C | H | N |
|---|---|---|---|
| Calculated | 47.86 | 4.63 | 8.59 |
| Found | 47.81 | 4.63 | 8.58 |

PRE-EMERGENT HERBICIDE EXAMPLES

As noted above, many of the compounds of this invention have been found to be effective as pre-emergent and post-emergent herbicides. Table 2 summarizes results of tests conducted to determine the pre-emergent herbicidal activity of the compounds of this invention on common weeds.

The pre-emergent tests are conducted as follows:

Top soil is placed in aluminum pans and compacted to a depth of 0.95 to 1.27 cm. from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in acetone as a solvent is thoroughly mixed with the soil, and the herbicide/soil mixture is used as a cover layer for prepared pans. In Table 3 below the amount of active ingredient is equal to the rate of 11.2 kg/ha. After treatment, the pans are moved to a greenhouse bench where they are watered from below as needed to give adequate moisture for germination and growth.

Approximately 10 –14 days (usually 11 days) after seeding and treating, the pans are observed and the results recorded. In some instances, a second observation is made approximately 24–28 days after seeding and treating, and these observations are indicated in the following tables by an asterisk (*) immediately following the Example number.

Table 2 below summarizes the results of the pre-emergent herbicidal activity tests of compounds of this invention in weeds.

The herbicidal rating is obtained by means of a fixed scale based on the percent inhibition of each plant species. The symbols in the Table are defined as follows:

| % Inhibition | Rating |
|---|---|
| 0–24 | 0 |
| 25–49 | 1 |
| 50–74 | 2 |
| 75–100 | 3 |
| Not planted | — |

| % Inhibition | Rating |
|---|---|
| Species planted, no data | N |

WEED-PLANT HERBICIDE ACTIVITY

The plant species usually regarded as weeds which are utilized in one set of test, the data for which are shown in Table 3, are identified by letter headings above the columns in accordance with the following legend:

A - Canada thistle*
B - Cocklebur
C - Velvetleaf
D - Morningglory
E - Common Lambsquarters
F - Pennsylvania Smartweed
G - Yellow Nutsedge*
H - Quackgrass*
I - Johnsongrass*
J - Downy Brome
K - Barnyardgrass

*Grown from vegetative propagules

TABLE 2
PRE-EMERGENT ACTIVITY FOR WEEDS

| Example No. | Kg/ha | A | B | C | D | E | F | G | H | I | J | K |
|---|---|---|---|---|---|---|---|---|---|---|---|---|
| 1 | 11.2 | 0 | 0 | 1 | 2 | 3 | 3 | 0 | 3 | 0 | 3 | 3 |
| 2 | 11.2 | 0 | 0 | 3 | 3 | 3 | 3 | 0 | 2 | — | 3 | 3 |
| 3 | 11.2 | 0 | 0 | 1 | 2 | 3 | 2 | 0 | 3 | 3 | 1 | 3 |
| 4 | 11.2 | 0 | 0 | 0 | 0 | 1 | 3 | 0 | 0 | 3 | 0 | 1 |
| 5 | 11.2 | 3 | 2 | 3 | 3 | 3 | 3 | 2 | 2 | 3 | 3 | 3 |
| 6 | 11.2 | 0 | 0 | 3 | 1 | 3 | 3 | 0 | 0 | 3 | 3 | 3 |
| 7 | 11.2 | 3 | 0 | 2 | 3 | 3 | 2 | 0 | 0 | 3 | 2 | 2 |
| 8 | 11.2 | 0 | 0 | 0 | 0 | 0 | 1 | 0 | 3 | 3 | 3 | 3 |
| 9 | 11.2 | 3 | 0 | 2 | 3 | 3 | 3 | 0 | 1 | N | 3 | 3 |
| 10 | 11.2 | 3 | N | 1 | 3 | 3 | 2 | 1 | 3 | 3 | 3 | 3 |
| 11 | 11.2 | 0 | 1 | 1 | 3 | 2 | 2 | 0 | 3 | 3 | 3 | 3 |
| 12 | 11.2 | 3 | 1 | 1 | 3 | 3 | 0 | 0 | 3 | — | 3 | 3 |
| 13 | 11.2 | 3 | 1 | 2 | 3 | 3 | 3 | 0 | 3 | 3 | 3 | 3 |
| 14 | 11.2 | 3 | 0 | 2 | 3 | 3 | 3 | 3 | 3 | — | 3 | 3 |
| 15 | 11.2 | 1 | 1 | 3 | 3 | 3 | 3 | 2 | 3 | 3 | 3 | 3 |
| 16 | 11.2 | 3 | 0 | 3 | 3 | 3 | 3 | 0 | 1 | 0 | 2 | 3 |
| 17 | 11.2 | — | 1 | 3 | 3 | 3 | 3 | 0 | 3 | 2 | 3 | 3 |
| 18 | 11.2 | — | N | 0 | 0 | 3 | 0 | 0 | 0 | 0 | 0 | 1 |
| 19 | 11.2 | — | 0 | 1 | 2 | 3 | 3 | 0 | 3 | 3 | 3 | 3 |
| 20 | 11.2 | — | 1 | 0 | 0 | 1 | 0 | 0 | 0 | 0 | 0 | 1 |
| 21 | 11.2 | — | 0 | 0 | 0 | 0 | 0 | 0 | 0 | 0 | 2 | 0 |
| 22 | 11.2 | — | 0 | 0 | 0 | 2 | 0 | 0 | 0 | 2 | 2 | 2 |
| 23 | 11.2 | — | 1 | 1 | 0 | 0 | 1 | 1 | 0 | 1 | 0 | 1 |
| 24 | 11.2 | — | 0 | 0 | 0 | 0 | 0 | 0 | 3 | 0 | 0 | 0 |
| 25 | 11.2 | 1 | N | 1 | 0 | 3 | 1 | 0 | 0 | 0 | 0 | 2 |
| 26 | 11.2 | — | 0 | 2 | 0 | 3 | 2 | 0 | 0 | 0 | 1 | 2 |
| 26* | 11.2 | — | 0 | 2 | 0 | 3 | 1 | 0 | 0 | 0 | 1 | 2 |
| 27 | 11.2 | — | 0 | 3 | 3 | N | 3 | 0 | 0 | 0 | 0 | 0 |
| 28 | 11.2 | — | 2 | 3 | 3 | 3 | 0 | 0 | 1 | 1 | 1 | 1 |
| 29 | 11.2 | — | 0 | 0 | 0 | 2 | 2 | 0 | 0 | 3 | 3 | 3 |
| 30 | 11.2 | — | 0 | 0 | 0 | 0 | 0 | 0 | 0 | 0 | 1 | 0 |
| 31 | 11.2 | — | 2 | 2 | 0 | 0 | 3 | 0 | 0 | 0 | 1 | 3 |
| 32 | 11.2 | — | 3 | 3 | 3 | 3 | 3 | 0 | 3 | 3 | 3 | 3 |
| 33 | 11.2 | — | 1 | 3 | 3 | 3 | 3 | 0 | 3 | 3 | 3 | 3 |
| 34 | 11.2 | — | 0 | 3 | 3 | 3 | 3 | 0 | 3 | 3 | 3 | 3 |
| 35 | 11.2 | — | 2 | 3 | 3 | 3 | 3 | 2 | 3 | 3 | 3 | 3 |
| 36 | 11.2 | — | 0 | 3 | 3 | 3 | 3 | 0 | 3 | 0 | 3 | 3 |
| 37 | 11.2 | — | 0 | 3 | 3 | 3 | 2 | 0 | 3 | 0 | 3 | 3 |
| 38 | 11.2 | — | 1 | 3 | 3 | 3 | 3 | 1 | 3 | 3 | 3 | 3 |
| 39 | 11.2 | — | 2 | 3 | 3 | 3 | 3 | 2 | 3 | 3 | 3 | 3 |
| 40 | 11.2 | — | 0 | 3 | 3 | 3 | 3 | 0 | 3 | 3 | 3 | 3 |
| 41 | 11.2 | — | 0 | 0 | 0 | 3 | 3 | 0 | 0 | N | 0 | 3 |
| 42 | 11.2 | — | 0 | 2 | 2 | 3 | 0 | 0 | 0 | N | 1 | 3 |
| 43 | 11.2 | — | 0 | 0 | 0 | 3 | 3 | 0 | 0 | 0 | 3 | 3 |
| 44 | 11.2 | — | 0 | 0 | 0 | 3 | 0 | 0 | 0 | 0 | 0 | 3 |
| 45 | 11.2 | — | 0 | 1 | 0 | 3 | 3 | 0 | 0 | 0 | 3 | 3 |
| 46 | 11.2 | — | 1 | 0 | 0 | 3 | 3 | 1 | 0 | 0 | 1 | 0 |
| 47 | 11.2 | — | 1 | 1 | 1 | 3 | 3 | 0 | 0 | 0 | 1 | 0 |
| 48 | 11.2 | — | 0 | 0 | 2 | 1 | 3 | 0 | 1 | 0 | 3 | 3 |
| 49 | 11.2 | — | 1 | 1 | 1 | 3 | 3 | 0 | 3 | 3 | 3 | 3 |
| 50 | 11.2 | — | 0 | 0 | 0 | 1 | 2 | 0 | 1 | 0 | 3 | 3 |
| 51 | 11.2 | — | 0 | 1 | 0 | 3 | 1 | 0 | 0 | 0 | 0 | 0 |
| 52 | 11.2 | — | 0 | 1 | 1 | 3 | 3 | 0 | 2 | 0 | 3 | 3 |
| 53 | 11.2 | — | 0 | 2 | 3 | 3 | 3 | 0 | 3 | 1 | 3 | 3 |
| 54 | 11.2 | — | 3 | 3 | 3 | 3 | 3 | 1 | 3 | 1 | 3 | 3 |
| 55 | 11.2 | — | 0 | 2 | 2 | 1 | 2 | 0 | 3 | 0 | 3 | 3 |
| 56 | 11.2 | — | 0 | 1 | 3 | 3 | 3 | 0 | 2 | 0 | 3 | 3 |
| 57 | 11.2 | — | 1 | 3 | 3 | 3 | 3 | 0 | 3 | 1 | 3 | 3 |
| 58 | 11.2 | — | 0 | 2 | 1 | 3 | 2 | 0 | 3 | 0 | 3 | 3 |
| 59 | 11.2 | — | 1 | 2 | 1 | 2 | 2 | 0 | 0 | 0 | 1 | 3 |
| 60 | 11.2 | — | 0 | 2 | 1 | 3 | 3 | 0 | 0 | 0 | 3 | 3 |
| 61 | 11.2 | — | 0 | 0 | 0 | 1 | 0 | 0 | 0 | 0 | 0 | 3 |
| 62 | 11.2 | — | 0 | 0 | 0 | 0 | 0 | 0 | 0 | 0 | 0 | 2 |
| 63 | 11.2 | — | 0 | 1 | 0 | 3 | 2 | 0 | 2 | 0 | 2 | 3 |
| 64 | 11.2 | — | 0 | 0 | 0 | 0 | 1 | 0 | 3 | 1 | 0 | 3 |
| 65 | 11.2 | — | 0 | 3 | 0 | 1 | 1 | 0 | 2 | 0 | 0 | 3 |
| 66 | 11.2 | — | 3 | 0 | 0 | 0 | 0 | 0 | 0 | 3 | 0 | 0 |
| 67 | 11.2 | — | 0 | 2 | 0 | 0 | 0 | 0 | 1 | N | 0 | 0 |
| 68 | 11.2 | — | 3 | 3 | 3 | 3 | 3 | 0 | 0 | 0 | 3 | 3 |
| 69 | 11.2 | — | 3 | 0 | 3 | 3 | 2 | 0 | 0 | 0 | 1 | 3 |
| 70 | 11.2 | — | 0 | 0 | 0 | 0 | 0 | 0 | 0 | 0 | 0 | 0 |
| 71 | 11.2 | 0 | 1 | 3 | 3 | 3 | 3 | 0 | 1 | 1 | 2 | 3 |
| 72 | 11.2 | 1 | 0 | 3 | 3 | 3 | 3 | 0 | 3 | 0 | 3 | 3 |
| 73 | 11.2 | 0 | 3 | 0 | 3 | 1 | 1 | 0 | 3 | 3 | 3 | 3 |
| 74 | 11.2 | 0 | 3 | 0 | 3 | 3 | 3 | 0 | 3 | 0 | 3 | 3 |
| 75 | 11.2 | 0 | 3 | 1 | 3 | 3 | 3 | 0 | 1 | 0 | 3 | 3 |
| 76 | 11.2 | — | 0 | 2 | 3 | 3 | 3 | 0 | 3 | 3 | 3 | 3 |
| 77 | 11.2 | — | 0 | 2 | 3 | 3 | 3 | 0 | 2 | 0 | 3 | 3 |
| 78 | 11.2 | — | 1 | 2 | 3 | 3 | 3 | 0 | 3 | 0 | 3 | 3 |
| 79 | 11.2 | — | 0 | 1 | 3 | 3 | 3 | 0 | 3 | 1 | 3 | 3 |
| 80 | 11.2 | — | 0 | 1 | 3 | 3 | 3 | 0 | 3 | 0 | 3 | 3 |
| 81 | 11.2 | — | 0 | 3 | 3 | 3 | 3 | 1 | 3 | 0 | 3 | 3 |
| 82 | 11.2 | — | 1 | 0 | 3 | 2 | 1 | 0 | 3 | 3 | 3 | 3 |
| 83 | 11.2 | — | 0 | 1 | 3 | 3 | 3 | 0 | 3 | 0 | 3 | 3 |
| 84 | 11.2 | — | 1 | 2 | 3 | 3 | 3 | 0 | 3 | 1 | 3 | 3 |
| 85 | 11.2 | — | 1 | 3 | 3 | 3 | 2 | 3 | 3 | 3 | 3 | 3 |
| 86 | 11.2 | — | 0 | 3 | 3 | 3 | 3 | 0 | 3 | 2 | 3 | 3 |
| 87 | 11.2 | — | 0 | 1 | 1 | 1 | 1 | 0 | 0 | N | 1 | 3 |
| 88 | 11.2 | — | 0 | 2 | 2 | 3 | 3 | 0 | 2 | N | 3 | 3 |
| 89 | 11.2 | — | 0 | 3 | 3 | 3 | 3 | 0 | 2 | 2 | 3 | 3 |
| 90 | 11.2 | — | 0 | 3 | 3 | 3 | 3 | 0 | 0 | 0 | 2 | 3 |
| 91 | 11.2 | — | 0 | 2 | 3 | 3 | 1 | 0 | 0 | N | 2 | 3 |
| 92 | 11.2 | — | 0 | 2 | 3 | 2 | 0 | 1 | 0 | 2 | 2 | 3 |
| 93 | 11.2 | — | 0 | 0 | 1 | 3 | 3 | 0 | 0 | 0 | 3 | 3 |
| 94 | 11.2 | — | 1 | 0 | 0 | 1 | 0 | 0 | 0 | 0 | 3 | 3 |
| 95 | 11.2 | — | 1 | 2 | 3 | 3 | 3 | 0 | 3 | 2 | 3 | 3 |
| 96 | 11.2 | — | 0 | 3 | 3 | 3 | 3 | 0 | 3 | 0 | 3 | 3 |
| 97 | 11.2 | — | 0 | 2 | 3 | 3 | 3 | 0 | 3 | 3 | 3 | 3 |
| 98 | 11.2 | 3 | 1 | 3 | 3 | 3 | 3 | 1 | 3 | 2 | 3 | 3 |
| 99 | 11.2 | — | 1 | 3 | 3 | 3 | 3 | 0 | 3 | 0 | 3 | 3 |
| 100 | 11.2 | — | 2 | 3 | 3 | 3 | 3 | 2 | 3 | 3 | 3 | 3 |
| 101 | 11.2 | 3 | 0 | 3 | 3 | 3 | 3 | 0 | 3 | 0 | 3 | 3 |
| 102 | 11.2 | 0 | 1 | 3 | 3 | 3 | 3 | 1 | 3 | 0 | 3 | 3 |
| 103 | 11.2 | 1 | 1 | 3 | 2 | 3 | 3 | 0 | 1 | 0 | 3 | 3 |
| 104 | 11.2 | 0 | 0 | 1 | 2 | 3 | 3 | 0 | 0 | 0 | 1 | 3 |
| 105 | 11.2 | 0 | 1 | 2 | 3 | 3 | 3 | 0 | 3 | 3 | 3 | 3 |
| 106 | 11.2 | 2 | 2 | 3 | 3 | 3 | 3 | 0 | 3 | 0 | 3 | 3 |
| 107 | 11.2 | 2 | 0 | 1 | 1 | 3 | 1 | 0 | 0 | 0 | 0 | 1 |
| 108 | 11.2 | 1 | 1 | 0 | 2 | 3 | 2 | 0 | 0 | 0 | 0 | 0 |
| 109 | 11.2 | 0 | 1 | 0 | 3 | 3 | 3 | 1 | 0 | 0 | 0 | 3 |
| 110 | 11.2 | 1 | 0 | 1 | 1 | 2 | 1 | 0 | 0 | 0 | 0 | 3 |
| 111 | 11.2 | 1 | 0 | 0 | 0 | 2 | 1 | 0 | 0 | 2 | 1 | 3 |
| 112 | 11.2 | 3 | 0 | 3 | 3 | 3 | 3 | 0 | 0 | 0 | 3 | 3 |
| 113 | 11.2 | 0 | 0 | 3 | 3 | 3 | 3 | 0 | 0 | 3 | 3 | 3 |
| 114 | 11.2 | 3 | 3 | 3 | 3 | 3 | 3 | 3 | 3 | 3 | 3 | 3 |
| 115 | 11.2 | 0 | 1 | 3 | 3 | 3 | 3 | 0 | 0 | 3 | 3 | 3 |
| 116 | 11.2 | 1 | 3 | 3 | 3 | 3 | 3 | 1 | 3 | 1 | 3 | 3 |
| 117 | 11.2 | 3 | 1 | 3 | 3 | 3 | 3 | 1 | 3 | 3 | 3 | 3 |
| 118 | 11.2 | 3 | 3 | 3 | 3 | 3 | 3 | 3 | 3 | 3 | 3 | 3 |
| 119 | 11.2 | 0 | 0 | 2 | 3 | 3 | 3 | 3 | 3 | 0 | 3 | 3 |
| 120 | 11.2 | 0 | 0 | 1 | 2 | 2 | 3 | 0 | 3 | 0 | 3 | 3 |
| 121 | 11.2 | 3 | 0 | 3 | 3 | 3 | 3 | 1 | 3 | 3 | 3 | 3 |
| 122 | 11.2 | 1 | 0 | 3 | 3 | 3 | 3 | 2 | 3 | 0 | 3 | 3 |
| 123 | 11.2 | 1 | 1 | 3 | 2 | 3 | 3 | 0 | 0 | 0 | 3 | 3 |

TABLE 2-continued

PRE-EMERGENT ACTIVITY FOR WEEDS

| Example No. | Kg/ha | A | B | C | D | E | F | G | H | I | J | K |
|---|---|---|---|---|---|---|---|---|---|---|---|---|
| 124 | 11.2 | 3 | 2 | 3 | 3 | 3 | 3 | 3 | 3 | 3 | 3 | 3 |
| 125 | 11.2 | 3 | 3 | 3 | 3 | 3 | 3 | 3 | 3 | 3 | 3 | 3 |
| 126 | 11.2 | 1 | 1 | 3 | 3 | 3 | 3 | 0 | 3 | 2 | 3 | 3 |
| 127 | 11.2 | 3 | 3 | 3 | 3 | 3 | 3 | 3 | 3 | 3 | 3 | 3 |
| 128 | 11.2 | 3 | 2 | 3 | 3 | 3 | 3 | 3 | 3 | 3 | 3 | 3 |
| 129 | 11.2 | 3 | 1 | 3 | 3 | 3 | 3 | 3 | 3 | 3 | 3 | 3 |
| 130 | 11.2 | 2 | 1 | 3 | 3 | 3 | 3 | 0 | 3 | 0 | 2 | 3 |
| 131 | 11.2 | 0 | 1 | 3 | 3 | 3 | 3 | 0 | 3 | 3 | 3 | 3 |
| 132 | 11.2 | 0 | 0 | 1 | 0 | 0 | 0 | 0 | 2 | 1 | 3 | 3 |
| 133 | 11.2 | 0 | 0 | 3 | 3 | 3 | 3 | 0 | 2 | 0 | 3 | 3 |
| 134 | 11.2 | 0 | 0 | 3 | 3 | 3 | 3 | 0 | 2 | 0 | 3 | 3 |
| 135 | 11.2 | 0 | 1 | 2 | 2 | 3 | 3 | 0 | N | 0 | 0 | 0 |
| 135* | 11.2 | 0 | 0 | 1 | 2 | 3 | 2 | 0 | N | 0 | 0 | 0 |
| 136 | 11.2 | 3 | 2 | 3 | 3 | 3 | 3 | 1 | 3 | 3 | — | 3 |
| 137 | 11.2 | 3 | 1 | 0 | 1 | 2 | 2 | 0 | 3 | — | 3 | 3 |
| 138 | 11.2 | 0 | 0 | 1 | 2 | 3 | 3 | 0 | 2 | 3 | — | 3 |
| 139 | 11.2 | 0 | 0 | 0 | 1 | 0 | 0 | 0 | 0 | 0 | 0 | 3 |
| 140 | 11.2 | 3 | 0 | 0 | 2 | 0 | 0 | 0 | 0 | N | 0 | 0 |
| 141 | 11.2 | 0 | 0 | 0 | 2 | 3 | 3 | 0 | 0 | N | 3 | 3 |
| 142 | 11.2 | 3 | 3 | 3 | 3 | 3 | 3 | 2 | 3 | 3 | — | 3 |
| 143 | 11.2 | 3 | 2 | 3 | 3 | 3 | 3 | 2 | 3 | 3 | — | 3 |
| 144 | 11.2 | 3 | 0 | 3 | 3 | 3 | 3 | 1 | 3 | 3 | — | 3 |
| 145 | 11.2 | 1 | 0 | 2 | 2 | 3 | 3 | 1 | 3 | 0 | — | 3 |
| 146 | 11.2 | 3 | 1 | 3 | 3 | 3 | 3 | 2 | 3 | 3 | — | 3 |
| 147 | 11.2 | 1 | 0 | 1 | 3 | 3 | 3 | 0 | 3 | 1 | 3 | 3 |
| 148 | 11.2 | 0 | 0 | 2 | 0 | 3 | 2 | 1 | 0 | 0 | 1 | 3 |
| 149 | 11.2 | 3 | 1 | 3 | 3 | 3 | 3 | 0 | 3 | 3 | 3 | 3 |
| 150 | 11.2 | 3 | 0 | 0 | 2 | 3 | 0 | 0 | 3 | 3 | 1 | 3 |
| 151 | 11.2 | 3 | 0 | 3 | 3 | 3 | 3 | 1 | 0 | 0 | 2 | 3 |
| 152 | 11.2 | 3 | 0 | 3 | 3 | 3 | 3 | 0 | 3 | 0 | — | 3 |
| 153 | 11.2 | 2 | 0 | 3 | 3 | 3 | 3 | 0 | 0 | 0 | 2 | 3 |
| 154 | 11.2 | 3 | 2 | 3 | 3 | 3 | 3 | 3 | 3 | 3 | 3 | 3 |
| 155 | 11.2 | 3 | 0 | 1 | 3 | 3 | 2 | 0 | 0 | 0 | 0 | 3 |
| 156 | 11.2 | 3 | 3 | 3 | 3 | 3 | 3 | 2 | 3 | 3 | 3 | 3 |
| 157 | 11.2 | 3 | 0 | 3 | 3 | 3 | 3 | 1 | 3 | 1 | 3 | 3 |
| 158 | 11.2 | 0 | 0 | 3 | 3 | 3 | 3 | 0 | 3 | 0 | 3 | 3 |
| 159 | 11.2 | 0 | 0 | 0 | 0 | 3 | 1 | 0 | 3 | 1 | 3 | 3 |
| 160 | 11.2 | 0 | 0 | 0 | 0 | 0 | 0 | 0 | 1 | 0 | 0 | 3 |
| 161 | 11.2 | 3 | 0 | 3 | 3 | 3 | 3 | 0 | 0 | 0 | — | 3 |
| 162 | 11.2 | 0 | 0 | 1 | 2 | 3 | 3 | 0 | 0 | 0 | 3 | 3 |
| 163 | 11.2 | 1 | 0 | 1 | 1 | 3 | 3 | 0 | 0 | 0 | 3 | 3 |
| 164 | 11.2 | 3 | 0 | 3 | 3 | 3 | 3 | 0 | 3 | 0 | 3 | 3 |
| 165 | 11.2 | 1 | 0 | 3 | 3 | 3 | 3 | 1 | 3 | 0 | 3 | 3 |
| 166 | 11.2 | 3 | 0 | 1 | 1 | 3 | 3 | 0 | 3 | 0 | 3 | 3 |
| 167 | 11.2 | 3 | 0 | 2 | 3 | 3 | 3 | 1 | 3 | 0 | 1 | 3 |
| 168 | 11.2 | 3 | 1 | 3 | 3 | 3 | 3 | 2 | 3 | 1 | 3 | 3 |
| 169 | 11.2 | 1 | 0 | 3 | 3 | 3 | 3 | 0 | 0 | 0 | 1 | 3 |
| 170 | 11.2 | 3 | 3 | 3 | 3 | 3 | 3 | 3 | 3 | 3 | 3 | 3 |
| 171 | 11.2 | 3 | 2 | 3 | 3 | 3 | 3 | 2 | 3 | 3 | 3 | 3 |
| 172 | 11.2 | 3 | 3 | 3 | 3 | 3 | 3 | 1 | 3 | 1 | 3 | 3 |
| 173 | 11.2 | 3 | 2 | 3 | 3 | 3 | 3 | 3 | 3 | 2 | 3 | 3 |
| 174 | 11.2 | 0 | 0 | 1 | 0 | 2 | 0 | 0 | 0 | 0 | 3 | 3 |
| 175 | 11.2 | 1 | 0 | 3 | 3 | 3 | 3 | 0 | 1 | 0 | 3 | 3 |
| 176 | 11.2 | 0 | 0 | 3 | 3 | 3 | 3 | 0 | 3 | 0 | 3 | 3 |
| 177 | 11.2 | 0 | 0 | 0 | 0 | 3 | 1 | 0 | 2 | 0 | 0 | 3 |
| 178 | 11.2 | 3 | 2 | 3 | 3 | 3 | 3 | 3 | 3 | 3 | 3 | 3 |
| 179 | 11.2 | 1 | 0 | 0 | 0 | 3 | 1 | 0 | 0 | 0 | 0 | 3 |
| 180 | 11.2 | 3 | 1 | 3 | 3 | 3 | 3 | 0 | 3 | 3 | 3 | 3 |
| 181 | 11.2 | 0 | 0 | 0 | 2 | 2 | 1 | 0 | 1 | 3 | 0 | 3 |
| 182 | 11.2 | 0 | 0 | 0 | 0 | 3 | 3 | 0 | 0 | 0 | 1 | 3 |
| 183 | 11.2 | 1 | 0 | 3 | 3 | 3 | 3 | 0 | 3 | 0 | 3 | 3 |
| 184 | 11.2 | 0 | 0 | 2 | 1 | 3 | 3 | 0 | 1 | 0 | 3 | 3 |
| 185 | 11.2 | 0 | 0 | 2 | 1 | 3 | 3 | 0 | 0 | 0 | 3 | 3 |
| 186 | 11.2 | 0 | 0 | 0 | 0 | 0 | 0 | 0 | 0 | 0 | 0 | 3 |
| 187 | 11.2 | 1 | 0 | 2 | 3 | 3 | 3 | 0 | 3 | 0 | 3 | 3 |
| 188 | 11.2 | 2 | 1 | 3 | 3 | 3 | 3 | 1 | 3 | 0 | 3 | 3 |
| 189 | 11.2 | 0 | 0 | 0 | 0 | 0 | 0 | 0 | 0 | 0 | 0 | 0 |
| 190 | 11.2 | 3 | 1 | 3 | 3 | 3 | 3 | 1 | 3 | 3 | 3 | 3 |
| 191 | 11.2 | 3 | 3 | 3 | 3 | 3 | 3 | 3 | 3 | 3 | N | 3 |
| 192 | 11.2 | 0 | 0 | 2 | 3 | 3 | 3 | 1 | 0 | 1 | 0 | N |
| 193 | 11.2 | 0 | 0 | 1 | 0 | 0 | 0 | 0 | 0 | 0 | N | 3 |
| 194 | 11.2 | 3 | 1 | 3 | 3 | 3 | 3 | 2 | 3 | 3 | 3 | 3 |
| 195 | 11.2 | 0 | 0 | 0 | 1 | 2 | 0 | 0 | 0 | 3 | 1 | 3 |
| 196 | 11.2 | 3 | 3 | 3 | 3 | 3 | 3 | 3 | 3 | 3 | 3 | 3 |
| 197 | 11.2 | 0 | 0 | 0 | 0 | 2 | 0 | 0 | 0 | N | 0 | 3 |
| 198 | 11.2 | 1 | 1 | 2 | 3 | 3 | 3 | 0 | 0 | 0 | 3 | 3 |
| 199 | 11.2 | 3 | 2 | 3 | 3 | 3 | 3 | 3 | 3 | 3 | 2 | 3 |
| 200 | 11.2 | 3 | 0 | 3 | 3 | 3 | 3 | 2 | 3 | 3 | 3 | 3 |
| 201 | 11.2 | 0 | 0 | 3 | 3 | 3 | 3 | 1 | 3 | 3 | 3 | 3 |
| 202 | 11.2 | 3 | 0 | 3 | 3 | 3 | 3 | 1 | 3 | 3 | 3 | 3 |
| 203 | 11.2 | 0 | 0 | 3 | 3 | 3 | 3 | 0 | 0 | 3 | 1 | 3 |
| 204 | 11.2 | 3 | 0 | 3 | 3 | 3 | 3 | 1 | 3 | 3 | 3 | 3 |
| 205 | 11.2 | 3 | 3 | 3 | 3 | 3 | 3 | 1 | 3 | 3 | 3 | 3 |
| 206 | 11.2 | 3 | 2 | 3 | 3 | 3 | 3 | 1 | 3 | 3 | 3 | 3 |
| 207 | 11.2 | 3 | 0 | 3 | 3 | 3 | 3 | 0 | 3 | 3 | 3 | 3 |
| 208 | 11.2 | 3 | 0 | 3 | 3 | 3 | 3 | 1 | 3 | 3 | 3 | 3 |

CHOP AND WEED PLANT HERBICIDE ACTIVITY

The compounds were further tested by utilizing the above procedure on the following plant species, i.e., on weeds in the presence of crop plants.

L - Soybean
M - Sugarbeet
N - Wheat
O - Rice
P - Grain Sorghum
B - Cocklebur
Q - Wild Buckwheat
D - Morningglory
R - Hemp Sesbania
E - Common Lambsquarters
F - Pennsylvania Smartweed
C - Velvetleaf
J - Downy Brome
S - Panicum spp.
K - Barnyardgrass
T - Large Crabgrass The results are summarized in Table 3.

TABLE 3

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 1 | 5.6 | 0 | 3 | 0 | 0 | 2 | 0 | 0 | 1 | 1 | 3 | 3 | 1 | 1 | 2 | 3 | 3 |
|  | 1.12 | 0 | 0 | 0 | 0 | 0 | 0 | 0 | 0 | 0 | 0 | 0 | 0 | 0 | 1 | 2 | 0 |
|  | 0.28 | 0 | 0 | 0 | 0 | 0 | 0 | 0 | 0 | 0 | 0 | 0 | 0 | 0 | 0 | 0 | 0 |
| 2 | 5.6 | 0 | 3 | 2 | 2 | 3 | 0 | 3 | 3 | 2 | 3 | 3 | 2 | 3 | 3 | 3 | 3 |
|  | 1.12 | 0 | 1 | 0 | 0 | 0 | 0 | 0 | 0 | 0 | 0 | 0 | 0 | 0 | 1 | 1 | 2 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 3 | 5.6 | 2 | 3 | 0 | 3 | 3 | 0 | 3 | 3 | 3 | 3 | 2 | 3 | 3 | 3 | 3 | 3 |
|  | 1.12 | 0 | 2 | 0 | 0 | 2 | 0 | 2 | 0 | 0 | 1 | 1 | 1 | 1 | 3 | 3 | 3 |
|  | 0.28 | 0 | 0 | 0 | 0 | 0 | 0 | 0 | 0 | 0 | 0 | 0 | 0 | 0 | 0 | 1 | 2 |
| 4 | 5.6 | 0 | 1 | 0 | 0 | 2 | 0 | 0 | 0 | 1 | 0 | 0 | 0 | 2 | 2 | 2 | 2 |
|  | 1.12 | 0 | 0 | 0 | 0 | 0 | 0 | 0 | 0 | 0 | 0 | 0 | 0 | 0 | 0 | 0 | 0 |
| 5 | 5.6 | 1 | 3 | 1 | 3 | 3 | 0 | 2 | 2 | 3 | 2 | 2 | 3 | 3 | 3 | 3 | 3 |
|  | 1.12 | 0 | 1 | 0 | 0 | 0 | 0 | 2 | 2 | 2 | 1 | 1 | 1 | 2 | 3 | 3 | 3 |
|  | 0.28 | 0 | 0 | 0 | 0 | 0 | N | 0 | 0 | 0 | 0 | 0 | 0 | 0 | 0 | 0 | 0 |
|  | 0.056 | 0 | 0 | 0 | 0 | 0 | N | 0 | 0 | 0 | 0 | 0 | 0 | 0 | 0 | 0 | 0 |
| 6 | 5.6 | 0 | 3 | 1 | 1 | 3 | N | 3 | 3 | 3 | 3 | 3 | 2 | 3 | 3 | 3 | 3 |
|  | 1.12 | 0 | 0 | 0 | 0 | 0 | N | 0 | 0 | 0 | 0 | 2 | 1 | 1 | 0 | 0 | 3 |
|  | 0.28 | 0 | 0 | 0 | 0 | 0 | N | 0 | 0 | 0 | 0 | 0 | 0 | 0 | 0 | 0 | 0 |

TABLE 3-continued

| | | PRE-EMERGENT ACTIVITY FOR WEEDS IN CROP PLANTS | | | | | | | | | | | | | | | |
|---|---|---|---|---|---|---|---|---|---|---|---|---|---|---|---|---|---|
| Example No. | Kg/ha | L | M | N | O | P | B | Q | D | R | E | F | C | J | S | K | T |
| | 0.056 | 0 | 0 | 0 | 0 | 0 | N | 0 | 0 | 0 | 0 | 0 | 0 | 0 | 0 | 0 | 0 |
| 7 | 5.6 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 8 | 5.6 | 0 | 0 | 1 | 1 | 3 | 0 | 0 | 0 | 0 | 0 | 0 | 0 | 3 | 3 | 3 | 3 |
| | 1.12 | 0 | 0 | 0 | 0 | 0 | 0 | 0 | 0 | 0 | 0 | 0 | 0 | 0 | 0 | 1 | 1 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 9 | 5.6 | 1 | 3 | 3 | 2 | 3 | 0 | 3 | 3 | 3 | 3 | 3 | 3 | 3 | 3 | 3 | 3 |
| | 1.12 | 0 | 0 | 0 | 0 | 0 | 0 | 0 | 0 | 0 | 0 | 0 | 0 | 0 | 1 | 3 | 3 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 10 | 5.6 | 1 | 3 | 3 | 3 | 3 | 0 | 2 | 1 | 2 | 3 | 1 | 1 | 3 | 3 | 3 | 3 |
| | 1.12 | 0 | 0 | 0 | 0 | 0 | 0 | 0 | 0 | 0 | 0 | 0 | 0 | 0 | 1 | 2 | 2 |
| | 0.28 | 0 | 0 | 0 | 0 | 0 | N | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 11 | 5.6 | 0 | 2 | 1 | 3 | 3 | 0 | 0 | 2 | 1 | 1 | 1 | 1 | 1 | 3 | 3 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 12 | 5.6 | 1 | 3 | 2 | 3 | 3 | 0 | 3 | 3 | 2 | 3 | 3 | 1 | 3 | 3 | 3 | 3 |
| | 1.12 | 0 | 2 | 1 | 0 | 3 | 0 | 2 | 2 | 1 | 2 | 2 | 1 | 3 | 3 | 2 | 3 |
| | 0.28 | 0 | 0 | 0 | 0 | 0 | 0 | 0 | 0 | 0 | 0 | 0 | 0 | 0 | 0 | 0 | 2 |
| | 0.056 | 0 | 0 | 0 | 0 | 0 | 0 | 0 | 0 | 0 | 0 | 0 | 0 | 0 | 0 | 0 | 0 |
| 13 | 5.6 | 0 | 1 | 3 | 3 | 3 | 1 | 3 | 3 | 3 | 3 | 3 | 2 | 3 | 3 | 3 | 3 |
| | 1.12 | 0 | 1 | 0 | 1 | 2 | 0 | 0 | 0 | 1 | 1 | 1 | 0 | 0 | 2 | 1 | 3 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 14 | 5.6 | 2 | 3 | 3 | 3 | 3 | 0 | 3 | 3 | 3 | 3 | 3 | 3 | 3 | 3 | 3 | 3 |
| | 1.12 | 0 | 1 | 0 | 0 | 1 | 0 | 0 | 0 | 0 | 2 | 2 | 0 | 0 | 3 | 3 | 3 |
| | 0.28 | 0 | 0 | 0 | 0 | 0 | 0 | 0 | 0 | 0 | 0 | 0 | 0 | 0 | 0 | 0 | 1 |
| | 0.056 | 0 | 0 | 0 | 0 | 0 | 0 | 0 | 0 | 0 | 0 | 0 | 0 | 0 | 0 | 0 | 0 |
| 15 | 5.6 | 3 | 3 | 2 | 3 | 3 | 0 | 3 | 3 | 3 | 3 | 3 | 2 | 3 | 3 | 3 | 3 |
| | 1.12 | 0 | 2 | 0 | 3 | 3 | 0 | 1 | 3 | 2 | 3 | 1 | 0 | 2 | 3 | 3 | 3 |
| | 0.28 | 0 | 1 | 0 | 0 | 2 | 0 | 0 | 1 | 2 | 1 | 0 | 0 | 0 | 0 | 1 | 2 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 16 | 5.6 | 0 | 2 | 0 | 0 | 3 | 0 | 2 | 2 | 2 | 3 | 3 | 2 | 3 | 3 | 3 | 3 |
| | 1.12 | 0 | 0 | 0 | 0 | 0 | 0 | 0 | 0 | 0 | 2 | 2 | 1 | 0 | 0 | 3 | 3 |
| | 0.28 | 0 | 0 | 0 | 0 | 0 | 0 | 0 | 0 | 0 | 0 | 0 | 0 | 1 | 0 | 0 | 1 |
| | 0.056 | 0 | 0 | 0 | 0 | 0 | 0 | 0 | 0 | 0 | 0 | 0 | 0 | 0 | 0 | 0 | 0 |
| 17 | 5.6 | 3 | 3 | 3 | 3 | 3 | 0 | 3 | 3 | 3 | 3 | 3 | 3 | N | 3 | 3 | 3 |
| | 1.12 | 0 | 2 | 3 | 1 | 3 | 0 | 2 | 1 | 2 | 2 | 2 | 1 | N | 3 | 3 | 3 |
| | 0.28 | 0 | 0 | 0 | 0 | 0 | 0 | 0 | 0 | 0 | 0 | 0 | 0 | N | 0 | 0 | 3 |
| | 0.056 | 0 | 0 | 0 | 0 | 0 | 0 | 0 | 0 | 0 | 0 | 0 | 0 | N | 0 | 0 | 1 |
| 19 | 5.6 | 0 | 2 | 1 | 1 | 2 | 0 | 0 | 0 | 0 | 1 | 2 | 0 | 2 | 2 | 3 | 3 |
| | 1.12 | 0 | 0 | 0 | 1 | 0 | 0 | 0 | 0 | 0 | 0 | 0 | 0 | 0 | 0 | 1 | 1 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 27 | 5.6 | 0 | 3 | 0 | 0 | 0 | 0 | 0 | 2 | 0 | 3 | 3 | 3 | 0 | 0 | 0 | 0 |
| | 1.12 | 0 | 0 | 0 | 0 | 0 | 0 | 0 | 3 | 0 | 2 | 2 | 2 | 0 | 0 | 0 | 0 |
| | 0.28 | 0 | 0 | 0 | 0 | 0 | 0 | 0 | 0 | 0 | 0 | 0 | 1 | 0 | 0 | 0 | 0 |
| 28 | 5.6 | 0 | 3 | 0 | 0 | 0 | 0 | 0 | 0 | 0 | 1 | 1 | 0 | 0 | 0 | 2 | 0 |
| | 1.12 | 0 | 0 | 0 | 1 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| | 0.056 | 0 | 1 | 0 | 0 | 0 | 0 | 0 | 0 | 0 | 0 | 0 | 0 | 0 | 0 | 0 | 0 |
| 29 | 5.6 | 0 | 1 | 0 | 0 | 1 | 0 | 0 | 0 | 0 | 2 | 1 | 0 | 1 | 2 | 3 | 2 |
| | 1.12 | 0 | 0 | 0 | 0 | 0 | 0 | 0 | 0 | 0 | 0 | 0 | 0 | 0 | 0 | 1 | 1 |
| | 0.28 | 0 | 0 | 0 | 0 | 0 | 0 | 0 | 0 | 0 | 0 | 0 | 0 | 0 | 0 | 0 | 0 |
| 31 | 5.6 | 0 | 0 | 1 | 1 | 0 | 0 | 0 | 0 | 0 | 1 | 2 | 0 | N | 0 | 3 | 2 |
| | 1.12 | 0 | 0 | 0 | 0 | 0 | 0 | 0 | 0 | 0 | 0 | 1 | 0 | N | 0 | 1 | 1 |
| | 0.28 | 0 | 0 | 0 | 0 | 0 | 0 | 0 | 0 | 0 | 0 | 1 | 0 | N | 0 | 1 | 0 |
| 32 | 5.6 | 1 | 3 | 2 | 1 | 3 | 0 | 3 | 3 | 2 | 3 | 3 | 1 | 3 | 3 | 3 | 3 |
| | 1.12 | 0 | 1 | 0 | 0 | 2 | 0 | 0 | 0 | 0 | 0 | 0 | 0 | 2 | 2 | 1 | 2 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 33 | 5.6 | 2 | 3 | 3 | 3 | 3 | 0 | 2 | 3 | 3 | 3 | 3 | 3 | 3 | 3 | 3 | 3 |
| | 1.12 | 0 | 1 | 1 | 0 | 2 | 0 | 0 | 0 | 1 | 1 | 2 | 0 | 2 | 2 | 3 | 3 |
| | 0.28 | 0 | 0 | 0 | 0 | 0 | 0 | 0 | 0 | 0 | 0 | 0 | 0 | 0 | 0 | 1 | 3 |
| | 0.056 | 0 | 0 | 0 | 0 | 0 | 0 | 0 | 0 | 0 | 0 | 0 | 0 | 0 | 0 | 0 | 2 |
| | 0.0112 | 0 | 0 | 0 | 0 | 0 | 0 | 0 | 0 | 0 | 0 | 0 | 0 | 0 | 0 | 0 | 2 |
| 34 | 5.6 | 1 | 3 | 3 | 2 | 3 | 0 | 3 | 3 | 3 | 3 | 3 | 3 | 3 | 3 | 3 | 3 |
| | 1.12 | 0 | 3 | 3 | 1 | 3 | 0 | 1 | 2 | 2 | 2 | 2 | 2 | 3 | 3 | 3 | 3 |
| | 0.28 | 0 | 1 | 1 | 0 | 0 | 0 | 0 | 0 | 0 | 0 | 0 | 0 | 2 | 0 | 1 | 3 |
| | 0.056 | 0 | 0 | 0 | 0 | 0 | 0 | 0 | 0 | 0 | 0 | 0 | 0 | 0 | 0 | 0 | 1 |
| | 0.0112 | 0 | 0 | 0 | 0 | 0 | 0 | 0 | 0 | 0 | 0 | 0 | 0 | 0 | 0 | 0 | 1 |
| 35 | 5.6 | 3 | 3 | 3 | 3 | 3 | 1 | 3 | 3 | 3 | 3 | 3 | 3 | 3 | 3 | 3 | 3 |
| | 1.12 | 1 | 3 | 3 | 2 | 3 | 0 | 2 | 0 | 3 | 3 | 3 | 3 | 3 | 3 | 3 | 3 |

TABLE 3-continued

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 0.28 | 0 | 2 | 0 | 1 | 1 | 0 | 1 | 0 | 1 | 1 | 1 | 0 | 2 | 1 | 3 | 3 |
| | 0.056 | 0 | 0 | 0 | 0 | 0 | 0 | 0 | 0 | 0 | 0 | 0 | 0 | 0 | 0 | 1 | 2 |
| | 0.0112 | 0 | 0 | 0 | 0 | 0 | 0 | 0 | 0 | 0 | 0 | 0 | 0 | 0 | 0 | 0 | 2 |
| 36 | 5.6 | 2 | 3 | 3 | 2 | 3 | 0 | 3 | 3 | 3 | 3 | 3 | 3 | 3 | 3 | 3 | 3 |
| | 1.12 | 0 | 1 | 0 | 0 | 3 | 0 | 0 | 0 | 1 | 2 | 1 | 1 | 0 | 3 | 3 | 3 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | N | 0 | 0 | 0 | 0 | 0 | 1 | 0 | 0 | 0 | 0 |
| 37 | 5.6 | 0 | 3 | 3 | 1 | 3 | 0 | 2 | 3 | 1 | 2 | 2 | 2 | 3 | 3 | 3 | 3 |
| | 1.12 | 0 | 0 | 0 | 0 | 2 | 0 | 0 | 0 | 0 | 1 | 0 | 0 | 0 | 2 | 3 | 1 |
| | 0.28 | 0 | 0 | 0 | 0 | 0 | 0 | 0 | 0 | 0 | 0 | 0 | 0 | 1 | 0 | 1 | 0 |
| 38 | 5.6 | 2 | 3 | 3 | 3 | 3 | 0 | 3 | 3 | 3 | 3 | 3 | 3 | 3 | 3 | 3 | 3 |
| | 1.12 | 1 | 3 | 3 | 1 | 3 | 0 | 3 | 2 | 1 | 3 | 3 | 0 | 3 | 3 | 3 | 3 |
| | 0.28 | 0 | 2 | 1 | 0 | 0 | 0 | 0 | 0 | 0 | 0 | 0 | 0 | 0 | 0 | 3 | 3 |
| | 0.056 | 0 | 0 | 0 | 0 | 0 | 0 | 0 | 0 | 0 | 0 | 0 | 0 | 0 | 0 | 0 | 2 |
| | 0.0112 | 0 | 0 | 0 | 0 | 0 | 0 | 0 | 0 | 0 | 0 | 0 | 0 | 0 | 0 | 0 | 3 |
| 39 | 5.6 | 3 | 3 | 3 | 3 | 3 | 1 | 3 | 3 | 3 | 3 | 3 | 3 | 3 | 3 | 3 | 3 |
| | 1.12 | 0 | 2 | 3 | 3 | 3 | 0 | 2 | 2 | 2 | 3 | 3 | 2 | 3 | 3 | 3 | 3 |
| | 0.28 | 0 | 1 | 0 | 1 | 2 | 0 | 0 | 1 | 0 | 2 | 0 | 1 | 1 | 2 | 3 | 3 |
| | 0.056 | 0 | 0 | 2 | 0 | 2 | 0 | 1 | 0 | 0 | 0 | 0 | 0 | 1 | 1 | 3 | 3 |
| | 0.0112 | 0 | 0 | 0 | 0 | 0 | 0 | 0 | 0 | 0 | 0 | 0 | 0 | 0 | 0 | 0 | 0 |
| 40 | 5.6 | 2 | 3 | 3 | 2 | 3 | 0 | 2 | 2 | 2 | 1 | 2 | 1 | 3 | 3 | 3 | 3 |
| | 1.12 | 0 | 0 | 1 | 0 | 3 | 0 | 0 | 0 | 0 | 1 | 0 | 0 | 2 | 2 | 3 | 3 |
| | 0.28 | 0 | 0 | 0 | 0 | 0 | 0 | 1 | 0 | 0 | 0 | 0 | 0 | 0 | 0 | 2 | 0 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 41 | 5.6 | 0 | 0 | 1 | 1 | 1 | 0 | 0 | 1 | 0 | 0 | 1 | 1 | 0 | 0 | 2 | 2 |
| | 1.12 | 0 | 1 | 0 | 1 | 0 | 0 | 0 | 0 | 0 | 0 | 0 | 0 | 0 | 0 | 0 | 1 |
| | 0.28 | 0 | 0 | 0 | 0 | 0 | 0 | 0 | 0 | 0 | 0 | 0 | 0 | 0 | 0 | 0 | 1 |
| 42 | 5.6 | 0 | 0 | 0 | 1 | 1 | 0 | 0 | 1 | 0 | 3 | 2 | 0 | 0 | 0 | 2 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 1 | 0 | 0 | 0 | 0 | 0 | 0 | 0 | 0 | 0 | 0 | 0 | 0 |
| 43 | 5.6 | 0 | 3 | 1 | 0 | 3 | 0 | 2 | 0 | 0 | 0 | 1 | 0 | 3 | 0 | 3 | 3 |
| | 1.12 | 0 | 0 | 0 | 0 | 0 | 0 | 2 | 0 | 0 | 0 | 0 | 0 | 1 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 44 | 5.6 | 0 | 1 | 0 | 0 | 0 | 0 | 0 | 0 | 1 | 1 | 1 | 0 | 1 | 0 | 2 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 45 | 5.6 | 0 | 2 | 1 | 1 | 1 | 0 | 0 | 1 | 2 | 3 | 2 | 2 | N | 3 | 3 | 3 |
| | 1.12 | 0 | 0 | 0 | 0 | 0 | 0 | 0 | 0 | 0 | 2 | 1 | 2 | N | 1 | 0 | 3 |
| | 0.28 | 0 | 0 | 0 | 0 | 0 | 0 | 0 | 0 | 0 | 1 | 0 | 1 | N | 0 | 0 | 2 |
| 46 | 5.6 | 0 | 3 | 0 | 0 | 0 | 0 | 0 | 0 | 0 | 3 | 0 | 0 | 0 | 0 | 0 | 2 |
| | 1.12 | 0 | 1 | 0 | 0 | 0 | 0 | 0 | 0 | 0 | 0 | 0 | 0 | 0 | 0 | 1 | 2 |
| | 0.28 | 0 | 0 | 0 | 0 | 0 | N | 0 | 0 | 0 | 0 | 0 | 0 | 0 | 0 | 0 | 0 |
| 47 | 5.6 | 0 | 3 | 0 | 0 | 0 | 0 | 0 | 0 | 0 | 2 | 1 | 1 | 0 | 0 | 0 | 1 |
| | 1.12 | 0 | 2 | 0 | 0 | 0 | 0 | 0 | 0 | 0 | 3 | 0 | 1 | 0 | 0 | 0 | 2 |
| | 0.28 | 0 | 0 | 0 | 0 | 0 | 0 | 0 | 0 | 0 | 0 | 0 | 0 | 0 | 0 | 2 | 0 |
| 48 | 5.6 | 0 | 2 | 2 | 0 | 2 | 0 | 3 | 1 | 1 | 3 | 2 | 0 | 3 | 3 | 3 | 3 |
| | 1.12 | 0 | 0 | 0 | 0 | 0 | 0 | 0 | 0 | 0 | 0 | 0 | 0 | 0 | 0 | 1 | 0 |
| | 0.28 | 0 | 0 | 0 | 0 | 0 | 0 | 0 | 0 | 0 | 0 | 0 | 0 | 0 | 0 | 0 | 0 |
| 49 | 5.6 | 1 | 3 | 3 | 2 | 3 | 0 | 1 | 1 | 2 | 2 | 2 | 1 | 3 | 3 | 3 | 3 |
| | 1.12 | 0 | 2 | 0 | 0 | 0 | 0 | 0 | 0 | 0 | 0 | 0 | 0 | 0 | 0 | 2 | 2 |
| | 0.28 | 0 | 0 | 0 | 0 | 0 | 0 | 0 | 0 | 0 | 0 | 0 | 0 | 0 | 0 | 0 | 1 |
| | 0.056 | 0 | 0 | 0 | 0 | 0 | 0 | 0 | 0 | 0 | 0 | 0 | 0 | 0 | 0 | 0 | 0 |
| 50 | 5.6 | 0 | 1 | 0 | 0 | 0 | 0 | 0 | 0 | 0 | 1 | 1 | 0 | 2 | 3 | 3 | 3 |
| | 1.12 | 0 | 1 | 0 | 0 | 0 | 0 | 0 | 0 | 0 | 0 | 1 | 0 | 0 | 1 | 0 | 0 |
| | 0.28 | 0 | 1 | 0 | 0 | 0 | 0 | 2 | 0 | 0 | 0 | 0 | 0 | 0 | 0 | 0 | 0 |
| 52 | 5.6 | 0 | 2 | 0 | 0 | 3 | 0 | 1 | 0 | 0 | 2 | 2 | 1 | 3 | 3 | 3 | 3 |
| | 1.12 | 0 | 2 | 1 | 0 | 0 | 0 | 0 | 0 | 0 | 1 | 0 | 0 | 0 | 0 | 2 | 1 |
| | 0.28 | 0 | 0 | 0 | 0 | 0 | 0 | 0 | 0 | 0 | 0 | 0 | 0 | 0 | 0 | 0 | 1 |
| 53 | 5.6 | 0 | 1 | 1 | 2 | 3 | 0 | 0 | 0 | 0 | 0 | 1 | 0 | 2 | 2 | 3 | 3 |
| | 1.12 | 0 | 0 | 0 | 1 | 0 | 0 | 0 | 0 | 0 | 0 | 0 | 0 | 0 | 1 | 0 | 0 |
| | 0.28 | 0 | 0 | 0 | 1 | 0 | 0 | 0 | 0 | 0 | 0 | 0 | 0 | 1 | 0 | 0 | 0 |
| 54 | 5.6 | 0 | 2 | 3 | 1 | 3 | 0 | 3 | 3 | 2 | 3 | 3 | 3 | 3 | 3 | 3 | 3 |
| | 1.12 | 0 | 1 | 0 | 0 | 0 | 0 | 1 | 0 | 0 | 2 | 2 | 1 | 1 | 1 | 2 | 3 |
| | 0.28 | 0 | 0 | 1 | 0 | 0 | 0 | 1 | 0 | 0 | 0 | 0 | 0 | 3 | 0 | 0 | 1 |
| | 0.056 | 0 | 0 | 1 | 1 | 2 | 0 | 1 | 0 | 0 | 0 | 0 | 0 | 2 | 1 | 0 | 3 |
| 55 | 5.6 | 0 | 2 | 0 | 0 | 2 | 0 | 0 | 0 | 0 | 1 | 2 | 2 | 0 | 1 | 3 | 2 |
| | 1.12 | 0 | 1 | 0 | 0 | 0 | 0 | 0 | 0 | 0 | 1 | 0 | 0 | 2 | 0 | 2 | 0 |
| | 0.28 | 0 | 0 | 0 | 0 | 0 | 0 | 0 | 0 | 0 | 0 | 0 | 0 | 0 | 0 | 0 | 0 |
| 56 | 5.6 | 0 | 2 | 0 | 0 | 1 | 0 | 1 | 1 | 0 | 1 | 1 | 0 | 1 | 1 | 3 | 3 |
| | 1.12 | 0 | 0 | 0 | 0 | 0 | 0 | 0 | 0 | 0 | 0 | 0 | 0 | 0 | 0 | 0 | 2 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 57 | 5.6 | 1 | 3 | 2 | 1 | 3 | 0 | 3 | 2 | 2 | 3 | 3 | 3 | 2 | 3 | 3 | 3 |
| | 1.12 | 0 | 0 | 0 | 0 | 0 | 0 | 0 | 0 | 2 | 1 | 0 | 1 | 0 | 0 | 0 | 3 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 58 | 5.6 | 0 | 2 | 1 | 1 | 1 | 0 | 0 | 0 | 0 | 0 | 1 | 0 | 0 | 1 | 3 | 2 |
| | 1.12 | 0 | 0 | 0 | 0 | 0 | 0 | 0 | 0 | 0 | 0 | 0 | 0 | 0 | 0 | 0 | 0 |

TABLE 3-continued
PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
|  | 0.28 | 0 | 0 | 0 | 0 | 0 | 0 | 0 | 0 | 0 | 0 | 0 | 0 | 0 | 0 | 0 | 0 |
| 59 | 5.6 | 0 | 2 | 0 | 0 | 3 | 0 | 2 | 1 | 0 | 3 | 2 | 1 | 2 | 3 | 3 | 3 |
|  | 1.12 | 0 | 0 | 0 | 0 | 0 | 0 | 1 | 0 | 0 | 0 | 0 | 0 | 1 | 0 | 0 | 3 |
|  | 0.28 | 0 | 0 | 0 | 0 | 0 | 0 | 0 | 0 | 0 | 0 | 0 | 0 | 0 | 0 | 0 | 0 |
| 60 | 5.6 | 0 | 3 | 1 | 1 | 1 | 2 | 2 | 1 | 1 | 3 | 3 | 1 | 3 | 3 | 3 | 3 |
|  | 1.12 | 0 | 0 | 1 | 0 | 0 | 0 | 2 | 0 | 0 | 0 | 0 | 0 | 0 | 0 | 1 | 0 |
|  | 0.28 | 0 | 0 | 0 | 0 | 0 | 0 | 1 | 0 | 0 | 0 | 0 | 0 | 0 | 0 | 1 | 0 |
| 61 | 5.6 | 0 | 0 | 0 | 0 | 0 | 0 | 0 | 0 | 0 | 2 | 0 | 1 | 2 | 0 | 0 | 0 |
|  | 1.12 | 0 | 0 | 0 | 0 | 0 | 0 | 0 | 0 | 0 | 0 | 0 | 0 | 1 | 0 | 0 | 0 |
| 63 | 5.6 | 0 | 0 | 0 | 0 | 2 | 2 | 0 | 1 | 0 | 1 | 2 | 0 | 0 | 2 | 3 | 0 |
|  | 1.12 | 0 | 1 | 0 | 0 | 1 | 0 | 0 | 0 | 0 | 0 | 0 | 0 | 0 | 0 | 1 | 0 |
|  | 0.28 | 0 | 0 | 0 | 0 | 0 | 0 | 0 | 0 | 0 | 0 | 0 | 0 | 0 | 0 | 0 | 0 |
| 64 | 5.6 | 0 | 1 | 1 | 0 | 0 | 0 | 0 | 0 | 0 | 0 | 1 | 0 | 0 | 0 | 3 | 0 |
|  | 1.12 | 0 | 1 | 0 | 0 | 0 | 0 | 0 | 0 | 0 | 0 | 1 | 0 | 0 | 0 | 0 | 0 |
|  | 0.28 | 0 | 0 | 0 | 0 | 0 | 0 | 1 | 0 | 0 | 0 | 0 | 0 | 0 | 0 | 0 | 0 |
| 65 | 5.6 | 0 | 1 | 0 | 0 | 0 | 0 | 1 | 0 | 0 | 2 | 1 | 0 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 68 | 5.6 | 1 | 3 | 2 | 1 | 3 | 1 | 3 | 2 | 2 | 3 | 3 | 2 | 3 | 3 | 3 | 3 |
|  | 1.12 | 0 | 0 | 0 | 0 | 0 | 0 | 2 | 0 | 1 | 2 | 2 | 1 | 1 | 0 | 1 | 1 |
|  | 0.28 | 0 | 0 | 0 | 0 | 0 | 0 | 0 | 0 | 0 | 0 | 0 | 0 | 1 | 0 | 0 | 0 |
|  | 0.056 | 0 | 0 | 0 | 0 | 0 | 0 | 0 | 0 | 0 | 0 | 0 | 0 | 1 | 0 | 0 | 0 |
| 69 | 5.6 | 0 | 1 | 0 | 0 | 1 | 0 | 1 | 2 | 1 | 2 | 0 | 0 | 1 | 3 | 3 | 3 |
|  | 1.12 | 0 | 1 | 0 | 0 | 0 | 0 | 0 | 0 | 0 | 0 | 0 | 0 | 2 | 0 | 0 | 1 |
|  | 0.28 | 0 | 0 | 0 | 0 | 0 | 0 | 0 | 0 | 0 | 0 | 0 | 0 | 0 | 0 | 0 | 0 |
| 71 | 5.6 | 0 | 3 | 0 | 3 | 2 | N | 2 | 2 | 3 | 3 | 3 | 2 | 2 | 3 | 3 | 3 |
|  | 1.12 | 0 | 1 | 0 | 0 | 0 | 0 | 0 | 0 | 0 | 0 | 0 | 0 | 0 | 1 | 2 | 2 |
|  | 0.28 | 0 | 0 | 0 | 0 | 0 | 0 | 0 | 0 | 0 | 0 | 0 | 0 | 0 | 0 | 0 | 0 |
| 72 | 5.6 | 3 | 3 | 3 | 1 | 3 | 0 | 3 | 3 | 3 | 3 | 3 | 3 | 3 | 3 | 3 | 3 |
|  | 1.12 | 0 | 1 | 1 | 0 | 2 | 0 | 0 | 0 | 0 | 1 | 2 | 1 | 1 | 1 | 2 | 3 |
|  | 0.28 | 0 | 0 | 0 | 0 | 0 | 0 | 0 | 0 | 0 | 0 | 0 | 0 | 0 | 0 | 0 | 0 |
| 73 | 5.6 | 0 | 0 | 1 | 0 | 0 | 0 | 0 | 0 | 0 | 1 | 1 | 0 | 0 | 0 | 1 | 2 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 74 | 5.6 | 0 | 3 | 3 | 3 | 3 | 0 | 3 | 2 | 2 | 3 | 3 | 1 | 3 | 3 | 3 | 3 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 75 | 5.6 | 2 | 3 | 2 | 3 | 3 | 0 | 3 | 3 | 3 | 3 | 3 | 2 | 3 | 3 | 3 | 3 |
|  | 1.12 | 0 | 0 | 0 | 1 | 0 | 0 | 0 | 0 | 0 | 0 | 0 | 0 | 1 | 2 | 3 | 3 |
|  | 0.28 | 0 | 0 | 0 | 0 | 0 | 0 | 0 | 0 | 0 | 0 | 0 | 0 | 0 | 0 | 0 | 0 |
| 76 | 5.6 | 0 | 3 | 2 | 2 | 0 | 0 | 1 | 2 | 2 | 2 | 2 | 0 | 1 | 3 | 3 | 3 |
|  | 1.12 | 0 | 0 | 0 | 0 | 0 | 0 | 0 | 0 | 0 | 0 | 0 | 0 | 0 | 0 | 1 | 1 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 1 | 0 | 0 | 0 | 0 | 0 | 0 |
| 77 | 5.6 | 2 | 3 | 1 | 2 | 3 | 0 | 0 | 3 | 2 | 3 | 3 | 0 | 3 | 3 | 3 | 3 |
|  | 1.12 | 0 | 1 | 0 | 1 | 0 | 0 | 3 | 0 | 1 | 1 | 1 | 0 | 1 | 1 | 3 | 3 |
|  | 0.28 | 0 | 0 | 0 | 0 | 0 | 0 | 0 | 0 | 0 | 0 | 0 | 0 | 0 | 0 | 0 | 0 |
| 78 | 5.6 | 1 | 3 | 1 | 3 | 3 | 1 | 3 | 3 | 3 | 3 | 3 | 3 | 3 | 3 | 3 | 3 |
|  | 1.12 | 0 | 2 | 0 | 1 | 0 | 0 | 0 | 0 | 1 | 3 | 3 | 0 | 1 | 1 | 3 | 3 |
|  | 0.28 | 0 | 0 | 0 | 0 | 0 | 0 | 0 | 0 | 0 | 0 | 0 | 0 | 0 | 0 | 1 | 3 |
|  | 0.056 | 0 | 0 | 0 | 0 | 0 | 0 | 0 | 0 | 0 | 0 | 0 | 0 | 0 | 0 | 0 | 0 |
| 79 | 5.6 | 0 | 2 | 1 | 1 | 1 | 3 | 0 | 2 | 2 | 1 | 1 | 0 | 1 | 2 | 3 | 3 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 80 | 5.6 | 0 | 3 | 1 | 2 | 3 | 0 | 3 | 3 | 2 | 3 | 2 | 1 | 3 | 3 | 3 | 3 |
|  | 1.12 | 0 | 0 | 0 | 0 | 0 | 0 | 0 | 0 | 0 | 0 | 0 | 0 | 0 | 0 | 2 | 0 |
|  | 0.28 | 0 | 0 | 0 | 0 | 0 | 0 | 0 | 0 | 0 | 0 | 0 | 0 | 0 | 0 | 0 | 2 |
| 81 | 5.6 | 1 | 3 | 3 | 0 | 3 | 0 | 3 | 1 | 2 | 3 | 3 | 2 | 3 | 3 | 3 | 3 |
|  | 1.12 | 0 | 1 | 0 | 0 | 2 | 0 | 1 | 0 | 0 | 1 | 1 | 1 | 0 | 2 | 2 | 3 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 82 | 5.6 | 0 | 2 | 0 | 1 | 3 | 0 | 1 | 0 | 0 | 0 | 0 | 0 | 3 | 3 | 3 | 3 |
|  | 1.12 | 0 | 0 | 0 | 0 | 0 | 0 | 0 | 0 | 0 | 0 | 0 | 0 | 0 | 0 | 0 | 3 |
|  | 0.28 | 0 | 0 | 0 | 0 | 0 | 0 | 0 | 0 | 0 | 0 | 0 | 0 | 0 | 0 | 0 | 2 |
|  | 0.056 | 0 | 0 | 0 | 0 | 0 | 0 | 0 | 0 | 0 | 0 | 0 | 0 | 0 | 0 | 0 | 0 |
| 83 | 5.6 | 1 | 2 | 2 | 2 | 2 | 0 | 0 | 0 | 1 | 3 | 3 | 0 | 2 | 3 | 3 | 3 |
|  | 1.12 | 0 | 0 | 1 | 1 | 0 | 0 | 0 | 0 | 0 | 0 | 0 | 0 | 1 | 1 | 1 | 1 |
|  | 0.28 | 0 | 0 | 0 | 0 | 0 | 0 | 0 | 0 | 0 | 0 | 0 | 0 | 0 | 0 | 0 | 2 |
| 84 | 5.6 | 0 | 3 | 1 | 2 | 3 | 0 | 3 | 3 | 2 | 3 | 3 | 1 | 3 | 3 | 3 | 3 |
|  | 1.12 | 0 | 1 | 0 | 1 | 3 | 0 | 1 | 0 | 0 | 0 | 0 | 0 | 1 | 1 | 1 | 3 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 85 | 5.6 | 0 | 2 | 3 | 1 | 2 | 0 | 1 | 1 | 0 | 2 | 2 | 2 | 2 | 3 | 3 | 3 |
|  | 1.12 | 0 | 0 | 0 | 0 | 0 | 1 | 0 | 1 | 0 | 0 | 2 | 1 | 0 | 1 | 0 | 0 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 1 | 0 | 0 | 2 |
|  | 0.0112 | 0 | 0 | 0 | 0 | 0 | 0 | 0 | 0 | 0 | 0 | 0 | 0 | 0 | 0 | 1 | 0 |
| 86 | 5.6 | 0 | 3 | 1 | 2 | 3 | 0 | 3 | 2 | 2 | 3 | 3 | 1 | 3 | 3 | 3 | 3 |
|  | 1.12 | 0 | 1 | 0 | 1 | 3 | 0 | 1 | 1 | 0 | 1 | 0 | 0 | 3 | 0 | 3 | 3 |

TABLE 3-continued

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
|  | 0.28 | 0 | 1 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 87 | 5.6 | 0 | 1 | 1 | 0 | 1 | 0 | 3 | 0 | 0 | 0 | 0 | 0 | 1 | 1 | 3 | 3 |
|  | 1.12 | 0 | 0 | 1 | 0 | 0 | 0 | 2 | 0 | 0 | 0 | 0 | 0 | 0 | 0 | 0 | 0 |
|  | 0.28 | 0 | 1 | 0 | 0 | 0 | 0 | 0 | 0 | 0 | 0 | 0 | 0 | 0 | 0 | 0 | 0 |
| 88 | 5.6 | 0 | 0 | 1 | 1 | 2 | 0 | 0 | 1 | 1 | 0 | 2 | 1 | 3 | 1 | 2 | 1 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 89 | 5.6 | 0 | 2 | 1 | 1 | 1 | 0 | 2 | 0 | 1 | 3 | 2 | 1 | 1 | 1 | 3 | 3 |
|  | 1.12 | 0 | 0 | 1 | 1 | 0 | 0 | 0 | 0 | 0 | 0 | 1 | 0 | 0 | 0 | 0 | 3 |
|  | 0.28 | 0 | 0 | 0 | 1 | 0 | 0 | 1 | 0 | 0 | 0 | 0 | 0 | 1 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 90 | 5.6 | 0 | 3 | 1 | 2 | 2 | 0 | 1 | 2 | 2 | 3 | 3 | 1 | 1 | 3 | 3 | 3 |
|  | 1.12 | 0 | 0 | 0 | 1 | 1 | 0 | 0 | 2 | 0 | 2 | 1 | 0 | 0 | 1 | 3 | 3 |
|  | 0.28 | 0 | 0 | 0 | 1 | 0 | 0 | 0 | 0 | 0 | 0 | 0 | 0 | 0 | 0 | 1 | 0 |
|  | 0.056 | 0 | 0 | 0 | 0 | 0 | 0 | 0 | 0 | 0 | 0 | 0 | 0 | 0 | 0 | 0 | 0 |
| 91 | 5.6 | 0 | 1 | 0 | 0 | 1 | 0 | 0 | 0 | 0 | 0 | 2 | 0 | 0 | 2 | 3 | 0 |
|  | 1.12 | 0 | 0 | 0 | 0 | 0 | 0 | 1 | 0 | 0 | 0 | 0 | 0 | 0 | 0 | 0 | 0 |
|  | 0.28 | 0 | 0 | 0 | 0 | 0 | 0 | 0 | 1 | 0 | 0 | 0 | 0 | 0 | 0 | 0 | 0 |
| 92 | 5.6 | 0 | 3 | 0 | 1 | 1 | 0 | 1 | 1 | 1 | 2 | 1 | 0 | 1 | 1 | 3 | 3 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 93 | 5.6 | 1 | 2 | 2 | 3 | 1 | 0 | 1 | 1 | 2 | 3 | 3 | 0 | 2 | 3 | 3 | 3 |
|  | 1.12 | 0 | 1 | 0 | 0 | 1 | 0 | 0 | 0 | 0 | 0 | 1 | 0 | 0 | 1 | 2 | 3 |
|  | 0.28 | 0 | 1 | 0 | 0 | 0 | 0 | 0 | 0 | 0 | 0 | 1 | 0 | 0 | 0 | 0 | 1 |
| 94 | 5.6 | 0 | 1 | 0 | 0 | 1 | 0 | 0 | 1 | 1 | 1 | 0 | 0 | 0 | 1 | 1 | 1 |
|  | 1.12 | 0 | 0 | 0 | 0 | 0 | 0 | 0 | 0 | 0 | 0 | 0 | 1 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 95 | 5.6 | 0 | 1 | 2 | 2 | 3 | N | 1 | 2 | 2 | 3 | 2 | 1 | 3 | 3 | 3 | 3 |
|  | 1.12 | 0 | 0 | 0 | 1 | 3 | N | 0 | 0 | 0 | 0 | 0 | 0 | 2 | 3 | 2 | 3 |
|  | 0.28 | 0 | 0 | 0 | 0 | 0 | N | 1 | N | 0 | 0 | 0 | 0 | 0 | 0 | 0 | 0 |
|  | 0.056 | 0 | 0 | 0 | 0 | 0 | N | 0 | 0 | 0 | 0 | 0 | 0 | 0 | 0 | 0 | 0 |
| 96 | 5.6 | 0 | 2 | 1 | 3 | 3 | 1 | 2 | 3 | 2 | 1 | 2 | 1 | 3 | 3 | 3 | 3 |
|  | 1.12 | 0 | 0 | 0 | 1 | 0 | 0 | 0 | 0 | 0 | 0 | 0 | 0 | 0 | 0 | 0 | 2 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | N | 0 | N | 0 | 0 | 0 | 0 | 0 | 0 | 0 | 1 |
| 97 | 5.6 | 1 | 2 | 2 | 3 | 3 | 1 | 1 | 2 | 2 | 1 | 3 | 0 | 3 | 3 | 3 | 3 |
|  | 1.12 | 0 | 0 | 0 | 1 | 1 | N | 1 | 0 | 0 | 0 | 0 | 0 | 1 | 2 | 1 | 1 |
|  | 0.28 | 0 | 0 | 0 | 0 | 1 | N | 1 | 0 | 0 | 0 | 0 | 0 | 0 | 0 | 0 | 0 |
|  | 0.056 | 0 | 0 | 0 | 0 | 0 | N | 0 | 0 | 0 | 0 | 0 | 0 | 0 | 0 | 0 | 0 |
| 98 | 5.6 | 3 | 3 | 3 | 3 | 3 | 3 | 3 | 3 | 3 | 3 | 3 | 3 | 3 | 3 | 3 | 3 |
|  | 1.12 | 0 | 2 | 3 | 3 | 3 | 0 | 1 | 3 | 3 | 2 | 3 | 1 | 3 | 3 | 3 | 3 |
|  | 0.28 | 0 | 1 | 1 | 0 | 2 | 0 | 1 | 2 | 1 | 2 | 2 | 1 | 0 | 1 | 3 | 2 |
|  | 0.056 | 0 | 0 | 0 | 0 | 1 | N | 1 | 0 | 0 | 0 | 0 | 0 | 1 | 0 | 0 | 0 |
|  | 0.0112 | 0 | 0 | 0 | 0 | 0 | 0 | 0 | 0 | 0 | 0 | 0 | 0 | 0 | 0 | 0 | 1 |
| 99 | 5.6 | 1 | 2 | 2 | 3 | 3 | 0 | 3 | 0 | 2 | 3 | 3 | 1 | 3 | 3 | 3 | 3 |
|  | 1.12 | 0 | 1 | 2 | 1 | 0 | N | 1 | 0 | 0 | 1 | 0 | 0 | 2 | 3 | 3 | 3 |
|  | 0.28 | 0 | 0 | 0 | 0 | 1 | N | 0 | 0 | 0 | 1 | 0 | 0 | 0 | 1 | 0 | 1 |
|  | 0.056 | 0 | 0 | 0 | 0 | 0 | N | 0 | 0 | 0 | 0 | 0 | 0 | 0 | 0 | 0 | 1 |
| 100 | 5.6 | 2 | 3 | 3 | 3 | 3 | 1 | 2 | 3 | 3 | 3 | 3 | 3 | 3 | 3 | 3 | 3 |
|  | 1.12 | 0 | 1 | 2 | 3 | 2 | 0 | 1 | 1 | 3 | 3 | 3 | 3 | 3 | 3 | 3 | 3 |
|  | 0.28 | 0 | 0 | 1 | 2 | 2 | N | 0 | 0 | 2 | 3 | 1 | 1 | 2 | 2 | 3 | 3 |
|  | 0.056 | 0 | 0 | 0 | 0 | 0 | 0 | 0 | 0 | 0 | 0 | 0 | 0 | 0 | 0 | 0 | 1 |
|  | 0.0112 | 0 | 0 | 0 | 0 | 0 | N | 0 | 0 | 0 | 0 | 0 | 0 | 0 | 0 | 0 | 0 |
| 101 | 5.6 | 2 | 3 | 2 | 3 | 3 | 0 | 3 | 3 | 3 | 3 | 3 | 1 | 3 | 3 | 3 | 3 |
|  | 1.12 | 1 | 1 | 1 | 3 | 2 | 0 | 1 | 2 | 2 | 2 | 3 | 1 | 2 | 3 | 3 | 3 |
|  | 0.280 | 0 | 0 | 0 | 1 | 1 | 0 | 0 | 0 | 1 | 0 | 1 | 0 | 0 | 3 | 3 | 3 |
|  | 0.056 | 0 | 0 | 0 | 1 | 1 | N | 0 | 0 | 0 | 0 | 0 | 0 | 1 | 1 | 1 | 1 |
| 102 | 5.6 | 0 | 3 | 3 | 3 | 3 | 0 | 2 | 3 | 2 | 3 | 3 | 1 | 3 | 3 | 3 | 3 |
|  | 1.12 | 0 | 1 | 1 | 3 | 2 | 0 | 0 | 0 | 1 | 2 | 2 | 0 | 3 | 3 | 3 | 3 |
|  | 0.28 | 0 | 0 | 0 | 0 | 0 | N | 0 | 0 | 0 | 0 | 0 | 0 | 0 | 0 | 3 | 1 |
|  | 0.056 | 0 | 0 | 0 | 0 | 0 | 0 | 2 | 0 | 0 | 1 | 0 | 0 | 0 | 0 | 0 | 0 |
| 103 | 5.6 | 0 | 2 | 0 | 1 | 3 | 0 | 3 | 2 | 2 | 3 | 3 | 2 | 3 | 3 | 3 | 3 |
|  | 1.12 | 0 | 1 | 0 | 2 | 0 | 0 | 0 | 0 | 1 | 1 | 1 | 0 | 0 | 2 | 3 | 3 |
|  | 0.28 | 0 | 1 | 0 | 0 | 0 | N | 0 | 0 | 1 | 1 | 0 | 0 | 1 | 1 | 1 | 1 |
| 104 | 5.6 | 0 | 2 | 1 | 1 | 2 | 0 | 1 | 2 | 1 | 2 | 3 | 1 | 3 | 3 | 3 | 3 |
|  | 1.12 | 0 | 1 | 0 | 0 | 0 | 0 | N | 0 | 0 | 0 | 1 | 0 | 1 | 1 | 1 | 3 |
|  | 0.28 | 0 | 0 | 0 | 0 | 0 | 0 | 1 | 0 | 0 | 0 | 0 | 1 | 0 | 0 | 0 | 0 |
| 105 | 5.6 | 0 | 1 | 3 | 1 | 2 | 0 | 3 | 0 | 1 | 2 | 1 | 0 | 3 | 3 | 3 | 3 |
|  | 1.12 | 0 | 1 | 0 | 0 | 0 | 0 | 1 | 0 | 0 | 0 | 0 | 0 | 0 | 0 | 0 | 1 |
|  | 0.28 | 0 | 0 | 0 | 0 | 0 | 0 | 0 | N | 1 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 1 | 1 |
| 106 | 5.6 | 3 | 3 | 3 | 3 | 3 | 3 | 3 | 3 | 3 | 3 | 3 | 3 | 3 | 3 | 3 | 3 |
|  | 1.12 | 2 | 2 | 2 | 3 | 3 | 2 | 2 | 3 | 3 | 3 | 2 | 3 | 3 | 3 | 3 | 3 |
|  | 0.28 | 0 | 2 | 0 | 3 | 2 | 0 | 0 | 0 | 2 | 3 | 1 | 1 | 0 | 3 | 3 | 3 |
|  | 0.056 | 0 | 0 | 0 | 0 | 0 | 0 | 0 | 0 | 1 | 2 | 1 | 0 | 0 | 2 | 2 | 0 |
| 109 | 5.6 | 0 | 3 | 0 | 0 | 1 | 0 | 3 | 3 | 1 | 3 | 1 | 1 | 2 | 1 | 1 | 2 |
|  | 1.12 | 0 | 2 | 0 | 0 | 0 | 0 | 0 | 0 | 1 | 3 | 0 | 0 | 0 | 0 | 1 | 0 |
|  | 0.28 | 0 | 0 | 0 | 0 | 0 | 0 | 0 | 0 | 0 | 1 | 0 | 0 | 0 | 0 | 1 | 0 |
| 110 | 5.6 | 0 | 2 | 2 | 2 | 2 | 0 | 3 | 1 | 2 | 3 | 0 | 0 | 3 | 3 | 3 | 3 |

TABLE 3-continued

| Example No. | Kg/ha | L | M | N | O | P | B | Q | D | R | E | F | C | J | S | K | T |
|---|---|---|---|---|---|---|---|---|---|---|---|---|---|---|---|---|---|
| | 1.12 | 0 | 0 | 0 | 0 | 0 | 0 | 0 | 0 | 0 | 1 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 111 | 5.6 | 0 | 0 | 1 | 1 | 2 | 0 | 1 | 1 | 0 | 1 | 0 | 1 | 3 | 2 | 3 | 3 |
| | 1.12 | 0 | 0 | 0 | 0 | 0 | 0 | N | 0 | 0 | 0 | 0 | 0 | 0 | 0 | 0 | 1 |
| 112 | 5.6 | 0 | 3 | 2 | 3 | 2 | 1 | 1 | 2 | 2 | 3 | 2 | 1 | 3 | 3 | 3 | 3 |
| | 1.12 | 0 | 1 | 0 | 2 | 2 | N | 0 | 1 | 2 | 2 | 0 | 0 | 1 | 2 | 3 | 3 |
| | 0.28 | 0 | 0 | 0 | 2 | 2 | N | 0 | 1 | 2 | 1 | 0 | 0 | 0 | 1 | 3 | 3 |
| | 0.056 | 0 | 0 | 0 | 2 | 2 | N | 0 | 1 | 2 | 1 | 0 | 0 | 0 | 1 | 2 | 3 |
| | 0.0112 | 0 | 0 | 0 | 0 | 2 | 0 | 0 | 1 | 0 | 2 | 1 | 0 | 1 | 0 | 1 | 0 |
| 113 | 5.6 | 0 | 3 | 2 | 3 | 2 | 0 | 3 | 3 | 3 | 3 | 2 | 2 | 2 | 3 | 3 | 3 |
| | 1.12 | 0 | 1 | 0 | 2 | 1 | N | 2 | 2 | 2 | 3 | 0 | 0 | 0 | 3 | 3 | 3 |
| | 0.28 | 0 | 0 | 0 | 1 | 2 | 0 | 0 | 1 | 2 | 1 | 0 | 0 | 0 | 1 | 2 | 3 |
| | 0.056 | 0 | 0 | 0 | 0 | 0 | 0 | 1 | 0 | 0 | 0 | 0 | 1 | 0 | 0 | 0 | 0 |
| 114 | 5.6 | 3 | 3 | 3 | 3 | 3 | 2 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 3 | 2 | 3 | 3 | 3 | 3 |
| | 0.28 | 1 | 3 | 3 | 3 | 3 | 0 | 2 | 3 | 2 | 3 | 3 | 1 | 3 | 3 | 3 | 3 |
| | 0.056 | 0 | 1 | 0 | 2 | 3 | 0 | 0 | 1 | 1 | 1 | 1 | 0 | 3 | 3 | 3 | 3 |
| | 0.0112 | 0 | 0 | 0 | 0 | 2 | 0 | 0 | 0 | 0 | 0 | 1 | 0 | 2 | 1 | 3 | 3 |
| | 0.0056 | 0 | 0 | 0 | 0 | 0 | 0 | 2 | 0 | 0 | 0 | 0 | 0 | 2 | 0 | 0 | 2 |
| | 0.00112 | 0 | 0 | 0 | 0 | 0 | 0 | 0 | 0 | 0 | 0 | 0 | 0 | 0 | 0 | 0 | 0 |
| 115 | 5.6 | 0 | 2 | 1 | 2 | 3 | 0 | 3 | 2 | 2 | 3 | 2 | 1 | 3 | 3 | 3 | 3 |
| | 1.12 | 0 | 1 | 1 | 0 | 0 | 0 | 1 | 2 | 2 | 2 | 1 | 1 | 1 | 2 | 3 | 3 |
| | 0.28 | 0 | 0 | 0 | 0 | 0 | 0 | 1 | 1 | 0 | 0 | 1 | 0 | 0 | 0 | 1 | 0 |
| 116 | 5.6 | 2 | 3 | 3 | 3 | 3 | 0 | 2 | 3 | 2 | 3 | 3 | 3 | 3 | 3 | 3 | 3 |
| | 1.12 | 0 | 1 | 1 | 2 | 3 | 0 | 2 | 2 | 2 | 2 | 1 | 1 | 3 | 3 | 3 | 3 |
| | 0.28 | 1 | 0 | 0 | 0 | 1 | 0 | 0 | 0 | 1 | 0 | 0 | 0 | 1 | 2 | 3 | 2 |
| | 0.056 | 0 | 0 | 0 | 0 | 0 | 0 | 0 | 1 | 0 | 0 | 0 | 0 | 0 | 0 | 0 | 1 |
| 117 | 5.6 | 3 | 3 | 3 | 3 | 3 | 1 | 3 | 3 | 3 | 3 | 3 | 2 | 3 | 3 | 3 | 3 |
| | 1.12 | 1 | 1 | 2 | 2 | 3 | 0 | 1 | 2 | 2 | 2 | 2 | 1 | 3 | 3 | 3 | 3 |
| | 0.28 | 0 | 0 | 0 | 0 | 1 | 0 | 0 | 1 | 1 | 0 | 0 | 0 | 1 | 2 | 3 | 3 |
| | 0.056 | 0 | 0 | 0 | 0 | 0 | 0 | 1 | 0 | 0 | 0 | 1 | 0 | 0 | 0 | 1 | 0 |
| | 0.0112 | 0 | 0 | 0 | 0 | 0 | 0 | 0 | 0 | 0 | 0 | 0 | 0 | 0 | 0 | 0 | 0 |
| 118 | 5.6 | 3 | 3 | 3 | 3 | 3 | 3 | 3 | 3 | 3 | 3 | 3 | 3 | 3 | 3 | 3 | 3 |
| | 1.12 | 3 | 3 | 3 | 3 | 3 | 1 | 3 | 3 | 3 | 3 | 3 | 3 | 3 | 3 | 3 | 3 |
| | 0.28 | 2 | 3 | 2 | 3 | 3 | 0 | 3 | 2 | 2 | 3 | 3 | 1 | 3 | 3 | 3 | 3 |
| | 0.056 | 0 | 0 | 0 | 2 | 1 | 0 | 1 | 0 | 1 | 0 | 0 | 0 | 1 | 3 | 3 | 3 |
| | 0.0112 | 0 | 0 | 0 | 0 | 0 | 0 | 0 | 0 | 0 | 0 | 0 | 0 | 0 | 1 | 0 | 1 |
| 119 | 5.6 | 0 | 3 | 3 | 3 | 3 | 3 | 1 | 3 | 2 | 3 | 2 | 1 | 3 | 3 | 3 | 3 |
| | 1.12 | 0 | 2 | 0 | 2 | 2 | 0 | 2 | 0 | 0 | 1 | 0 | 1 | 2 | 2 | 3 | 2 |
| | 0.28 | 0 | 0 | 0 | 0 | 0 | N | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 120 | 5.6 | 0 | 2 | 3 | 3 | 3 | 1 | 0 | 1 | 2 | 2 | 1 | 1 | 3 | 3 | 3 | 3 |
| | 1.12 | 0 | 1 | 0 | 1 | 0 | 0 | 0 | 1 | 0 | 1 | 0 | 0 | 0 | 0 | 3 | 1 |
| | 0.28 | 0 | 0 | 0 | 0 | 0 | N | 0 | 0 | 0 | 0 | 0 | 0 | 0 | 0 | 1 | 0 |
| 121 | 5.6 | 3 | 3 | 3 | 3 | 3 | 1 | 3 | 3 | 3 | 3 | 3 | 3 | 3 | 3 | 3 | 3 |
| | 1.12 | 0 | 3 | 1 | 3 | 3 | 0 | 0 | 2 | 2 | 3 | 1 | 1 | 3 | 3 | 3 | 3 |
| | 0.28 | 0 | 1 | 0 | 1 | 1 | 0 | 0 | 0 | 0 | 2 | 0 | 0 | 1 | 1 | 3 | 3 |
| | 0.056 | 0 | 0 | 0 | 0 | 0 | 0 | 0 | 0 | 0 | 1 | 0 | 0 | 2 | 1 | 1 | 1 |
| 122 | 5.6 | 0 | 3 | 3 | 3 | 3 | 0 | 1 | 3 | 2 | 3 | 3 | 1 | 3 | 3 | 3 | 3 |
| | 1.12 | 0 | 0 | 0 | 1 | 2 | 0 | 1 | 0 | 0 | 0 | 1 | 0 | 3 | 3 | 3 | 2 |
| | 0.28 | 0 | 0 | 0 | 0 | 0 | 0 | 0 | 0 | 0 | 0 | 0 | 0 | 0 | 0 | 0 | 0 |
| 123 | 5.6 | 0 | 1 | 0 | 1 | 3 | 0 | 1 | 1 | 1 | 2 | 1 | 3 | 1 | 2 | 3 | 3 |
| | 1.12 | 0 | 0 | 0 | 0 | 0 | 0 | 1 | 0 | 0 | 0 | 0 | 0 | 1 | 0 | 2 | 1 |
| | 0.28 | 0 | 0 | 0 | 0 | 0 | 0 | 0 | 0 | 0 | 0 | 0 | 0 | 0 | 0 | 0 | 1 |
| 124 | 5.6 | 3 | 3 | 3 | 3 | 3 | 0 | 3 | 3 | 3 | 3 | 3 | 2 | 3 | 3 | 3 | 3 |
| | 1.12 | 2 | 3 | 3 | 3 | 3 | 0 | 2 | 2 | 2 | 3 | 2 | 1 | 3 | 3 | 3 | 3 |
| | 0.28 | 0 | 0 | 3 | 2 | 3 | 0 | 0 | 2 | 1 | 3 | 1 | 0 | 3 | 3 | 3 | 3 |
| | 0.056 | 0 | 0 | 0 | 0 | 2 | 0 | 0 | 0 | 0 | 2 | 0 | 0 | 3 | 2 | 3 | 2 |
| | 0.0112 | 0 | 0 | 0 | 0 | 0 | 0 | 0 | 0 | 0 | 0 | 0 | 0 | 0 | 0 | 0 | 0 |
| 125 | 5.6 | 3 | 3 | 3 | 3 | 3 | 0 | 3 | 3 | 3 | 3 | 3 | 3 | 3 | 3 | 3 | 3 |
| | 1.12 | 2 | 3 | 3 | 3 | 3 | 0 | 3 | 1 | 2 | 3 | 2 | 2 | 3 | 3 | 3 | 3 |
| | 0.28 | 0 | 1 | 2 | 2 | 3 | 0 | 2 | 0 | 1 | 1 | 0 | 1 | 3 | 3 | 3 | 3 |
| | 0.056 | 0 | 0 | 0 | 1 | 1 | 0 | 0 | 0 | 0 | 0 | N | 0 | 0 | 0 | 2 | 2 |
| | 0.0112 | 0 | 0 | 0 | 1 | 1 | 0 | 0 | 0 | 0 | 0 | 0 | 0 | 0 | 0 | 0 | 1 |
| 126 | 5.6 | 1 | 3 | 3 | 3 | 3 | 0 | 3 | 3 | 2 | 3 | 1 | 2 | 3 | 3 | 3 | 3 |
| | 1.12 | 0 | 0 | 0 | 0 | 2 | 0 | 0 | 0 | 1 | 3 | 0 | 0 | 2 | 2 | 3 | 3 |
| | 0.28 | 0 | 0 | 0 | 0 | 1 | 0 | 0 | 0 | 2 | 0 | 0 | 0 | 0 | 0 | 0 | 2 |
| | 0.056 | 0 | 0 | 0 | 0 | 0 | 0 | 0 | 0 | 0 | 0 | 0 | 0 | 0 | 0 | 0 | 2 |
| 127 | 5.6 | 3 | 3 | 3 | 3 | 3 | 3 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 2 | 3 | 3 | 3 | 3 | 0 | 3 | 3 | 2 | 3 | 3 | 2 | 3 | 3 | 3 | 3 |
| | 0.056 | 2 | 0 | 1 | 2 | 3 | 0 | 3 | 0 | 1 | 2 | 1 | 1 | 2 | 3 | 3 | 3 |
| | 0.0112 | 0 | 0 | 0 | 1 | 1 | 0 | 0 | 0 | 0 | 1 | 0 | 0 | 0 | 1 | 1 | 3 |
| 128 | 5.6 | 3 | 3 | 3 | 3 | 3 | 3 | 3 | 3 | 3 | 3 | 3 | 3 | 3 | 3 | 3 | 3 |
| | 1.12 | 3 | 3 | 3 | 3 | 3 | 0 | 3 | 3 | 2 | 3 | 3 | 3 | 3 | 3 | 3 | 3 |
| | 0.28 | 1 | 2 | 1 | 1 | 2 | 0 | 3 | 2 | 2 | 3 | 3 | 1 | 3 | 3 | 3 | 3 |
| | 0.056 | 0 | 0 | 0 | 0 | 1 | 0 | 0 | 1 | 0 | 0 | 0 | 0 | 2 | 3 | 3 | 3 |
| | 0.0112 | 0 | 0 | 0 | 0 | 0 | 0 | 0 | 0 | 0 | 0 | 0 | 0 | 1 | 0 | 0 | 0 |
| 129 | 5.6 | 2 | 2 | 3 | 3 | 3 | 0 | 2 | 3 | 3 | 3 | 3 | 1 | 3 | 3 | 3 | 3 |
| | 1.12 | 0 | 0 | 1 | 0 | 1 | 0 | 1 | 1 | 0 | 0 | 1 | 0 | 3 | 1 | 2 | 1 |

TABLE 3-continued

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 0.28 | 0 | 0 | 0 | 0 | 0 | 0 | 1 | 0 | 0 | 1 | 0 | 0 | 0 | 0 | 0 | 1 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 130 | 5.6 | 0 | 3 | 0 | 0 | 2 | 0 | 0 | 2 | 0 | 3 | 3 | 0 | 2 | 1 | 2 | 2 |
| | 1.12 | 0 | 3 | 0 | 0 | 0 | 0 | N | 2 | 0 | 2 | 1 | 0 | 2 | 0 | 0 | 0 |
| | 0.28 | 0 | 1 | 0 | 0 | 0 | 0 | 1 | 0 | 0 | 0 | 0 | 0 | 2 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 131 | 5.6 | 0 | 0 | 3 | 2 | 3 | 0 | 0 | 0 | 0 | 0 | 0 | 0 | 3 | 3 | 3 | 3 |
| | 1.12 | 0 | 0 | 1 | 0 | 2 | 0 | 0 | 0 | 0 | 0 | 0 | 0 | 3 | 1 | 2 | 1 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | N | 0 | 0 | 0 | 0 | 0 | 0 | 0 | 0 | 0 |
| 132 | 5.6 | 0 | 1 | 3 | 1 | 0 | 0 | 0 | 0 | 1 | 2 | 1 | 0 | 3 | 3 | 3 | 3 |
| | 1.12 | 0 | 0 | 0 | 0 | 0 | 0 | 0 | 0 | 0 | 0 | 0 | 0 | 2 | 1 | 0 | 1 |
| | 0.28 | 0 | 0 | 0 | 0 | 0 | 0 | 0 | 0 | 0 | 0 | 0 | 0 | 0 | 0 | 0 | 0 |
| 133 | 5.6 | 1 | 2 | 2 | 2 | 3 | 0 | 3 | 2 | 2 | 3 | 3 | 2 | 3 | 3 | 3 | 3 |
| | 1.12 | 0 | 0 | 0 | 0 | 0 | 0 | 0 | 0 | 0 | 1 | 0 | 0 | 2 | 2 | 3 | 2 |
| | 0.28 | 0 | 0 | 0 | 0 | 0 | 0 | 0 | 0 | 0 | 0 | 0 | 0 | 0 | 0 | 0 | 3 |
| | 0.056 | 0 | 0 | 0 | 0 | 0 | 0 | 0 | 0 | 0 | 0 | 0 | 0 | 0 | 0 | 0 | 1 |
| 134 | 5.6 | 1 | 2 | 2 | 3 | 3 | 0 | 3 | 2 | 2 | 3 | 3 | 2 | 3 | 3 | 3 | 3 |
| | 1.12 | 0 | 2 | 0 | 0 | 0 | 0 | 0 | 0 | 0 | 3 | 0 | 0 | 1 | 2 | 2 | 2 |
| | 0.28 | 0 | 0 | 0 | 0 | 0 | 0 | 0 | 0 | 0 | 0 | 0 | 0 | 0 | 0 | 0 | 2 |
| | 0.056 | 0 | 0 | 0 | 0 | 0 | 0 | 0 | 0 | 0 | 0 | 0 | 0 | 0 | 0 | 0 | 0 |
| 135 | 5.6 | 0 | 3 | 0 | 0 | 0 | 0 | 2 | 2 | 2 | 3 | 3 | 0 | 1 | 1 | 0 | 0 |
| | 1.12 | 0 | 3 | 0 | 0 | 0 | 0 | 2 | 2 | 1 | 2 | 1 | 0 | 0 | 0 | 0 | 0 |
| | 0.28 | 0 | 1 | 0 | 0 | 0 | 0 | 0 | 0 | 0 | 0 | 0 | 0 | 0 | 0 | 0 | 0 |
| 137 | 5.6 | 0 | 3 | 1 | 1 | 3 | 0 | 0 | 0 | 1 | 2 | 1 | 0 | 3 | 3 | 3 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 3 | 2 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 139 | 5.6 | 0 | 3 | 0 | 0 | 0 | 0 | 0 | 0 | 0 | 2 | 1 | 1 | 1 | 1 | 2 | 3 |
| | 1.12 | 0 | 1 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 141 | 5.6 | 0 | 2 | 0 | 0 | 0 | 0 | 0 | 0 | 0 | 0 | 0 | 0 | 0 | 1 | 1 | 2 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 147 | 5.6 | 1 | 0 | 3 | 2 | 3 | 0 | 2 | 2 | 1 | 3 | 3 | 0 | 3 | 3 | 3 | 3 |
| | 1.12 | 0 | 0 | 0 | 1 | 0 | 0 | 1 | 0 | 0 | 1 | 0 | 0 | 3 | 2 | 3 | 1 |
| | 0.28 | 0 | 0 | 0 | 0 | 0 | 0 | 0 | 0 | 0 | 0 | 0 | 0 | 0 | 0 | 0 | 0 |
| 148 | 5.6 | 0 | 0 | 0 | 0 | 0 | 0 | 3 | 0 | 0 | 3 | 1 | 0 | 3 | 0 | 3 | 3 |
| | 1.12 | 0 | 1 | 0 | 0 | 0 | 0 | 3 | 1 | 0 | 2 | 1 | 0 | 3 | 1 | 0 | 0 |
| | 0.28 | 0 | 0 | 0 | 0 | 0 | 0 | 0 | 0 | 0 | 0 | 0 | 0 | 2 | 0 | 0 | 0 |
| 149 | 5.6 | 3 | 3 | 3 | 3 | 3 | 0 | 3 | 3 | 3 | 3 | 3 | 3 | 3 | 3 | 3 | 3 |
| | 1.12 | 0 | 1 | 2 | 2 | 3 | 0 | 3 | 2 | 2 | 3 | 3 | 2 | 3 | 3 | 3 | 3 |
| | 0.28 | 0 | 0 | 0 | 0 | 1 | 0 | 3 | 0 | 1 | 3 | 0 | 0 | 1 | 3 | 3 | 3 |
| | 0.056 | 0 | 0 | 0 | 0 | 0 | 0 | 2 | 0 | 0 | 1 | 0 | 0 | 1 | 0 | 0 | 1 |
| | 0.0112 | 0 | 0 | 0 | 0 | 0 | 0 | 2 | 0 | 0 | 1 | 0 | 0 | 1 | 1 | 0 | 1 |
| 150 | 5.6 | 2 | 0 | 3 | 2 | 1 | 0 | 1 | 1 | 1 | 3 | 3 | 0 | 3 | 3 | 3 | 3 |
| | 1.12 | 0 | 0 | 0 | 0 | 0 | 0 | 0 | 0 | 0 | 0 | 0 | 0 | 0 | 0 | 0 | 1 |
| | 0.28 | 0 | 0 | 0 | 0 | 0 | 0 | 0 | 0 | 0 | 0 | 0 | 0 | 0 | 0 | 0 | 0 |
| 151 | 5.6 | 0 | 1 | 0 | 1 | 3 | 0 | 1 | 2 | 1 | 3 | 2 | 0 | 3 | 3 | 3 | 3 |
| | 1.12 | 0 | 0 | 0 | 1 | 1 | 0 | 0 | 0 | 0 | 1 | 0 | 0 | 1 | 0 | 0 | 1 |
| | 0.28 | 0 | 0 | 0 | 0 | 0 | 0 | 0 | 0 | 0 | 0 | 1 | 0 | 0 | 1 | 0 | 1 |
| | 0.056 | 0 | 0 | 0 | 0 | 0 | 0 | 0 | 0 | 0 | 0 | 0 | 0 | 0 | 0 | 0 | 0 |
| 153 | 5.6 | N | 2 | 0 | 2 | 2 | 0 | 2 | 2 | 2 | 3 | 3 | 1 | 3 | 3 | 3 | 3 |
| | 1.12 | 0 | 1 | 0 | 1 | 1 | 0 | 0 | 0 | 0 | 1 | 1 | 0 | 1 | 0 | 2 | 2 |
| | 0.28 | 0 | 1 | 0 | 0 | 1 | 0 | 0 | 0 | 0 | 1 | 0 | 0 | 0 | 1 | 0 | 1 |
| | 0.056 | 0 | 0 | 0 | 0 | 0 | 0 | 0 | 0 | 0 | 0 | 0 | 0 | 0 | 0 | 0 | 1 |
| 155 | 5.6 | 0 | 3 | 0 | 0 | 1 | 0 | 2 | 3 | 0 | 2 | 2 | 0 | 3 | 0 | 0 | 1 |
| | 1.12 | 0 | 2 | 0 | 0 | 0 | 0 | 1 | 2 | 0 | 2 | 1 | 0 | 1 | 0 | 1 | 0 |
| | 0.28 | 0 | 0 | 0 | 0 | 0 | 0 | 0 | 1 | 0 | 0 | 0 | 0 | 0 | 0 | 0 | 0 |
| 156 | 5.6 | 3 | 3 | 3 | 3 | 3 | 1 | 3 | 3 | 3 | 3 | 3 | 3 | 3 | 3 | 3 | 3 |
| | 1.12 | 3 | 3 | 3 | 3 | 3 | 0 | 3 | 2 | 2 | 3 | 3 | 3 | 3 | 3 | 3 | 3 |
| | 0.28 | 1 | 1 | 2 | 2 | 3 | 0 | 2 | 1 | 2 | 3 | 3 | 2 | 2 | 3 | 3 | 3 |
| | 0.056 | 0 | 0 | 0 | 0 | 1 | 0 | 1 | 0 | 1 | 2 | 1 | 0 | 0 | 1 | 2 | 3 |
| | 0.0112 | 0 | 0 | 0 | 0 | 0 | 0 | 0 | 0 | 0 | 1 | 0 | 0 | 0 | 0 | 1 | 1 |
| 157 | 5.6 | 3 | 3 | 3 | 3 | 1 | 0 | 3 | 3 | 3 | 3 | 3 | 2 | 3 | 3 | 3 | 3 |
| | 1.12 | 3 | 2 | 1 | 2 | 0 | 0 | 0 | 2 | 2 | 3 | 3 | 2 | 2 | 3 | 3 | 3 |
| | 0.28 | 1 | 1 | 0 | 0 | 0 | 0 | 0 | 1 | 0 | 0 | 0 | 0 | 0 | 2 | 2 | 3 |
| | 0.056 | 0 | 0 | 0 | 0 | 0 | 0 | 0 | 0 | 0 | 0 | 0 | 0 | 0 | 0 | 0 | 0 |
| 158 | 5.6 | 0 | 1 | 2 | 1 | 3 | 0 | 1 | 3 | 2 | 2 | 2 | 0 | 3 | 3 | 3 | 3 |
| | 1.12 | 0 | 0 | 1 | 1 | 0 | 0 | 3 | 0 | 0 | 0 | 1 | 0 | 0 | 2 | 3 | 2 |
| | 0.28 | 0 | 0 | 0 | 0 | 0 | 0 | 3 | 1 | 0 | 0 | 0 | 0 | 2 | 0 | 0 | 0 |
| | 0.056 | 0 | 0 | 0 | 0 | 0 | 0 | 3 | 1 | 0 | 0 | 0 | 0 | 0 | 0 | 0 | 0 |
| | 0.0112 | 0 | 0 | 0 | 0 | 0 | 0 | 2 | 0 | 0 | 0 | 0 | 0 | 1 | 0 | 0 | 0 |
| 159 | 5.6 | 0 | 0 | 1 | 1 | 2 | 0 | 1 | 2 | 1 | 1 | 2 | 0 | 2 | 3 | 3 | 3 |
| | 1.12 | 0 | 0 | 0 | 0 | 0 | 0 | 1 | 1 | 0 | 1 | 0 | 0 | 0 | 0 | 0 | 2 |
| | 0.28 | 0 | 0 | 0 | 0 | 0 | 0 | 0 | 0 | 0 | 0 | 0 | 0 | 0 | 0 | 0 | 0 |
| 160 | 5.6 | 0 | 1 | 1 | 0 | 0 | 0 | 0 | 0 | 0 | 0 | 0 | 0 | 1 | 0 | 2 | 0 |
| | 1.12 | 0 | 0 | 0 | 0 | 0 | 0 | 0 | 0 | 0 | 0 | 0 | 0 | 0 | 0 | 0 | 0 |
| 162 | 5.6 | 0 | 1 | 0 | 0 | 3 | 0 | 0 | 1 | 1 | 3 | 2 | 1 | 3 | 3 | 3 | 3 |

TABLE 3-continued
PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 1.12 | 0 | 0 | 0 | 0 | 0 | 0 | 0 | N | 0 | 0 | 1 | 0 | 0 | 0 | 2 | 0 |
| | 0.28 | 0 | 0 | 0 | 0 | 0 | 0 | 0 | 0 | 0 | 0 | 0 | 0 | 0 | 0 | 0 | 0 |
| 163 | 5.6 | 0 | 0 | 0 | 0 | 1 | 0 | 1 | N | 1 | 3 | 2 | 0 | 2 | 3 | 3 | 3 |
| | 1.12 | 0 | 0 | 0 | 0 | 0 | 0 | 0 | 0 | 0 | 0 | 0 | 0 | 0 | 0 | 1 | 0 |
| | 0.28 | 0 | 0 | 0 | 0 | 0 | 0 | 0 | 0 | 0 | 0 | 0 | 0 | 0 | 0 | 0 | 0 |
| 164 | 5.6 | 2 | 3 | 1 | 0 | 3 | 0 | 3 | 3 | 3 | 3 | 3 | 2 | 3 | 3 | 3 | 3 |
| | 1.12 | 0 | 1 | 0 | 0 | 2 | 0 | 0 | N | 0 | 3 | 1 | 1 | 3 | 3 | 3 | 3 |
| | 0.28 | 0 | 0 | 0 | 0 | 0 | 0 | 0 | 0 | 0 | 0 | 0 | 0 | 0 | 2 | 2 | 2 |
| | 0.056 | 0 | 0 | 0 | 0 | 0 | 0 | 0 | 0 | 0 | 0 | 0 | 0 | 0 | 0 | 0 | 0 |
| 165 | 5.6 | 0 | 3 | 3 | 3 | 3 | 0 | 1 | 2 | 2 | 3 | 3 | 2 | 3 | 3 | 3 | 3 |
| | 1.12 | 0 | 1 | 0 | 1 | 2 | 0 | 0 | 1 | 0 | 0 | 1 | 0 | 2 | 3 | 3 | 3 |
| | 0.28 | 0 | 0 | 0 | 0 | 1 | 0 | 0 | 0 | 0 | 0 | 0 | 0 | 0 | 0 | 1 | 1 |
| | 0.056 | 0 | 0 | 0 | 0 | 0 | 0 | 0 | 0 | 0 | 0 | 0 | 0 | 0 | 0 | 0 | 0 |
| 166 | 5.6 | 3 | 2 | 3 | 0 | 2 | 0 | 3 | 1 | 0 | 3 | 3 | 1 | 3 | 3 | 3 | 3 |
| | 1.12 | 0 | 0 | 0 | 0 | 0 | 0 | 0 | N | 0 | 2 | 1 | 0 | 0 | 0 | 0 | 2 |
| | 0.56 | 0 | 0 | 0 | 0 | 0 | 0 | 0 | 0 | 0 | 1 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| | 0.014 | 0 | 0 | 0 | 0 | 0 | 0 | 0 | 0 | 0 | 0 | 0 | 0 | 0 | 0 | 0 | 0 |
| 167 | 5.6 | 1 | 3 | 1 | 2 | 0 | 0 | 2 | 2 | 0 | 3 | 2 | 1 | 3 | 0 | 1 | 2 |
| | 1.12 | 0 | 1 | 0 | 0 | 0 | 0 | 1 | 0 | 0 | 2 | 0 | 0 | 1 | 0 | 0 | 0 |
| | 0.28 | 0 | 1 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 168 | 5.6 | 3 | 3 | 3 | 3 | 3 | 0 | 3 | 3 | 3 | 3 | 3 | 3 | 3 | 3 | 3 | 3 |
| | 1.12 | 0 | 3 | 2 | 2 | 3 | 0 | 3 | 3 | 2 | 3 | 3 | 2 | 3 | 3 | 3 | 3 |
| | 0.28 | 0 | 0 | 1 | 1 | 0 | 0 | 0 | 1 | 0 | 3 | 1 | 0 | 2 | 2 | 3 | 3 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 169 | 5.6 | 0 | 3 | 0 | 1 | 0 | 0 | 1 | 0 | 0 | 3 | 1 | 0 | 1 | 1 | 0 | 3 |
| | 1.12 | 0 | 0 | 0 | 0 | 0 | 0 | 0 | 0 | 0 | 2 | 0 | 0 | 0 | 0 | 0 | 2 |
| | 0.28 | 0 | 0 | 0 | 0 | 0 | 0 | 0 | 0 | 0 | 0 | 0 | 0 | 0 | 0 | 0 | 0 |
| 170 | 5.6 | 3 | 3 | 3 | 3 | 3 | 3 | 3 | 3 | 3 | 3 | 3 | 3 | 3 | 3 | 3 | 3 |
| | 1.12 | 3 | 3 | 3 | 3 | 3 | 2 | 3 | 3 | 3 | 3 | 3 | 3 | 3 | 3 | 3 | 3 |
| | 0.28 | 1 | 3 | 3 | 3 | 3 | 0 | 3 | 3 | 3 | 3 | 3 | 3 | 3 | 3 | 3 | 3 |
| | 0.056 | 0 | 3 | 2 | 3 | 3 | 0 | 3 | 0 | 3 | 3 | 3 | 3 | 3 | 3 | 3 | 3 |
| | 0.0112 | 0 | 2 | 0 | 0 | 1 | 0 | 1 | 0 | 0 | 3 | 2 | 1 | 0 | 1 | 3 | 3 |
| 171 | 5.6 | 3 | 3 | 3 | 3 | 3 | 2 | 3 | 3 | 3 | 3 | 3 | 3 | 3 | 3 | 3 | 3 |
| | 1.12 | 3 | 3 | 3 | 3 | 3 | 1 | 3 | 3 | 3 | 3 | 3 | 3 | 3 | 3 | 3 | 3 |
| | 0.28 | 0 | 2 | 3 | 3 | 3 | 0 | 2 | 2 | 2 | 3 | 3 | 2 | 3 | 3 | 3 | 3 |
| | 0.056 | 0 | 0 | 1 | 1 | 3 | 0 | 0 | 0 | 0 | 2 | 2 | 0 | 2 | 3 | 3 | 3 |
| | 0.0112 | 0 | 0 | 0 | 0 | 0 | 0 | 0 | 0 | 0 | 1 | 0 | 0 | 0 | 0 | 2 | 3 |
| 172 | 5.6 | 3 | 3 | 3 | 3 | 3 | 2 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 0 | 2 | 2 | 2 | 3 | 0 | 2 | 0 | 1 | 3 | 3 | 1 | 3 | 3 | 3 | 3 |
| | 0.056 | 0 | 0 | 0 | 1 | 0 | 0 | 1 | 0 | 0 | 0 | 0 | 0 | 2 | 2 | 2 | 3 |
| | 0.0112 | 0 | 0 | 0 | 0 | 0 | 0 | 0 | 0 | 1 | 1 | 1 | 1 | 1 | 0 | 0 | 0 |
| 173 | 5.6 | 3 | 3 | 3 | 3 | 3 | 1 | 3 | 3 | 3 | 3 | 3 | 2 | 3 | 3 | 3 | 3 |
| | 1.12 | 0 | 3 | 1 | 1 | 3 | 0 | 3 | 3 | 3 | 3 | 3 | 1 | 3 | 3 | 3 | 3 |
| | 0.28 | 0 | 2 | 0 | 0 | 3 | 0 | 0 | 1 | 2 | 2 | 3 | 0 | 3 | 3 | 3 | 3 |
| | 0.056 | 0 | 1 | 0 | 0 | 0 | 0 | 0 | 0 | 1 | 0 | 1 | 0 | 1 | 2 | 3 | 2 |
| | 0.0112 | 0 | 0 | 0 | 0 | 0 | 0 | 0 | N | 0 | 0 | 1 | 0 | 0 | 0 | 0 | 0 |
| 174 | 5.6 | 0 | 2 | 0 | 1 | 0 | 0 | 0 | 0 | 0 | 3 | 1 | 0 | 3 | 0 | 0 | 2 |
| | 1.12 | 0 | 0 | 0 | 0 | 0 | 0 | 0 | 0 | 0 | 1 | 0 | 0 | 2 | 0 | 0 | 1 |
| 175 | 5.6 | 0 | 3 | 1 | 1 | 3 | 0 | 0 | 1 | 1 | 2 | 3 | 1 | 3 | 3 | 3 | 3 |
| | 1.12 | 0 | 0 | 0 | 0 | 0 | 0 | 0 | 0 | 0 | 0 | 1 | 0 | 2 | 1 | 3 | 3 |
| | 0.28 | 0 | 0 | 0 | 0 | 0 | 0 | 0 | 0 | 0 | 0 | 0 | 0 | 0 | 0 | 0 | 0 |
| 176 | 5.6 | 1 | 3 | 3 | 3 | 3 | 0 | 3 | 2 | 3 | 3 | 3 | 2 | 3 | 3 | 3 | 3 |
| | 1.12 | 0 | 3 | 2 | 1 | 3 | 0 | 2 | 0 | 1 | 3 | 2 | 0 | 3 | 3 | 3 | 3 |
| | 0.28 | 0 | 1 | 0 | 0 | 0 | 0 | 0 | 0 | 0 | 0 | 0 | 0 | 3 | 0 | 2 | 2 |
| | 0.056 | 0 | 0 | 0 | 0 | 0 | 0 | 0 | 0 | 0 | 0 | 0 | 0 | 0 | 0 | 0 | 0 |
| 177 | 5.6 | 2 | 3 | 1 | 1 | 0 | 0 | 2 | 0 | 1 | 3 | 2 | 1 | 3 | 1 | 3 | 3 |
| | 1.12 | 0 | 0 | 0 | 0 | 0 | 0 | 1 | 0 | 0 | 0 | 0 | 0 | 0 | 0 | 0 | 1 |
| 178 | 5.6 | 3 | 3 | 3 | 3 | 3 | 1 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 2 | 3 | 3 | 3 | 3 |
| | 0.28 | 0 | 3 | 1 | 1 | 3 | 0 | 3 | 2 | 2 | 3 | 3 | 0 | 3 | 3 | 3 | 3 |
| | 0.056 | 0 | 0 | 0 | 0 | 0 | 3 | 0 | 0 | 0 | 0 | 0 | 3 | 3 | 3 | 3 | 3 |
| | 0.0112 | 0 | 0 | 0 | 0 | 0 | 0 | 0 | 0 | 0 | 0 | 0 | 1 | 1 | 1 | 1 | 2 |
| 179 | 5.6 | 0 | 3 | 0 | 0 | 0 | 0 | 0 | 0 | 0 | 2 | 1 | 0 | 2 | 1 | 2 | 2 |
| | 1.12 | 0 | 2 | 0 | 0 | 0 | 0 | 0 | 0 | 0 | 0 | 0 | 0 | 0 | 0 | 0 | 0 |
| 180 | 5.6 | 3 | 3 | 3 | 3 | 3 | 2 | 3 | 3 | 3 | 3 | 3 | 3 | 3 | 3 | 3 | 3 |
| | 1.12 | 0 | 2 | 2 | 2 | 2 | 0 | 2 | 2 | 2 | 3 | 3 | 2 | 2 | 3 | 3 | 3 |
| | 0.56 | 0 | 0 | 2 | 0 | 1 | 0 | 1 | 1 | 0 | 2 | 3 | 0 | 2 | 3 | 3 | 3 |
| | 0.28 | 0 | 0 | 1 | 0 | 1 | 0 | 0 | 0 | 0 | 0 | 2 | 0 | 2 | 3 | 3 | 3 |
| | 0.14 | 0 | 0 | 0 | 0 | 0 | 0 | 0 | 0 | 0 | 0 | 1 | 0 | 1 | 1 | 3 | 3 |
| | 0.07 | 0 | 1 | 1 | 0 | 0 | 0 | 0 | 0 | 0 | 1 | 0 | 0 | 1 | 0 | 1 | 1 |
| | 0.035 | 0 | 0 | 0 | 0 | 0 | 0 | 0 | 0 | 0 | 0 | 0 | 0 | 0 | 0 | 0 | 0 |
| | 0.0182 | 0 | 0 | 0 | 0 | 0 | 0 | 0 | 0 | 0 | 0 | 0 | 0 | 0 | 0 | 0 | 0 |
| 181 | 5.6 | 0 | 3 | 0 | 0 | 0 | 0 | 2 | 0 | 0 | 2 | 2 | 0 | 1 | 1 | 3 | 2 |
| | 1.12 | 0 | 2 | 0 | 0 | 0 | 0 | 0 | 0 | 0 | 2 | 2 | 0 | 0 | 0 | 0 | 0 |
| | 0.56 | 0 | 0 | 0 | 0 | 0 | 0 | 0 | 0 | 0 | 0 | 0 | 0 | 0 | 0 | 0 | 0 |
| 182 | 5.6 | 0 | 1 | 0 | 1 | 3 | 0 | 1 | 1 | 1 | 2 | 2 | 0 | 3 | 3 | 3 | 3 |

TABLE 3-continued

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 1.12 | 0 | 0 | 0 | 0 | 0 | 0 | 0 | 0 | 0 | 0 | 1 | 0 | 0 | 0 | 2 | 3 |
| | 0.28 | 0 | 0 | 0 | 0 | 0 | 0 | 0 | 0 | 0 | 0 | 0 | 0 | 0 | 0 | 0 | 1 |
| 183 | 5.6 | 1 | 3 | 3 | 3 | 3 | 0 | 3 | 2 | 3 | 3 | 3 | 1 | 3 | 3 | 3 | 3 |
| | 1.12 | 0 | 0 | 2 | 1 | 3 | 0 | 0 | 1 | 1 | 2 | 1 | N | 1 | 3 | 3 | 3 |
| | 0.28 | 1 | 0 | 0 | 0 | 1 | 0 | 0 | 0 | 0 | 0 | 1 | 0 | 0 | 0 | 3 | 2 |
| | 0.056 | 0 | 0 | 0 | 0 | 0 | 0 | 0 | 0 | 0 | 0 | 0 | 0 | 0 | 0 | 0 | 1 |
| 184 | 5.6 | 1 | 0 | 1 | 0 | 2 | 0 | 0 | 0 | 0 | 0 | 2 | 0 | 2 | 3 | 3 | 3 |
| | 1.12 | 0 | 0 | 1 | 0 | 0 | 0 | 0 | 0 | 0 | 0 | 1 | 0 | 0 | 0 | 1 | 0 |
| | 0.28 | 0 | 0 | 0 | 0 | 0 | 0 | 0 | 0 | 0 | 0 | 0 | 0 | 0 | 0 | 1 | 1 |
| 185 | 5.6 | 0 | 1 | 0 | 1 | 3 | 0 | 1 | 1 | 1 | 0 | 2 | 0 | 3 | 3 | 3 | 3 |
| | 1.12 | 0 | 0 | 0 | 0 | 0 | 0 | 0 | 0 | 0 | 0 | 0 | 0 | 0 | 0 | 1 | 1 |
| | 0.28 | 0 | 0 | 0 | 0 | 0 | 0 | 0 | 0 | 0 | 0 | 0 | 0 | 0 | 0 | 0 | 1 |
| 186 | 5.6 | 0 | 3 | 0 | 1 | 0 | 1 | 0 | 2 | 2 | 2 | 2 | 1 | 1 | 0 | 1 | 3 |
| | 1.12 | 0 | 2 | 0 | 0 | 0 | 0 | 0 | 0 | 1 | 2 | 2 | 1 | 0 | 0 | 0 | 1 |
| 188 | 5.6 | 3 | 3 | 3 | 3 | 3 | 0 | 3 | 3 | 3 | 3 | 3 | 3 | 3 | 3 | 3 | 3 |
| | 1.12 | 0 | 3 | 2 | 2 | 2 | 0 | 2 | 2 | 3 | 2 | 3 | 3 | 2 | 3 | 3 | 3 |
| | 0.56 | 0 | 3 | 1 | 1 | 2 | 0 | 2 | 2 | 2 | 2 | 3 | 2 | 2 | 3 | 3 | 3 |
| | 0.28 | 0 | 2 | 0 | 1 | 1 | 0 | 1 | 1 | 2 | 1 | 3 | 0 | 1 | 3 | 3 | 3 |
| | 0.14 | 0 | 1 | 0 | 0 | 1 | 0 | 0 | 0 | 0 | 0 | 2 | 0 | 0 | 2 | 3 | 3 |
| | 0.07 | 0 | 1 | 0 | 0 | 0 | 0 | 0 | 0 | 0 | 1 | 0 | 0 | 0 | 0 | 1 | 2 |
| 190 | 5.6 | 1 | 3 | 1 | 2 | 2 | 1 | 3 | 2 | 2 | 3 | 3 | 2 | 3 | 3 | 3 | 3 |
| | 1.12 | 1 | 3 | 1 | 1 | 1 | 1 | 2 | 1 | 0 | 3 | 2 | 1 | 3 | 2 | 3 | 3 |
| | 0.56 | 0 | 0 | 1 | 0 | 1 | 0 | 2 | 0 | 0 | 1 | 1 | 0 | 2 | 1 | 1 | 2 |
| | 0.28 | 0 | 1 | 1 | 1 | 0 | 0 | 2 | 0 | 0 | 0 | 0 | 0 | 0 | 0 | 0 | 0 |
| | 0.14 | 0 | 1 | 0 | 0 | 0 | 0 | 2 | 0 | 0 | 0 | 0 | 0 | 0 | 0 | 0 | 1 |
| | 0.07 | 0 | 1 | 0 | 0 | 0 | 0 | 2 | 0 | 0 | 1 | 0 | 0 | 2 | 0 | 0 | 1 |
| | 0.035 | 0 | 1 | 2 | 1 | 0 | 0 | 1 | 0 | 0 | 1 | 1 | 0 | 1 | 0 | 0 | 0 |
| 191 | 5.6 | 3 | 3 | 3 | 3 | 3 | 1 | 3 | 3 | 3 | 3 | 3 | 3 | 3 | 3 | 3 | 3 |
| | 1.12 | 1 | 3 | 3 | 3 | 3 | 0 | 3 | 2 | 2 | 3 | 3 | 3 | 3 | 3 | 3 | 3 |
| | 0.56 | 0 | 3 | 3 | 3 | 3 | 0 | 2 | 1 | 2 | 3 | 3 | 2 | 3 | 3 | 3 | 3 |
| | 0.28 | 0 | 1 | 2 | 2 | 3 | 0 | 1 | 0 | 1 | 2 | 2 | 0 | 3 | 3 | 3 | 3 |
| | 0.14 | 0 | 1 | 1 | 1 | 3 | 0 | 1 | 0 | 0 | 0 | 2 | 0 | 2 | 2 | 3 | 2 |
| | 0.07 | 0 | 0 | 0 | 1 | 1 | 0 | 0 | 0 | 0 | 0 | 1 | 0 | 3 | 3 | 3 | 1 |
| | 0.035 | 0 | 0 | 0 | 0 | 0 | 0 | 0 | 0 | 0 | 1 | 0 | 1 | 0 | 1 | 0 | 0 |
| | 0.0182 | 0 | 0 | 0 | 0 | 0 | 0 | 0 | 0 | 0 | 0 | 0 | 0 | 0 | 0 | 0 | 0 |
| | 0.009 | 0 | 0 | 0 | 0 | 0 | 0 | 0 | 0 | 0 | 0 | N | 0 | 0 | 0 | 0 | 0 |
| 192 | 5.6 | 0 | 2 | 1 | 0 | 3 | 0 | 2 | 2 | 1 | 3 | 3 | 3 | 3 | 3 | 3 | 3 |
| | 1.12 | 0 | 1 | 0 | 0 | 0 | 0 | 0 | 0 | 1 | 3 | 1 | 0 | 0 | 1 | 3 | 3 |
| | 0.56 | 0 | 1 | 0 | 0 | 0 | 0 | 0 | 0 | 1 | 2 | 1 | 1 | 0 | 0 | 0 | 1 |
| | 0.28 | 0 | 0 | 0 | 0 | 0 | 0 | 0 | 1 | 0 | 0 | 0 | 0 | 0 | 0 | 0 | 0 |
| | 0.14 | 0 | 0 | 0 | 0 | 0 | 0 | 1 | 0 | 0 | 2 | 0 | 0 | 1 | 0 | 0 | 0 |
| 193 | 5.6 | 0 | 0 | 0 | 0 | 0 | 0 | 0 | 0 | 0 | 0 | 0 | 0 | 0 | 0 | 0 | 0 |
| | 1.12 | 0 | 1 | 0 | 0 | 0 | 0 | 0 | 0 | 0 | 0 | 0 | 0 | 0 | 0 | 0 | 0 |
| | 0.56 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |

POST-EMERGENT HERBICIDE EXAMPLES

The post-emergence herbicidal activity of some of the various compounds of this invention was demonstrated by greenhouse testing in the following manner. Top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a bench in the greenhouse and watered from below as needed. After the plants reach the desired age (two to three weeks), each pan, is removed individually to a spraying chamber and sprayed by means of an atomizer, operating at a spray pressure of 170.3 kPa (10 psig) at the application rates noted. In the spray solution is an amount of an emulsifying agent mixture to give a spray solution or suspension which contains about 0.4% by volume of the emulsifier. The spray solution or suspension contains a sufficient amount of the candidate chemical in order to give application rates of the active ingredient corresponding to those shown in the Tables while applying a total amount of solution or suspension equivalent to 1870 L/Ha (200 gallons/acre). The pans were returned to the greenhouse and watered as before and the injury to the plants as compared to the control is observed at approximately 10–14 days (usually 11 days) and in some instances observed again at 24–28 days (usually 25 days) after spraying. These latter observations are designated by an asterisk (*) following the column of example numbers in the Table.

The post-emergent herbicidal activity index used in Table 4 is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — |
| Species planted, no data | N |

TABLE 4

POST-EMERGENT ACTIVITY FOR WEEDS

| Example No. | Kg/ha | A | B | C | D | E | F | G | H | I | J | K |
|---|---|---|---|---|---|---|---|---|---|---|---|---|
| 1 | 11.2 | 0 | 0 | 0 | 0 | 0 | 0 | 0 | 0 | 0 | 0 | 0 |

TABLE 4-continued
POST-EMERGENT ACTIVITY FOR WEEDS

| Example No. | Kg/ha | A | B | C | D | E | F | G | H | I | J | K |
|---|---|---|---|---|---|---|---|---|---|---|---|---|
| 2 | 11.2 | 0 | 0 | 0 | 0 | 0 | 0 | 0 | 0 | 0 | 0 | 0 |
| 3 | 11.2 | 0 | 0 | 0 | 0 | 0 | 0 | 0 | 0 | — | 0 | 0 |
| 4 | 11.2 | 0 | 0 | 0 | 0 | 0 | 0 | 1 | 0 | — | 0 | 1 |
| 5 | 11.2 | 0 | N | 0 | 1 | 0 | 0 | 0 | 0 | 0 | 0 | 0 |
| 6 | 11.2 | 0 | 0 | 0 | 0 | 0 | 0 | 0 | 0 | — | 0 | 0 |
| 7 | 11.2 | N | 3 | 1 | 3 | 4 | 1 | 0 | 0 | 0 | 0 | 2 |
| 7* | 11.2 | N | 4 | 1 | 3 | 4 | 1 | 0 | 0 | 0 | 0 | 1 |
| 7* | 11.2 | N | 3 | 1 | 3 | 3 | 0 | 0 | 0 | 0 | 0 | 1 |
| 8 | 11.2 | 0 | 0 | 0 | 0 | 0 | 0 | 0 | 0 | 0 | 0 | 0 |
| 9 | 11.2 | 0 | 0 | 0 | 0 | 0 | 0 | 0 | 0 | 0 | 0 | 0 |
| 10 | 11.2 | N | 0 | 1 | 0 | 0 | 0 | 0 | 0 | 0 | 0 | 0 |
| 11 | 11.2 | 0 | N | 0 | 0 | 0 | 0 | 0 | 0 | 0 | 0 | 0 |
| 12 | 11.2 | 0 | 0 | 0 | 0 | 0 | 0 | 0 | 0 | — | 0 | 0 |
| 13 | 11.2 | 0 | N | 0 | 0 | 0 | 0 | 0 | 0 | 0 | 0 | 0 |
| 14 | 11.2 | 0 | 0 | 0 | 0 | 0 | 0 | 0 | 0 | N | 0 | 0 |
| 15 | 11.2 | 0 | N | 0 | 0 | 0 | 0 | 0 | 0 | 0 | 0 | 0 |
| 16 | 11.2 | 0 | 0 | 0 | 0 | 0 | 0 | 0 | 0 | N | 0 | 0 |
| 17 | 11.2 | — | 0 | 1 | 1 | N | 0 | 0 | 0 | 0 | 0 | 1 |
| 18 | 11.2 | — | 0 | 0 | 0 | 0 | 0 | 0 | 1 | 0 | 0 | 1 |
| 19 | 11.2 | — | 0 | 0 | 0 | 0 | 0 | 0 | 0 | 1 | 0 | 0 |
| 20 | 11.2 | — | 0 | 0 | 0 | 0 | 0 | 0 | 0 | 0 | 0 | 0 |
| 21 | 11.2 | — | 0 | 0 | 0 | 0 | 0 | 0 | 0 | 0 | 0 | 0 |
| 22 | 11.2 | — | 0 | 0 | 0 | 0 | 0 | 0 | 0 | 0 | 0 | 0 |
| 23 | 11.2 | — | 0 | 0 | 0 | 0 | 0 | 0 | 0 | 0 | 0 | 0 |
| 24 | 11.2 | — | 0 | 0 | 0 | 0 | 0 | 0 | 0 | 0 | 0 | 0 |
| 25 | 11.2 | N | 0 | 0 | 1 | 1 | 0 | 1 | 1 | 0 | 0 | 1 |
| 26 | 11.2 | — | 0 | 1 | 3 | 3 | 0 | 1 | 0 | 0 | 0 | 1 |
| 26* | 11.2 | — | 1 | 0 | 3 | 3 | 0 | 0 | 0 | 0 | 0 | 1 |
| 27 | 11.2 | — | 1 | 1 | 1 | 1 | 0 | 1 | 0 | 0 | 0 | 1 |
| 28 | 11.2 | — | 1 | 0 | 1 | 3 | 0 | 0 | 0 | 0 | 0 | 0 |
| 29 | 11.2 | — | 0 | 0 | 0 | 0 | 0 | 0 | 0 | 0 | 0 | 0 |
| 30 | 11.2 | — | 0 | 0 | 1 | N | 0 | 0 | 0 | 0 | 0 | 0 |
| 31 | 11.2 | — | 0 | 0 | 1 | 0 | 0 | 0 | 0 | 0 | 0 | 1 |
| 32 | 11.2 | — | 0 | 0 | 0 | 0 | 0 | 0 | 0 | 2 | 0 | 1 |
| 33 | 11.2 | — | 0 | 0 | 0 | 0 | 0 | 0 | 0 | 0 | 0 | 0 |
| 34 | 11.2 | — | 0 | 0 | 0 | 0 | 0 | 0 | 0 | 0 | 0 | 0 |
| 35 | 11.2 | — | 1 | 0 | 0 | 0 | 0 | 0 | 0 | 0 | 0 | 0 |
| 36 | 11.2 | — | 0 | 0 | 0 | 0 | 0 | 0 | 0 | 0 | 0 | 0 |
| 37 | 11.2 | — | 0 | 0 | 0 | 0 | 0 | 0 | 0 | 0 | 0 | 0 |
| 38 | 11.2 | — | 0 | 0 | 0 | 0 | 0 | 0 | 0 | 0 | 0 | 0 |
| 39 | 11.2 | — | 0 | 0 | 0 | 0 | 0 | 0 | 0 | 0 | 0 | 0 |
| 40 | 11.2 | — | 0 | 0 | 0 | 0 | 0 | 0 | 0 | N | 0 | 0 |
| 41 | 11.2 | — | 0 | 0 | 0 | 0 | 0 | 0 | 0 | 0 | 0 | 0 |
| 42 | 11.2 | — | 0 | 0 | 0 | 0 | 0 | 0 | 0 | 0 | 0 | 0 |
| 43 | 11.2 | — | 0 | 0 | 0 | 0 | 0 | 0 | 0 | N | 0 | 0 |
| 44 | 11.2 | — | 0 | 0 | 0 | 0 | 0 | 0 | 0 | N | 0 | 0 |
| 45 | 11.2 | — | 0 | 0 | 1 | 1 | 0 | 0 | 0 | 0 | 0 | 0 |
| 46 | 11.2 | — | 0 | 0 | 0 | 0 | 0 | 0 | 0 | 0 | 0 | 0 |
| 47 | 11.2 | — | 0 | 0 | 0 | 2 | 0 | 0 | 0 | 0 | 0 | 1 |
| 48 | 11.2 | — | 0 | 0 | 0 | 0 | 0 | 0 | 0 | 0 | 0 | 0 |
| 49 | 11.2 | — | 0 | 0 | 0 | 0 | 0 | 0 | 0 | 0 | 0 | 0 |
| 50 | 11.2 | — | 0 | 0 | 0 | 0 | 0 | 0 | 0 | 0 | 0 | 0 |
| 51 | 11.2 | — | 1 | 0 | 0 | 0 | 0 | 0 | 0 | 0 | 0 | 0 |
| 52 | 11.2 | — | 0 | 0 | 0 | 0 | 0 | 0 | 0 | 0 | 0 | 0 |
| 53 | 11.2 | — | 0 | 0 | 0 | 0 | 0 | 0 | 0 | N | 0 | 0 |
| 54 | 11.2 | — | 0 | 0 | 0 | 0 | 0 | 0 | 0 | 0 | 0 | 0 |
| 55 | 11.2 | — | 0 | 0 | 0 | 0 | 0 | 0 | 0 | 0 | 0 | 0 |
| 56 | 11.2 | — | 0 | 0 | 0 | 0 | 0 | 0 | 0 | 0 | 0 | 0 |
| 57 | 11.2 | — | 0 | 0 | 0 | 0 | 0 | 0 | 0 | 0 | 0 | 0 |
| 58 | 11.2 | — | 0 | 0 | 0 | 1 | 0 | 0 | 0 | 0 | 0 | 1 |
| 59 | 11.2 | — | 0 | 0 | 0 | 0 | 0 | 0 | 0 | 0 | 0 | 0 |
| 60 | 11.2 | — | 0 | 0 | 0 | 0 | 0 | 0 | 0 | 0 | 0 | 0 |
| 61 | 11.2 | — | 0 | 0 | 0 | 0 | 0 | 0 | 0 | 0 | 0 | 0 |
| 62 | 11.2 | — | 0 | 0 | 0 | 0 | 0 | 0 | 0 | 0 | 0 | 0 |
| 63 | 11.2 | — | 0 | 0 | 0 | 0 | 0 | 0 | 0 | 0 | 0 | 0 |
| 64 | 11.2 | — | 0 | 0 | 0 | 0 | 0 | 0 | 0 | 0 | 0 | 0 |
| 65 | 11.2 | — | 0 | 0 | 0 | 0 | 0 | 0 | 0 | 0 | 0 | 0 |
| 66 | 11.2 | — | 0 | 0 | 0 | 0 | 0 | 0 | 0 | N | 0 | 0 |
| 67 | 11.2 | — | 1 | 0 | 0 | 0 | 0 | 0 | 0 | 0 | 0 | 0 |
| 68 | 11.2 | — | 0 | 0 | 0 | 0 | 0 | 0 | 0 | 0 | 0 | 0 |
| 69 | 11.2 | — | 0 | 0 | 0 | 0 | 0 | 0 | 0 | 0 | 0 | 0 |
| 70 | 11.2 | — | 0 | 0 | 0 | 0 | 0 | 0 | 0 | 0 | 0 | 0 |
| 71 | 11.2 | 0 | 1 | 1 | 1 | 1 | 0 | 0 | 0 | 0 | 0 | 0 |
| 72 | 11.2 | 0 | 0 | 0 | 0 | 0 | 0 | 0 | 0 | N | 0 | 0 |
| 73 | 11.2 | N | 0 | 0 | 0 | 0 | 0 | 0 | 0 | 0 | 0 | 0 |
| 74 | 11.2 | N | 0 | 0 | 0 | 0 | 0 | 0 | 0 | 0 | 0 | 0 |
| 75 | 11.2 | 0 | 0 | 0 | 0 | 0 | 0 | 0 | 0 | 0 | 0 | 0 |
| 76 | 11.2 | 0 | 0 | 0 | 0 | 0 | 0 | 0 | 0 | 0 | 0 | 0 |
| 77 | 11.2 | 0 | 0 | 0 | 0 | 0 | 0 | 0 | 0 | 0 | 0 | 0 |
| 78 | 11.2 | 0 | 0 | 0 | 0 | 0 | 0 | 0 | 0 | 0 | 0 | 0 |
| 79 | 11.2 | 0 | 0 | 0 | 0 | 0 | 0 | 0 | 0 | 0 | 0 | 0 |
| 80 | 11.2 | 0 | 0 | 0 | 0 | 0 | 0 | 0 | 0 | 0 | 0 | 0 |
| 81 | 11.2 | — | 0 | 0 | 0 | 0 | 0 | 0 | 0 | 0 | 0 | 0 |
| 82 | 11.2 | — | 0 | 0 | 0 | 0 | 0 | 0 | 0 | 0 | 0 | 0 |
| 83 | 11.2 | — | 0 | 0 | 0 | 0 | 0 | 0 | 0 | 0 | 0 | 0 |
| 84 | 11.2 | — | 0 | 0 | 0 | 0 | 0 | 0 | 0 | 0 | 0 | 0 |
| 85 | 11.2 | — | 0 | 0 | 0 | 0 | 0 | 0 | 0 | 0 | 0 | 0 |
| 86 | 11.2 | — | 0 | 0 | 0 | 0 | 0 | 0 | 0 | 0 | 0 | 0 |
| 87 | 11.2 | — | 0 | 0 | 0 | 0 | 0 | 0 | 0 | 0 | 0 | 0 |
| 88 | 11.2 | — | 0 | 1 | 0 | 0 | 0 | 0 | 0 | N | 0 | 0 |
| 89 | 11.2 | — | 0 | 0 | 0 | 0 | 0 | 0 | 0 | N | 0 | 0 |
| 90 | 11.2 | — | 0 | 1 | 0 | 0 | 0 | 0 | 0 | N | 0 | 0 |
| 91 | 11.2 | — | 0 | 0 | 0 | 0 | 0 | 0 | 0 | N | 0 | 0 |
| 92 | 11.2 | — | 0 | 0 | 0 | 0 | 0 | 0 | 0 | N | 0 | 0 |
| 93 | 11.2 | — | 0 | 0 | 0 | 0 | 0 | 0 | 0 | 0 | 0 | 1 |
| 94 | 11.2 | — | 0 | 1 | 0 | 0 | 0 | 0 | 0 | N | 0 | 0 |
| 95 | 11.2 | — | 0 | 1 | 0 | 0 | 0 | 0 | 1 | 0 | 0 | 0 |
| 96 | 11.2 | — | 0 | 1 | 1 | 0 | 0 | 0 | 0 | 0 | 0 | 0 |
| 97 | 11.2 | — | 0 | 0 | 0 | 1 | 0 | 0 | 0 | 0 | 0 | 0 |
| 98 | 11.2 | — | 0 | 0 | 1 | 0 | 0 | 0 | 0 | 0 | 0 | 0 |
| 99 | 11.2 | — | 0 | 1 | 1 | 0 | 0 | 0 | 1 | 0 | 0 | 0 |
| 100 | 11.2 | — | 0 | 1 | 1 | 0 | 0 | 0 | 0 | 0 | 0 | 0 |
| 101 | 11.2 | — | 0 | 0 | N | 0 | 0 | 0 | 0 | 0 | 0 | 1 |
| 102 | 11.2 | — | 1 | 0 | 0 | 0 | 0 | 0 | 0 | 0 | 0 | 1 |
| 103 | 11.2 | 0 | 0 | 0 | 1 | 0 | 0 | 0 | 0 | 0 | 0 | 0 |
| 104 | 11.2 | 0 | 0 | 0 | 0 | 0 | 0 | 0 | 0 | 0 | 0 | 0 |
| 105 | 11.2 | 0 | 0 | 1 | 1 | 0 | 0 | 0 | 0 | 0 | 0 | 0 |
| 106 | 11.2 | 0 | 1 | 1 | 1 | 0 | 0 | 0 | 0 | 0 | 0 | 1 |
| 107 | 11.2 | 1 | 1 | 0 | 1 | 4 | 0 | 1 | 0 | 0 | 0 | 1 |
| 107* | 11.2 | 2 | 1 | 1 | 2 | 4 | 0 | 1 | 0 | 0 | 0 | 1 |
| 108 | 11.2 | 0 | 1 | 1 | 1 | 3 | 0 | 0 | 0 | 0 | 0 | 1 |
| 109 | 11.2 | 0 | 0 | 0 | 0 | 1 | 0 | 0 | 1 | 0 | 0 | 1 |
| 110 | 11.2 | 0 | 0 | 0 | 0 | 0 | 0 | 0 | 0 | 0 | 0 | 0 |
| 111 | 11.2 | 0 | 0 | 0 | 0 | 1 | 0 | 0 | 0 | 0 | 0 | 0 |
| 112 | 11.2 | 0 | 1 | 1 | 0 | 1 | 0 | 0 | 0 | 0 | 0 | 1 |
| 113 | 11.2 | 1 | 1 | 1 | 1 | 0 | 0 | 0 | 0 | 0 | 0 | 0 |
| 114 | 11.2 | 1 | 1 | 0 | 1 | 0 | 0 | 0 | 0 | 0 | 0 | 0 |
| 115 | 11.2 | 0 | 0 | 0 | 0 | 0 | 0 | 0 | 0 | 0 | 0 | 0 |
| 116 | 11.2 | 0 | 0 | 0 | 0 | 0 | 0 | 0 | 0 | 0 | 0 | 0 |
| 117 | 11.2 | 0 | 0 | 0 | 0 | 0 | 0 | 0 | 0 | 0 | 0 | 0 |
| 118 | 11.2 | 0 | N | 1 | 2 | 1 | 1 | 1 | 0 | 0 | 0 | 2 |
| 119 | 11.2 | 0 | 0 | 0 | 0 | 0 | 0 | 0 | 0 | 0 | 0 | 0 |
| 120 | 11.2 | 0 | 0 | 0 | 0 | 0 | 0 | 0 | 0 | 0 | 0 | 0 |
| 121 | 11.2 | 0 | 0 | 0 | 0 | 1 | 0 | 0 | 0 | 0 | 0 | 0 |
| 122 | 11.2 | 0 | 0 | 0 | 0 | 0 | 0 | 0 | 0 | 0 | 0 | 0 |
| 123 | 11.2 | 0 | 0 | 0 | N | 0 | 0 | 0 | 0 | 0 | 0 | 0 |
| 124 | 11.2 | 0 | 0 | 2 | 1 | 1 | 0 | 0 | 0 | 0 | 0 | 1 |
| 125 | 11.2 | 0 | 0 | 1 | N | 1 | 0 | 0 | 0 | 1 | 0 | 2 |
| 126 | 11.2 | 0 | 1 | 0 | N | 0 | 0 | 0 | 0 | 0 | 0 | 0 |
| 127 | 11.2 | N | 2 | 1 | 1 | 0 | 1 | 1 | 0 | 0 | 0 | 2 |
| 128 | 11.2 | 0 | 1 | 0 | 0 | 1 | 0 | 0 | 0 | 0 | 0 | 1 |
| 129 | 11.2 | 0 | 0 | 0 | 0 | 0 | 0 | 0 | 0 | 0 | 0 | 0 |
| 130 | 11.2 | 0 | 1 | 1 | 1 | 0 | 0 | 0 | 0 | 0 | 0 | 1 |
| 131 | 11.2 | 0 | 0 | 0 | 0 | 0 | 0 | 0 | 0 | 0 | 0 | 0 |
| 132 | 11.2 | 0 | 0 | 0 | 0 | 0 | 0 | 0 | 0 | 0 | 0 | 0 |
| 133 | 11.2 | 0 | 0 | 0 | 0 | 0 | 0 | 0 | 0 | 0 | 0 | 0 |
| 134 | 11.2 | 0 | 0 | 0 | 0 | 0 | 0 | 0 | 0 | 0 | 0 | 0 |
| 135 | 11.2 | N | 3 | 2 | 3 | 3 | 1 | 1 | 3 | 1 | 0 | 2 |
| 135* | 11.2 | N | 3 | 2 | 3 | 3 | 2 | 0 | 3 | 1 | 0 | 1 |
| 136 | 11.2 | 4 | 0 | 0 | 2 | 3 | 0 | 0 | 0 | 0 | — | 0 |
| 137 | 11.2 | N | 0 | 0 | 0 | 0 | 0 | 0 | 0 | 0 | 0 | 0 |
| 138 | 11.2 | 0 | 0 | 0 | 0 | 4 | 0 | 0 | 0 | 0 | — | 0 |
| 139 | 11.2 | 0 | 0 | 0 | 0 | 0 | 0 | 0 | 0 | 0 | 0 | 0 |
| 140 | 11.2 | 0 | 0 | 0 | 0 | 0 | 0 | 0 | 0 | N | 0 | 0 |
| 141 | 11.2 | N | 0 | 0 | 0 | 0 | 0 | 0 | 0 | N | 0 | 0 |
| 142 | 11.2 | 0 | 0 | 0 | 0 | 1 | 0 | 0 | 0 | 0 | 0 | 0 |
| 143 | 11.2 | 0 | 1 | 1 | 1 | 0 | 0 | 0 | 0 | N | 0 | 0 |
| 144 | 11.2 | 0 | 0 | 0 | 0 | 0 | 0 | 0 | 0 | 0 | 0 | 0 |
| 145 | 11.2 | 0 | 0 | 0 | 0 | 2 | 0 | 0 | 0 | 0 | 0 | 0 |
| 146 | 11.2 | 0 | 0 | 0 | 0 | 0 | 0 | 0 | 0 | N | 0 | 1 |
| 147 | 11.2 | 0 | 0 | 0 | 0 | 0 | 0 | 0 | 0 | 0 | 0 | 0 |
| 148 | 11.2 | 0 | 0 | 1 | 0 | 1 | 0 | 0 | 0 | 0 | 0 | 0 |
| 149 | 11.2 | 0 | 0 | 0 | 0 | 1 | 0 | 0 | 0 | 0 | 0 | 0 |
| 150 | 11.2 | 0 | 0 | 0 | 0 | 0 | 0 | 0 | 0 | 0 | 0 | 0 |
| 151 | 11.2 | 0 | 0 | 0 | 0 | 1 | 0 | 0 | 0 | 0 | 0 | 0 |
| 152 | 11.2 | 0 | 0 | 1 | 1 | 0 | 0 | 0 | 0 | N | 0 | 0 |

TABLE 4-continued

POST-EMERGENT ACTIVITY FOR WEEDS

| Example No. | Kg/ha | A | B | C | D | E | F | G | H | I | J | K |
|---|---|---|---|---|---|---|---|---|---|---|---|---|
| 153 | 11.2 | 0 | 0 | 0 | 0 | 0 | 0 | 0 | 0 | 0 | 0 | 0 |
| 154 | 11.2 | 0 | 0 | 0 | 0 | 0 | 0 | 0 | N | 0 | 0 | 0 |
| 155 | 11.2 | 0 | 0 | 1 | 1 | 0 | 0 | 0 | 0 | 0 | 0 | 0 |
| 155 | 11.2 | N | 0 | 1 | 0 | 0 | 0 | 0 | 0 | 0 | 0 | 1 |
| 157 | 11.2 | 1 | 0 | 1 | 0 | 0 | 0 | 0 | 0 | 0 | 0 | 0 |
| 158 | 11.2 | 0 | 0 | 0 | 0 | 0 | 0 | 0 | 0 | 0 | 0 | 0 |
| 159 | 11.2 | 0 | 0 | 0 | 0 | 0 | 0 | 0 | 0 | 0 | 0 | 0 |
| 160 | 11.2 | 0 | 0 | 0 | 0 | 0 | 0 | 0 | 0 | 0 | 0 | 1 |
| 161 | 11.2 | 0 | 0 | 0 | 0 | 0 | 0 | 0 | 0 | N | 0 | 0 |
| 162 | 11.2 | 0 | 0 | 0 | 0 | 0 | 0 | 0 | 0 | 0 | 0 | 0 |
| 163 | 11.2 | 0 | 0 | 0 | 0 | 0 | 0 | 0 | 0 | 0 | 0 | 0 |
| 164 | 11.2 | N | 0 | 0 | 0 | 0 | 0 | 0 | 0 | 1 | 0 | 0 |
| 165 | 11.2 | 0 | 0 | 1 | 0 | 0 | 0 | 0 | 0 | 0 | 1 | 0 |
| 166 | 11.2 | 0 | 0 | 0 | 0 | 0 | 0 | 0 | 0 | 0 | 0 | 0 |
| 167 | 11.2 | 1 | 1 | 1 | 1 | 2 | 0 | 0 | 0 | 0 | 0 | 1 |
| 168 | 11.2 | 0 | 0 | 1 | 1 | 0 | 0 | 0 | 0 | 0 | 0 | 0 |
| 169 | 11.2 | N | 0 | 1 | 0 | 0 | 0 | 0 | 0 | 0 | 0 | 0 |
| 170 | 11.2 | 1 | 1 | 1 | 1 | 0 | 0 | 0 | 0 | 0 | 0 | 1 |
| 171 | 11.2 | N | 0 | 0 | 0 | 0 | 0 | 0 | 0 | 0 | 0 | 1 |
| 172 | 11.2 | N | 0 | 0 | 0 | 0 | 0 | 0 | 0 | 0 | 0 | 0 |
| 173 | 11.2 | 0 | 0 | 1 | 0 | 0 | 0 | 0 | 0 | 0 | 0 | 0 |
| 174 | 11.2 | 0 | 0 | 0 | 0 | 0 | 0 | 0 | 0 | 0 | 0 | 0 |
| 175 | 11.2 | 0 | 0 | 0 | 0 | 0 | 0 | 0 | 0 | 0 | 0 | 0 |
| 176 | 11.2 | 0 | 0 | 1 | 0 | N | 0 | 0 | 0 | 0 | 0 | 0 |
| 177 | 11.2 | 0 | 0 | 0 | 0 | 0 | 0 | 0 | 0 | 0 | 0 | 0 |
| 178 | 11.2 | 0 | 0 | 0 | 0 | 0 | 0 | 0 | 0 | 0 | 0 | 0 |
| 179 | 11.2 | 0 | 0 | 0 | 0 | 0 | 0 | 0 | 0 | 0 | 0 | 0 |
| 180 | 11.2 | 0 | 0 | 1 | 0 | 0 | 0 | 0 | 0 | 0 | 0 | 1 |
| 181 | 11.2 | 0 | 0 | 0 | 0 | 0 | 0 | 0 | 0 | 0 | 0 | 0 |
| 182 | 11.2 | 0 | 0 | 0 | 0 | N | 0 | 0 | 0 | 0 | 0 | 0 |
| 183 | 11.2 | 0 | 0 | 0 | 0 | 0 | 0 | 0 | 0 | 0 | 0 | 0 |
| 184 | 11.2 | 0 | 0 | 1 | 0 | N | 0 | 0 | 0 | 0 | 0 | 0 |
| 185 | 11.2 | 0 | 0 | 0 | 0 | N | 0 | ) | 0 | 0 | 0 | 0 |
| 186 | 11.2 | 0 | 0 | 0 | 0 | 0 | 0 | 0 | 0 | 0 | 0 | 0 |
| 187 | 11.2 | 0 | 0 | 0 | 0 | 0 | 0 | 0 | 0 | 0 | 0 | 0 |
| 188 | 11.2 | 1 | 2 | 1 | 1 | 1 | 0 | 0 | 0 | 0 | 0 | 1 |
| 189 | 11.2 | 0 | 0 | 0 | 0 | 0 | 0 | 0 | 0 | 0 | 0 | 0 |
| 190 | 11.2 | 0 | 0 | 0 | 0 | 0 | 0 | 0 | 0 | 0 | 0 | 0 |
| 191 | 11.2 | 0 | 0 | 0 | 0 | 0 | 0 | 0 | 0 | 0 | 0 | 0 |
| 192 | 11.2 | 0 | 0 | 0 | 0 | 0 | 0 | 0 | 0 | 0 | 0 | 0 |
| 193 | 11.2 | 0 | 0 | 0 | 0 | 0 | 0 | 0 | 0 | 0 | 0 | 0 |
| 194 | 11.2 | 0 | 0 | 0 | 0 | 0 | 0 | 0 | 0 | N | 0 | 1 |
| 195 | 11.2 | 0 | 0 | 0 | 0 | 0 | 0 | 0 | 0 | N | 0 | 0 |
| 196 | 11.2 | 0 | 0 | 0 | 0 | 0 | 0 | 0 | 0 | N | 0 | 0 |
| 197 | 11.2 | 0 | 0 | 0 | 0 | 0 | 0 | 0 | 0 | 0 | 0 | 0 |
| 198 | 11.2 | 0 | 0 | 0 | 0 | 0 | 0 | 0 | 0 | 0 | 0 | 0 |
| 199 | 11.2 | 0 | 0 | 0 | 0 | 0 | 0 | 0 | 0 | 0 | 0 | 0 |
| 200 | 11.2 | 0 | 0 | 0 | 0 | 0 | 0 | 0 | 0 | 0 | 0 | 0 |
| 201 | 11.2 | 0 | 0 | 0 | 0 | 0 | 0 | 0 | 0 | 0 | 0 | 0 |
| 202 | 11.2 | 0 | 0 | 0 | 0 | 0 | 0 | 0 | 0 | 0 | 0 | 0 |
| 203 | 11.2 | 0 | 0 | 0 | 0 | 0 | 0 | 0 | 0 | 0 | 0 | 0 |
| 204 | 11.2 | 0 | 0 | 0 | 0 | 0 | 0 | 0 | 0 | 0 | 0 | 0 |
| 205 | 11.2 | 0 | 0 | 0 | 0 | 0 | 0 | 0 | 0 | 0 | 0 | 0 |
| 206 | 11.2 | 0 | 0 | 0 | 0 | 0 | 0 | 0 | 0 | 0 | 0 | 0 |
| 207 | 11.2 | 0 | 0 | 0 | 0 | 1 | 0 | 0 | 0 | 0 | 0 | 0 |
| 208 | 11.2 | 0 | 0 | 0 | 0 | 0 | 0 | 0 | 0 | N | 0 | 0 |

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially waterimmiscible solvents together with a surface active agent. Suitable solvents for the active ingredient of this invention include dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a2',1'-c)-pyrazidiinium salt
5-Bromo-3-isopropyl-6-methyluracil 1,1'-Dimethyl4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

Ureas

N-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)]benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2yl)amino)carbonyl)amino)sulfonyl) benzoate

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[(trifluoromethyl)sulfonyl]amino]-phenyl]acetamide   N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide   α,α,α-Trifluoro-2,6-dinitro-N,N-dipropyl-p-toluidine
N-1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol   N-(phosphonomethyl) glycine and its salts.
Butyl 2-[4-[(5-(trifluoromethyl)-2-pyridinyl)oxy]-phenoxy]-propanoate

Ethers 2,4-Dichlorophenyl-4-nitrophenyl ether
2-Chloro-α,α,α-trifluoro-p-tolyl-3-ethoxy-4nitrodiphenyl ether
5-(2-chloro-4-trifluoromethylphenoxy)-N-methylsulfonyl 2-nitrobenzamide 1'-(Carboethoxy) ethyl 5-[2-chloro-4-(trifluoromethyl)phenoxy]-2-nitrobenzoate

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabioyclo (2.2.1) heptane, 1-methyl-4-(1-methyl ethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | | Weight Percent |
|---|---|---|
| I. Emulsifiable Concentrates | | |
| A. | Compound of Example No. 3 | 11.0 |
| | Free acid of complex organic phosphate or aromatic or aliphatic hydrophobe base (e.g., GAFAC RE-610, registered trademark of GAF Corp.) | 5.59 |

-continued

| | | Weight Percent |
|---|---|---|
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 14 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |
| II. Flowables | | |
| A. | Compound of Example No. 24 | 25.00 |
| | Methyl cellulose | 0.3 |
| | Silica Aerogel | 1.5 |
| | Sodium lignosulfonate | 3.5 |
| | Sodium N-methyl-N-oleyl taurate | 2.0 |
| | Water | 67.7 |
| | | 100.00 |
| B. | Compound of Example No. 18 | 45.0 |
| | Methyl cellulose | .3 |
| | Silica aerogel | 1.5 |
| | Sodium lignosulfonate | 3.5 |
| | Sodium N-methyl-N-oleyl taurate | 2.0 |
| | Water | 47.7 |
| | | 100.00 |
| III. Wettable Powders | | |
| A. | Compound of Example No. 5 | 25.0 |
| | Sodium lignosulfonate | 3.0 |
| | Sodium N-methyl-N-oleyl-taurate | 1.0 |
| | Amorphous silica (synthetic) | 71.0 |
| | | 100.00 |
| B. | Compound of Example 21 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 6 | 10.0 |
| | Sodium lignosulfonate | 3.0 |
| | Sodium N-methyl-N-oleyl-taurate | 1.0 |
| | Kaolinite clay | 86.0 |
| | | 100.00 |
| IV. Dusts | | |
| A. | Compound of Example No. 13 | 2.0 |
| | Attapulgite | 98.0 |
| | | 100.00 |
| B. | Compound of Example No. 10 | 60.0 |
| | Montmorillonite | 40.0 |
| | | 100.00 |
| C. | Compound of Example No. 54 | 30.0 |
| | Ethylene glycol | 1.0 |
| | Bentonite | 69.0 |
| | | 100.00 |
| D. | Compound of Example No. 62 | 1.0 |
| | Diatomaceous earth | 99.0 |
| | | 100.00 |
| V. Granules | | |
| A. | Compound of Example No. 52 | 15.0 |
| | Granular attapulgite (20/40 mesh) | 85.0 |
| | | 100.00 |
| B. | Compound of Example No. 70 | 30.0 |
| | Diatomaceous earth (20/40) | 70.0 |
| | | 100.00 |
| C. | Compound of Example No. 58 | 1.0 |
| | Ethylene glycol | 5.0 |
| | Methylene blue | 0.1 |
| | Pyrophyllite | 93.9 |
| | | 100.00 |
| D. | Compound of Example No. 46 | 5.0 |

-continued

| | | Weight Percent |
|---|---|---|
| | Pyrophyllite (20/40) | 95.0 |
| | | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations.

We claim:

1. A compound having the structural formula

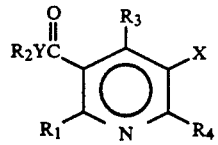

wherein:

Y is selected from O and S;

$R_1$ and $R_4$ are independently selected from fluorinated methyl, chlorofluorinated methyl, and $C_1$-$C_4$ alkyl, provided that not both $R_1$ and $R_4$ may be $C_1$-$C_4$ alkyl;

$R_2$ is selected from hydrogen, lower alkyl, haloalkyl, alkenyl, alkynyl, haloalkenyl, and a cation;

$R_3$ is selected from $C_1$-$C_5$ alkyl, cycloalkyl, cycloalkylalkyl, hydroxy, and alkoxy; and X is selected from a halogen.

2. A compound according to claim 1 wherein $R_1$ is $CF_3$ and $R_4$ is $CF_2H$.

3. A compound according to claim 2 wherein X is selected from Cl, Br, and I.

4. A compound according to claim 1 wherein $R_1$ is $CF_2H$ and $R_4$ is $CF_3$.

5. A compound according to claim 4 wherein X is selected from Cl, Br, and I.

6. A compound according to claim 1 wherein $R_1$ is $CF_3$ and $R_4$ is $CH_3$.

7. A herbicidal composition containing a carrier and a compound having the structural formula

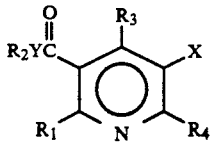

wherein:

Y is selected from O and S;

$R_1$ and $R_4$ are independently selected from fluorinated methyl, chlorofluorinated methyl, and $C_1-C_4$ alkyl, provided that not both $R_1$ and $R_4$ may be $C_1-C_4$ alkyl;

$R_2$ is selected from hydrogen, lower alkyl, and a cation;

$R_3$ is selected from $C_1-C_5$ alkyl, cycloalkyl, cycloalkylalkyl, hydroxy, and alkoxy; and X is selected from a) a halogen;

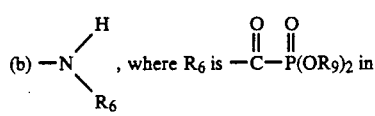, where $R_6$ is $-C-P(OR_9)_2$ in which $R_9$ is $C_1-C_4$ alkyl;

c) $-N_3$;

d)

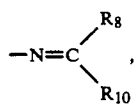

in which $R_8$ is selected from H, alkyl and $CF_3$ and $R_{10}$ is selected from F, Cl, $-OR^1$, $-SR^1$, $-NHR^1$, $-N(R^1)_2$, phenyl, phenyl substituted with $CF_3$ or F and

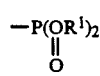

wherein $R^1$ is as defined above;

e) $-N=S=O$;

f) $-NO_2$

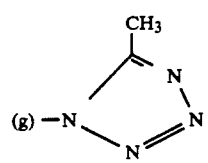

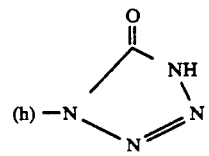

-continued

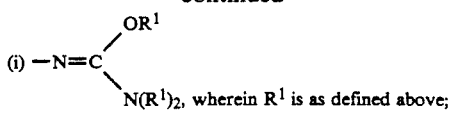, wherein $R^1$ is as defined above;

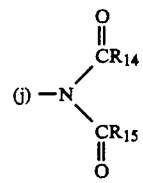

wherein $R_{14}$ and $R_{15}$ are independently selected from hydrogen and alkyl; and alkyl; and k) $-N=C=O$.

8. A composition according to claim 7 wherein $R_1$ is $CF_3$ and $R_4$ is $CF_2H$.

9. A composition according to claim 8 wherein X is selected from Cl, Br, and I.

10. A composition according to claim 7 wherein $R_1$ is $CF_2H$ and $R_4$ is $CF_3$.

11. A composition according to claim 10 wherein X is selected from Cl, Br, and I.

12. A composition according to claim 7 wherein $R_1$ is $CF_3$ and $R_4$ is $CH_3$.

13. A herbicidal method comprising applying to the plant locus an effective amount of a compound having the structural formula

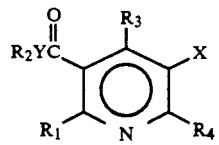

wherein:

Y is selected from O and S;

$R_1$ and $R_4$ are independently selected from fluorinated methyl, chlorofluorinated methyl, and $C_1-C_4$ alkyl, provided that not both $R_1$ and $R_4$ may be $C_1-C_4$ alkyl;

$R_2$ is selected from hydrogen, lower alkyl, and a cation;

$R_3$ is selected from $C_1-C_5$ alkyl, cycloalkyl, cycloalkylalkyl, hydroxy, and alkoxy; and X is selected from a) a halogen;

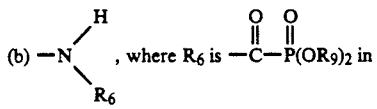, where $R_6$ is $-C-P(OR_9)_2$ in which $R_9$ is $C_1-C_4$ alkyl;

c) $-N_3$;

d)

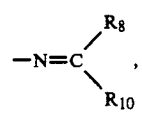

in which $R_8$ is selected from H, alkyl and $CF_3$ and $R_{10}$ is selected from F, Cl, $-OR^1$, $-SR^1$, $-NHR^1$, $-N(R^1)_2$, phenyl, phenyl substituted with $CF_3$ or F and where $R^1$ is as defined above;

e) —N=S=O;
f) —NO₂

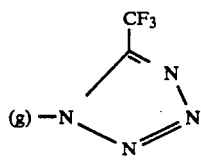

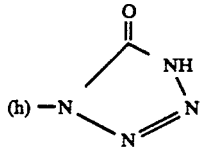

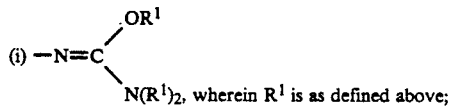

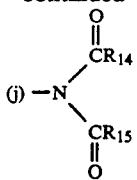

wherein $R_{14}$ and $R_{15}$ are independently selected from hydrogen and alkyl; and k) —N=C=O.

14. A method according to claim 13 wherein $R_1$ is $CF_3$ and $R_4$ is $CF_2H$.

15. A method according to claim 14 wherein X is selected from Cl, Br, and I.

16. A method according to claim 13 wherein $R_1$ is $CF_2H$ and $R_4$ is $CF_3$.

17. A method according to claim 16 wherein X is selected from Cl, Br, and I.

18. A method according to claim 13 wherein $R_1$ is $CF_3$ and $R_4$ is $CH_3$.

* * * * *

UNITED STATES PATENT AND TRADEMARK OFFICE
CERTIFICATE OF CORRECTION

PATENT NO. : 5,019,153
DATED : May 28, 1991
INVENTOR(S) : Len F. Lee et al.

It is certified that error appears in the above-identified patent and that said Letters Patent is hereby corrected as shown below:

On the title page: Substitute the following Abstract
--Disclosed herein are pyridine compounds having the structural formula

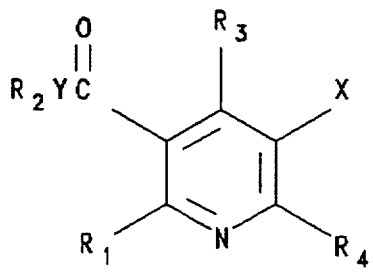

wherein $R_1$ and $R_4$ are fluorinated methyl, chlorofluorinated methyl or alkyl; $R_2$ is hydrogen, alkyl, haloalkyl, alkenyl, alkynyl, haloalkenyl or a cation; $R_3$ is alkyl, cycloalkyl, cycloalkylalkyl, hydroxy, or alkoxy; and X is a halogen. --.

| Col. | Line | |
|---|---|---|
| 1 | 56 | Remove "U.S. Patent No. 4,592,184" and insert -- U.S. Patent No. 4,692,184 --. |
| 4 | 32 | Remove "NaNa" and insert -- $NaN_3$ --. |
| 7 | 28 | Remove "undec-5-ene" and insert -- undec-7-ene --. |

UNITED STATES PATENT AND TRADEMARK OFFICE
CERTIFICATE OF CORRECTION

PATENT NO. : 5,019,153
DATED : May 28, 1991
INVENTOR(S) : Len F. Lee et al.

Page 2 of 7

It is certified that error appears in the above-identified patent and that said Letters Patent is hereby corrected as shown below:

| | | |
|---|---|---|
| 11 | 13 | Remove "Calculated 6.75" and insert -- Calculated 46.75 --. |
| 13 | 64 | Remove "CHCls" and insert -- $CHCl_3$ --. |
| 14 | 18 | Remove "1 462." and insert -- 1.462. --. |
| 16 | 42 | Remove "25". |
| 19 | 22-3 | Remove "3-Pyridinecarboxylic acid, 6-(difluorofluoromethyl)-, ethyl ester." and insert -- 3-Pyridinecarboxylic acid, 6-(difluoromethyl)-4-ethyl-5-[(methoxymethylene)amino]-2-(trifluoromethyl)-, ethyl ester. --. |
| 19 | 40 | Remove "5 3-Pyridinecarboxylic acid," and insert -- 3-Pyridinecarboxylic acid, --. |
| 19 | 58 | Remove "3-Pyridinecarboxylio acid" and insert -- 3-Pyridinecarboxylic acid --. |
| 21 | 26 | Remove "5-(n-butoxyme-" and insert -- 5-[(n-butoxyme- --. |
| 23 | 16 | Remove "2-trifluoroethylidine) amino-2-" and insert -- 2-trifluoromethylidine)amino]-2- --. |
| 24 | 30 | Remove "ethyl-2-(trifluoromethyl]-5-" and insert -- ethyl-2-(trifluoromethyl)-5- --. |

UNITED STATES PATENT AND TRADEMARK OFFICE
CERTIFICATE OF CORRECTION

PATENT NO. : 5,019,153

DATED : May 28, 1991

INVENTOR(S) : Len F. Lee et al.

Page 3 of 7

It is certified that error appears in the above-identified patent and that said Letters Patent is hereby corrected as shown below:

| | | |
|---|---|---|
| 25 | 41 | Remove "amino]-" and insert -- amino}---. |
| 27 | 3-4 | Remove "3-Pyridinecarboxylic acid, 6-(difluoro-2-(trifluoromethyl)-, methyl ester." and insert -- 3-Pyridinecarboxylic acid, 6-(difluoromethyl)-4-ethyl-5-{[(1-methylethoxy)carbonyl]amino}-2-(trifluoromethyl)-, methyl ester. --. |
| 27 | 20 | Remove "-5-(1-methylethylthio)carbonyl]amino}-2-" and insert -- -5-{[(methylethylthio)carbonyl]amino}-2- --. |
| 27 | 39 | Remove "([(1,1-dimethylethyl)thio]carbonyl}amino)-" and insert -- ({[(1,1-dimethylethyl)thio]carbonyl}amino)- --. |
| 28 | 56 | Remove "5-{(2-chloroethoxy)" and insert -- 5-{[(2-chloroethoxy) --. |
| 29 | 8 | Remove "diethoxyphosphinyl)-" and insert -- diethoxyphosphinyl) --. |
| 30 | 5 | Remove "(0.02B mol)" and insert -- (0.028 mol) --. |
| 31 | 67 | Remove "Found   35.77" and insert -- Found 35.83 --. |
| 33 | 38 | Remove "1.470" and insert -- 1.484 --. |

UNITED STATES PATENT AND TRADEMARK OFFICE
CERTIFICATE OF CORRECTION

PATENT NO. : 5,019,153

DATED : May 28, 1991

INVENTOR(S) : Len F. Lee et al.

It is certified that error appears in the above-identified patent and that said Letters Patent is hereby corrected as shown below:

| | | |
|---|---|---|
| 33 | 55 | Remove "j". |
| 34 | 5 | Remove "solution of 4.0 9" and insert -- solution of 4.0 g --. |
| 35 | 15 | Remove "ethyl-5-{2,2,2-trifluoro" and insert -- ethyl-5-{[2,2,2-trifluoro --. |
| 35 | 35 | Remove "ethyl-5-{2,2,2-trifluoro" and insert -- ethyl-5-{[2,2,2-trifluoro --. |
| 35 | 53 | Remove "5-(ethoxyme-" and insert -- 5-[(ethoxyme --. |
| 36 | 35 | Remove "was" and insert -- as --. |
| 38 | 42 | Remove "5.07 g of product" and insert -- 5.07 g (88%) of product --. |
| 38 | 61 | Remove "3.90 g of product" and insert -- 3.90 g (83%) of product --. |
| 39 | 3 | Remove "20". |
| 39 | 8 | Remove "overnight at °C." and insert -- overnight at 100°C. --. |
| 39 | 10 | Remove "silica gel ethyl" and insert -- silica gel using 5% ethyl --. |

UNITED STATES PATENT AND TRADEMARK OFFICE
CERTIFICATE OF CORRECTION

PATENT NO. : 5,019,153
DATED : May 28, 1991
INVENTOR(S) : Len F. Lee et al.

It is certified that error appears in the above-identified patent and that said Letters Patent is hereby corrected as shown below:

| | | |
|---|---|---|
| 40 | 2 | Remove "2.65 g of product" and insert -- 2.65 g (50%) of product --. |
| 40 | 3 | Remove "1.4S9" and insert -- 1.459 --. |
| 40 | 17 | Remove "Example 08" and insert -- Example 108 --. |
| 40 | 33 | Remove "-4-propyl2-" and insert -- -4-propyl-2- --. |
| 42 | 11 | Remove "10". |
| 42 | 24 | Remove "2,2,2-L.iflucrc 1-(methylamino)" and insert -- 2,2,2-trifluoro-1-(methylamino) --. |
| 43 | 15 | Remove "ethyl-5-[dimethoxymethylene)amino]" and insert -- ethyl-5-[(methoxymethylene)amino] --. |
| 43 | 56 | Remove "I 466" and insert -- 1.466 --. |
| 46 | 19 | Remove "{(dimethylamino)methylene]amino}" and insert -- {[(dimethylamino)methylene]amino} --. |
| 47 | 33 | Remove "5-(1-chloro-2,2,2-trifluoro-" and insert -- 5-[(1-chloro-2,2,2-trifluoro- --. |
| 47 | 37 | Remove "PCls" and insert -- $PCl_5$ --. |

UNITED STATES PATENT AND TRADEMARK OFFICE
CERTIFICATE OF CORRECTION

PATENT NO. : 5,019,153
DATED : May 28, 1991
INVENTOR(S) : Len F. Lee et al.

It is certified that error appears in the above-identified patent and that said Letters Patent is hereby corrected as shown below:

| | | |
|---|---|---|
| 48 | 32 | Remove "trifluoroethylidene]amino]-6-" and insert -- trifluoroethylidene]amino}-6- --. |
| 48 | 51 | Remove "-5-{1-" and insert -- -5-{[1- --. |
| 49 | 30 | Remove "HcL" and insert -- HCl --. |
| 57 | 10 | Remove "test" and insert -- tests --. |
| 60 | 33 | Remove "CHOP" and insert -- CROP --. |
| 63 | | Exp.# 56  Remove "0.056     0000000000000000". |
| 69 | | Exp.#110  Remove "1.12  0000000001000000" and insert -- 1.12   0000000010000000 --. |
| 71 | | Exp.#151  Remove "0.28   0000000000100101" and insert -- 0.28    0000000001000101 --. |
| 82 | 17 | Remove "N-1,1-dimethylpropynyl)" and insert -- N-(1,1-dimethylpropynyl) --. |
| 82 | 37 | Remove "-4nitrodiphe-" and insert -- -4-nitrodiphe- --. |
| 82 | 49 | Remove "7-oxabioyclo" and insert -- 7-oxabicyclo --. |
| 84 | 62 | Remove "selected from". |

UNITED STATES PATENT AND TRADEMARK OFFICE
CERTIFICATE OF CORRECTION

PATENT NO. : 5,019,153

DATED : May 28, 1991

INVENTOR(S) : Len T. Lee et al.

It is certified that error appears in the above-identified patent and that said Letters Patent is hereby corrected as shown below:

| | | |
|---|---|---|
| 85 | 26 | through |
| 86 | 17 | Remove all text beginning at "X is selected from ..." and ending at "k) -N=C=O." and insert -- X is a halogen. --. |
| 86 | 49 | through |
| 88 | 12 | Remove all text beginning at "X is selected from ..." and ending at "k) -N=C=O." and insert -- X is a halogen. --. |

Signed and Sealed this

Seventh Day of March, 1995

Attest:

BRUCE LEHMAN

Attesting Officer — Commissioner of Patents and Trademarks